(12) United States Patent
Belhe et al.

(10) Patent No.: US 9,173,760 B2
(45) Date of Patent: Nov. 3, 2015

(54) DELIVERY DEVICES AND METHODS FOR GASTROINTESTINAL IMPLANTS

(71) Applicant: MetaModix, Inc., Plymouth, MN (US)

(72) Inventors: Kedar R. Belhe, Minnetonka, MN (US); Paul J. Thompson, Minnetonka, MN (US); Alexander D. Grafov, Eden Prairie, MN (US); Werner Schwarz, Ruhpolding (DE)

(73) Assignee: MetaModix, Inc., Plymouth, MN (US)

( * ) Notice: Subject to any disclaimer, the term of this patent is extended or adjusted under 35 U.S.C. 154(b) by 308 days.

(21) Appl. No.: 13/632,083

(22) Filed: Sep. 30, 2012

(65) Prior Publication Data

US 2013/0030351 A1    Jan. 31, 2013

Related U.S. Application Data

(60) Continuation-in-part of application No. 13/493,144, filed on Jun. 11, 2012, which is a division of application No. 12/752,697, filed on Apr. 1, 2010, now Pat. No. 8,211,186, application No. 13/632,083, filed (Continued)

(51) Int. Cl.
*A61F 2/04* (2013.01)
*A61F 5/00* (2006.01)

(52) U.S. Cl.
CPC .............. *A61F 5/0076* (2013.01); *A61F 5/0079* (2013.01); *A61F 5/0089* (2013.01); *A61F 2002/044* (2013.01); *A61F 2002/045* (2013.01)

(58) Field of Classification Search
CPC ....... A61F 2/04; A61F 5/0079; A61F 5/0089; A61F 2002/045; A61F 2002/044; A61B 2018/00273; A61B 2018/00279; A61B 2017/3484; A61B 2017/348
See application file for complete search history.

(56) References Cited

U.S. PATENT DOCUMENTS

| 4,134,405 A | 1/1979 | Smit |
| 4,204,530 A | 5/1980 | Finney |

(Continued)

FOREIGN PATENT DOCUMENTS

| AU | 2006227471 B2 | 9/2006 |
| CN | 1618411 A | 5/2005 |

(Continued)

OTHER PUBLICATIONS

International Search Report and Written Opinion issued in PCT/US2014/011702, mailed Mar. 21, 2014, 9 pages.

(Continued)

*Primary Examiner* — Tatyana Zalukaeva
*Assistant Examiner* — Sara Sass
(74) *Attorney, Agent, or Firm* — Faegre Baker Daniels LLP

(57) ABSTRACT

Several gastrointestinal surgery procedures are effective as treatments for metabolic disorders such as obesity and diabetes. Minimally invasive procedures including intra-luminal gastrointestinal implants have been proposed to mimic the anatomical, physiological and metabolic changes achieved by these procedures. Many of these designs include long sleeve like elements that prevent contact of food with the walls of the small intestine. It is desirable to have simple delivery systems that can place these implants under endoscopic guidance. However, in order to anchor these sleeve elements safely and reliably, the inventors have previously disclosed anchoring means that anchor the sleeves at the junctions of the stomach and the intestine or the stomach and esophagus.

9 Claims, 64 Drawing Sheets

Related U.S. Application Data on Sep. 30, 2012, which is a continuation-in-part of application No. 12/833,605, filed on Jul. 9, 2010, now Pat. No. 8,282,598, and a continuation-in-part of application No. 12/986,268, filed on Jan. 7, 2011, now Pat. No. 8,702,641, and a continuation-in-part of application No. 13/298,867, filed on Nov. 17, 2011, and a continuation-in-part of application No. 13/360,689, filed on Jan. 28, 2012.

(60) Provisional application No. 61/626,658, filed on Sep. 30, 2011, provisional application No. 61/211,853, filed on Apr. 3, 2009, provisional application No. 61/270,588, filed on Jul. 10, 2009, provisional application No. 61/335,472, filed on Jan. 7, 2010, provisional application No. 61/458,060, filed on Nov. 17, 2010, provisional application No. 61/462,156, filed on Jan. 28, 2011, provisional application No. 61/519,507, filed on May 24, 2011.

(56) References Cited

U.S. PATENT DOCUMENTS

| | | |
|---|---|---|
| 4,246,893 A | 1/1981 | Berson |
| 4,314,405 A | 2/1982 | Park |
| 4,315,509 A | 2/1982 | Smit |
| 4,416,267 A | 11/1983 | Garren et al. |
| 4,501,264 A | 2/1985 | Rockey |
| 4,641,653 A | 2/1987 | Rockey |
| 4,716,900 A | 1/1988 | Ravo et al. |
| 4,719,916 A | 1/1988 | Ravo |
| 4,763,653 A | 8/1988 | Rockey |
| 4,899,747 A | 2/1990 | Garren et al. |
| 4,905,693 A | 3/1990 | Ravo |
| 5,234,454 A | 8/1993 | Bangs |
| 5,246,456 A | 9/1993 | Wilkinson |
| 5,306,300 A | 4/1994 | Berry |
| 5,322,697 A | 6/1994 | Meyer |
| 5,423,872 A | 6/1995 | Cigaina |
| 5,474,563 A | 12/1995 | Myler et al. |
| 5,480,423 A | 1/1996 | Ravenscroft et al. |
| 5,749,921 A | 5/1998 | Lenker et al. |
| 5,753,253 A | 5/1998 | Meyer |
| 5,820,584 A | 10/1998 | Crabb |
| 6,017,563 A | 1/2000 | Knight et al. |
| 6,224,627 B1 | 5/2001 | Armstrong et al. |
| 6,267,988 B1 | 7/2001 | Meyer |
| 6,454,699 B1 | 9/2002 | Forsell |
| 6,540,789 B1 | 4/2003 | Silverman et al. |
| 6,558,400 B2 | 5/2003 | Deem et al. |
| 6,675,809 B2 | 1/2004 | Stack et al. |
| 6,740,121 B2 | 5/2004 | Geitz |
| 6,755,869 B2 | 6/2004 | Geitz |
| 6,802,868 B2 | 10/2004 | Silverman et al. |
| 6,845,776 B2 | 1/2005 | Stack et al. |
| 6,946,002 B2 | 9/2005 | Geitz |
| 6,994,095 B2 | 2/2006 | Burnett |
| 7,025,791 B2 | 4/2006 | Levine et al. |
| 7,037,343 B2 | 5/2006 | Imran |
| 7,037,344 B2 | 5/2006 | Kagan et al. |
| 7,044,979 B2 | 5/2006 | Silverman et al. |
| 7,090,699 B2 | 8/2006 | Geitz |
| 7,111,627 B2 | 9/2006 | Stack et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,152,607 B2 | 12/2006 | Stack et al. |
| 7,160,312 B2 | 1/2007 | Saadat |
| 7,163,554 B2 | 1/2007 | Williams et al. |
| 7,175,638 B2 | 2/2007 | Gannoe et al. |
| 7,175,669 B2 | 2/2007 | Geitz |
| 7,211,094 B2 | 5/2007 | Gannoe et |
| 7,211,114 B2 | 5/2007 | Bessler et |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,261,725 B2 | 8/2007 | Binmoeller |
| 7,267,694 B2 | 9/2007 | Levine et al. |
| 7,288,099 B2 | 10/2007 | Deem et al. |
| 7,288,101 B2 | 10/2007 | Deem et al. |
| 7,291,160 B2 | 11/2007 | DeLegge |
| 7,306,614 B2 | 12/2007 | Weller et al. |
| 7,314,489 B2 | 1/2008 | McKenna et al. |
| 7,316,716 B2 | 1/2008 | Egan |
| 7,329,285 B2 | 2/2008 | Levine et al. |
| 7,335,210 B2 | 2/2008 | Smit |
| 7,347,875 B2 | 3/2008 | Levine et al. |
| 7,354,454 B2 | 4/2008 | Stack et al. |
| 7,364,542 B2 | 4/2008 | Jambor et al. |
| 7,364,591 B2 | 4/2008 | Silverman et al. |
| 7,367,937 B2 | 5/2008 | Jambor et al. |
| 7,431,725 B2 | 10/2008 | Stack et al. |
| 7,476,256 B2 | 1/2009 | Meade et al. |
| 7,503,922 B2 | 3/2009 | Deem et al. |
| 7,507,218 B2 | 3/2009 | Aliski et al. |
| 7,510,559 B2 | 3/2009 | Deem et al. |
| 7,513,914 B2 | 4/2009 | Schurr |
| 7,569,056 B2 | 8/2009 | Cragg et al. |
| 7,601,178 B2 | 10/2009 | Imran |
| 7,608,114 B2 | 10/2009 | Levine et al. |
| 7,608,578 B2 | 10/2009 | Miller |
| 7,618,435 B2 | 11/2009 | Opolski |
| 7,628,821 B2 | 12/2009 | Stack et al. |
| 7,678,068 B2 | 3/2010 | Levine et al. |
| 7,682,330 B2 | 3/2010 | Meade et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,815,589 B2 | 10/2010 | Levine et al. |
| 7,837,643 B2 | 11/2010 | Levine et al. |
| 7,837,669 B2 | 11/2010 | Dann et al. |
| 7,935,073 B2 | 5/2011 | Levine et al. |
| 7,976,488 B2 | 7/2011 | Levine et al. |
| 7,981,163 B2 | 7/2011 | Levine et al. |
| 8,114,045 B2 | 2/2012 | Surti |
| 8,211,186 B2 | 7/2012 | Belhe et al. |
| 8,282,598 B2 | 10/2012 | Belhe et al. |
| 8,579,849 B2 | 11/2013 | Grau et al. |
| 8,702,641 B2 | 4/2014 | Belhe et al. |
| 8,702,642 B2 | 4/2014 | Belhe et al. |
| 8,882,698 B2 | 11/2014 | Levine et al. |
| 2002/0183768 A1 | 12/2002 | Deem et al. |
| 2002/0188354 A1 | 12/2002 | Peghini |
| 2003/0040804 A1 | 2/2003 | Stack et al. |
| 2003/0040808 A1 | 2/2003 | Stack et al. |
| 2003/0060894 A1 | 3/2003 | Dua et al. |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0158601 A1 | 8/2003 | Silverman et al. |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2004/0019388 A1 | 1/2004 | Starkebaum |
| 2004/0024386 A1 | 2/2004 | Deem et al. |
| 2004/0039452 A1 | 2/2004 | Bessler |
| 2004/0088022 A1 | 5/2004 | Chen |
| 2004/0092892 A1 | 5/2004 | Kagan et al. |
| 2004/0093091 A1 | 5/2004 | Gannoe et al. |
| 2004/0107004 A1 | 6/2004 | Levine et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122526 A1 | 6/2004 | Imran |
| 2004/0133147 A1 | 7/2004 | Woo |
| 2004/0138760 A1 | 7/2004 | Schurr |
| 2004/0138761 A1 | 7/2004 | Stack et al. |
| 2004/0143342 A1 | 7/2004 | Stack et al. |

(56) References Cited

U.S. PATENT DOCUMENTS

| | | |
|---|---|---|
| 2004/0148034 A1 | 7/2004 | Kagan et al. |
| 2004/0158331 A1 | 8/2004 | Stack et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0199262 A1 | 10/2004 | Dua et al. |
| 2004/0204768 A1 | 10/2004 | Geitz |
| 2004/0220682 A1 | 11/2004 | Levine et al. |
| 2004/0249362 A1 | 12/2004 | Levine et al. |
| 2005/0004681 A1 | 1/2005 | Stack et al. |
| 2005/0022827 A1 | 2/2005 | Woo et al. |
| 2005/0033331 A1 | 2/2005 | Burnett et al. |
| 2005/0043817 A1 | 2/2005 | McKenna et al. |
| 2005/0049718 A1 | 3/2005 | Dann et al. |
| 2005/0055039 A1 | 3/2005 | Burnett et al. |
| 2005/0070934 A1 | 3/2005 | Tanaka et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080444 A1* | 4/2005 | Kraemer et al. ............... 606/192 |
| 2005/0080480 A1 | 4/2005 | Bolea et al. |
| 2005/0080491 A1 | 4/2005 | Levine et al. |
| 2005/0085923 A1 | 4/2005 | Levine et al. |
| 2005/0096673 A1 | 5/2005 | Stack et al. |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149200 A1 | 7/2005 | Silverman et al. |
| 2005/0177181 A1 | 8/2005 | Kagan et al. |
| 2005/0183730 A1 | 8/2005 | Byrum |
| 2005/0192614 A1 | 9/2005 | Binmoeller |
| 2005/0197714 A1 | 9/2005 | Sayet |
| 2005/0228413 A1 | 10/2005 | Binmoeller et al. |
| 2005/0228504 A1 | 10/2005 | Demarais |
| 2005/0240279 A1 | 10/2005 | Kagan et al. |
| 2005/0246037 A1 | 11/2005 | Starkebaum |
| 2005/0247320 A1 | 11/2005 | Stack et al. |
| 2005/0250980 A1 | 11/2005 | Swanstrom et al. |
| 2005/0251157 A1 | 11/2005 | Saadat et al. |
| 2005/0251206 A1 | 11/2005 | Maahs et al. |
| 2005/0256587 A1 | 11/2005 | Egan |
| 2005/0267499 A1 | 12/2005 | Stack et al. |
| 2005/0273060 A1 | 12/2005 | Levy et al. |
| 2005/0277963 A1 | 12/2005 | Fields |
| 2005/0283107 A1 | 12/2005 | Kalanovic et al. |
| 2005/0288555 A1 | 12/2005 | Binmoeller |
| 2006/0009858 A1 | 1/2006 | Levine et al. |
| 2006/0020247 A1 | 1/2006 | Kagan et al. |
| 2006/0020277 A1 | 1/2006 | Gostout et al. |
| 2006/0030949 A1 | 2/2006 | Geitz |
| 2006/0036267 A1 | 2/2006 | Saadat et al. |
| 2006/0064120 A1 | 3/2006 | Levine et al. |
| 2006/0155310 A1 | 7/2006 | Binmoeller |
| 2006/0155312 A1 | 7/2006 | Levine et al. |
| 2006/0155375 A1 | 7/2006 | Kagan et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0178691 A1 | 8/2006 | Binmoeller |
| 2006/0206063 A1 | 9/2006 | Kagan et al. |
| 2006/0206064 A1 | 9/2006 | Kagan et al. |
| 2006/0249165 A1 | 11/2006 | Silverman et al. |
| 2006/0258906 A1 | 11/2006 | Binmoeller |
| 2006/0265082 A1 | 11/2006 | Meade et al. |
| 2006/0282087 A1 | 12/2006 | Binmoeller |
| 2006/0293742 A1 | 12/2006 | Dann et al. |
| 2007/0004963 A1 | 1/2007 | Benchetrit |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0021761 A1 | 1/2007 | Phillips |
| 2007/0027548 A1 | 2/2007 | Levine et al. |
| 2007/0032702 A1 | 2/2007 | Ortiz |
| 2007/0032879 A1 | 2/2007 | Levine et al. |
| 2007/0038308 A1 | 2/2007 | Geitz |
| 2007/0060932 A1 | 3/2007 | Stack et al. |
| 2007/0078302 A1 | 4/2007 | Ortiz et al. |
| 2007/0083271 A1 | 4/2007 | Levine et al. |
| 2007/0100367 A1 | 5/2007 | Quijano et al. |
| 2007/0118158 A1 | 5/2007 | Deem et al. |
| 2007/0118159 A1 | 5/2007 | Deem et al. |
| 2007/0135825 A1 | 6/2007 | Binmoeller |
| 2007/0167963 A1 | 7/2007 | Deem et al. |
| 2007/0198074 A1 | 8/2007 | Dann et al. |
| 2007/0203517 A1 | 8/2007 | Williams et al. |
| 2007/0213740 A1 | 9/2007 | Deem et al. |
| 2007/0213748 A1 | 9/2007 | Deem et al. |
| 2007/0213751 A1 | 9/2007 | Scirica et al. |
| 2007/0213837 A1 | 9/2007 | Ferreri et al. |
| 2007/0219570 A1 | 9/2007 | Deem et al. |
| 2007/0239284 A1 | 10/2007 | Skerven et al. |
| 2007/0250083 A1 | 10/2007 | Deem et al. |
| 2007/0250132 A1 | 10/2007 | Burnett |
| 2007/0265709 A1 | 11/2007 | Rajan et al. |
| 2007/0276432 A1 | 11/2007 | Stack et al. |
| 2007/0282349 A1 | 12/2007 | Deem et al. |
| 2007/0282418 A1 | 12/2007 | Weitzner |
| 2007/0282452 A1 | 12/2007 | Weitzner et al. |
| 2007/0282453 A1 | 12/2007 | Weitzner et al. |
| 2007/0282454 A1 | 12/2007 | Krueger et al. |
| 2007/0293885 A1 | 12/2007 | Binmoeller |
| 2008/0033574 A1 | 2/2008 | Bessler et al. |
| 2008/0045803 A1 | 2/2008 | Williams et al. |
| 2008/0065122 A1 | 3/2008 | Stack et al. |
| 2008/0065136 A1 | 3/2008 | Young |
| 2008/0071383 A1 | 3/2008 | Levine et al. |
| 2008/0086214 A1 | 4/2008 | Hardin et al. |
| 2008/0092910 A1 | 4/2008 | Brooks |
| 2008/0097466 A1 | 4/2008 | Levine et al. |
| 2008/0103604 A1 | 5/2008 | Levine et al. |
| 2008/0109086 A1 | 5/2008 | Voegele et al. |
| 2008/0109087 A1 | 5/2008 | Durgin |
| 2008/0140172 A1 | 6/2008 | Carpenter et al. |
| 2008/0161935 A1 | 7/2008 | Albrecht et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2008/0167724 A1 | 7/2008 | Ruane et al. |
| 2008/0183238 A1 | 7/2008 | Chen |
| 2008/0195225 A1 | 8/2008 | Silverman et al. |
| 2008/0195226 A1 | 8/2008 | Williams et al. |
| 2008/0208135 A1 | 8/2008 | Annunziata |
| 2008/0208161 A1 | 8/2008 | Kaji et al. |
| 2008/0208224 A1 | 8/2008 | Surti et al. |
| 2008/0208239 A1 | 8/2008 | Annunziata |
| 2008/0208355 A1 | 8/2008 | Stack et al. |
| 2008/0208356 A1 | 8/2008 | Stack et al. |
| 2008/0208357 A1 | 8/2008 | Melanson et al. |
| 2008/0221597 A1 | 9/2008 | Wallace et al. |
| 2008/0221702 A1 | 9/2008 | Wallace et al. |
| 2008/0234834 A1 | 9/2008 | Meade et al. |
| 2008/0243151 A1 | 10/2008 | Binmoeller et al. |
| 2008/0249533 A1 | 10/2008 | Godin |
| 2008/0249566 A1 | 10/2008 | Harris et al. |
| 2008/0249635 A1 | 10/2008 | Weitzner et al. |
| 2008/0255476 A1 | 10/2008 | Boyajian et al. |
| 2008/0255587 A1 | 10/2008 | Cully et al. |
| 2008/0255594 A1 | 10/2008 | Cully et al. |
| 2008/0255678 A1 | 10/2008 | Cully et al. |
| 2008/0262529 A1 | 10/2008 | Jacques |
| 2008/0269715 A1 | 10/2008 | Faller et al. |
| 2008/0269797 A1 | 10/2008 | Stack et al. |
| 2008/0287969 A1 | 11/2008 | Tsonton et al. |
| 2008/0312559 A1 | 12/2008 | Santilli et al. |
| 2008/0319455 A1 | 12/2008 | Harris et al. |
| 2009/0005637 A1 | 1/2009 | Chin et al. |
| 2009/0012541 A1 | 1/2009 | Dahl et al. |
| 2009/0012542 A1 | 1/2009 | N'diaye et al. |
| 2009/0012544 A1 | 1/2009 | Thompson et al. |
| 2009/0012553 A1 | 1/2009 | Swain et al. |
| 2009/0076588 A1 | 3/2009 | Weber |

(56) References Cited

U.S. PATENT DOCUMENTS

| | | |
|---|---|---|
| 2009/0093767 A1 | 4/2009 | Kelleher |
| 2009/0093839 A1 | 4/2009 | Kelleher |
| 2009/0118749 A1 | 5/2009 | Shalon et al. |
| 2009/0125119 A1 | 5/2009 | Obermiller et al. |
| 2009/0138094 A1 | 5/2009 | Schurr |
| 2009/0149871 A9 | 6/2009 | Kagan et al. |
| 2009/0164028 A1 | 6/2009 | Chen |
| 2009/0177215 A1 | 7/2009 | Stack et al. |
| 2009/0182355 A1 | 7/2009 | Levine et al. |
| 2009/0187206 A1 | 7/2009 | Binmoeller et al. |
| 2009/0198210 A1 | 8/2009 | Burnett et al. |
| 2009/0216262 A1 | 8/2009 | Burnett et al. |
| 2009/0240105 A1 | 9/2009 | Smit et al. |
| 2009/0240340 A1* | 9/2009 | Levine et al. ............. 623/23.65 |
| 2009/0248171 A1 | 10/2009 | Levine et al. |
| 2009/0276055 A1 | 11/2009 | Harris et al. |
| 2009/0281379 A1 | 11/2009 | Binmoeller et al. |
| 2009/0299486 A1 | 12/2009 | Shohat et al. |
| 2009/0299487 A1 | 12/2009 | Stack et al. |
| 2009/0326433 A1 | 12/2009 | Albrecht et al. |
| 2009/0326675 A1 | 12/2009 | Albrecht et al. |
| 2010/0004755 A1 | 1/2010 | Imran |
| 2010/0016988 A1 | 1/2010 | Stack et al. |
| 2010/0030017 A1 | 2/2010 | Baker et al. |
| 2010/0135971 A1 | 6/2010 | Schiffrin |
| 2010/0256775 A1 | 10/2010 | Belhe et al. |
| 2010/0305590 A1 | 12/2010 | Holmes et al. |
| 2011/0009690 A1 | 1/2011 | Belhe et al. |
| 2011/0106273 A1 | 5/2011 | Belhe et al. |
| 2012/0065571 A1 | 3/2012 | Thompson et al. |
| 2012/0184893 A1 | 7/2012 | Thompson et al. |
| 2012/0253259 A1 | 10/2012 | Belhe et al. |
| 2012/0253260 A1 | 10/2012 | Belhe et al. |
| 2012/0302936 A1 | 11/2012 | Belhe et al. |
| 2014/0194806 A1 | 7/2014 | Belhe et al. |
| 2014/0200502 A1 | 7/2014 | Belhe et al. |
| 2014/0309576 A1 | 10/2014 | Belhe et al. |

FOREIGN PATENT DOCUMENTS

| | | |
|---|---|---|
| EP | 0137878 A1 | 4/1985 |
| EP | 1420730 A2 | 5/2004 |
| EP | 1492477 A1 | 1/2005 |
| EP | 1492478 A1 | 1/2005 |
| EP | 1555970 A1 | 7/2005 |
| EP | 1569582 A2 | 9/2005 |
| EP | 1585458 A1 | 10/2005 |
| EP | 1680054 A1 | 7/2006 |
| EP | 1708641 A1 | 10/2006 |
| EP | 1708655 A1 | 10/2006 |
| EP | 1709508 A2 | 10/2006 |
| EP | 1749482 A2 | 2/2007 |
| EP | 1750595 A2 | 2/2007 |
| EP | 1778069 A1 | 5/2007 |
| EP | 1786310 A2 | 5/2007 |
| EP | 1799145 A1 | 6/2007 |
| EP | 1817072 A2 | 8/2007 |
| EP | 1832250 A1 | 9/2007 |
| EP | 1850811 A1 | 11/2007 |
| EP | 1850812 A1 | 11/2007 |
| EP | 1881781 A2 | 1/2008 |
| EP | 1887995 A2 | 2/2008 |
| EP | 1895887 A2 | 3/2008 |
| EP | 1937164 A1 | 7/2008 |
| EP | 1992314 A1 | 11/2008 |
| EP | 1416861 B1 | 12/2008 |
| EP | 1749480 B1 | 12/2008 |
| EP | 2010270 A2 | 1/2009 |
| EP | 1610720 B1 | 2/2009 |
| EP | 2023828 A2 | 2/2009 |
| EP | 2026713 A2 | 2/2009 |
| EP | 2061397 A1 | 5/2009 |
| EP | 2066243 A1 | 6/2009 |
| EP | 2068719 A2 | 6/2009 |
| EP | 2080242 A2 | 7/2009 |
| EP | 1520528 B1 | 9/2009 |
| EP | 1610719 B1 | 1/2010 |
| EP | 1603488 B1 | 4/2010 |
| EP | 1585460 B1 | 5/2010 |
| EP | 1933721 B1 | 5/2010 |
| EP | 1768618 B1 | 4/2011 |
| EP | 1883370 B1 | 8/2011 |
| WO | WO9849943 A2 | 11/1998 |
| WO | WO02096327 A2 | 12/2002 |
| WO | WO03017882 A2 | 3/2003 |
| WO | WO03086246 A1 | 10/2003 |
| WO | WO03086247 A1 | 10/2003 |
| WO | WO03094785 A1 | 11/2003 |
| WO | WO2004011085 A1 | 2/2004 |
| WO | WO2004017863 A2 | 3/2004 |
| WO | WO2004041133 A1 | 5/2004 |
| WO | WO2004064680 A1 | 8/2004 |
| WO | WO2004064685 A1 | 8/2004 |
| WO | WO2004087014 A2 | 10/2004 |
| WO | WO2004087233 A2 | 10/2004 |
| WO | WO2004049982 B1 | 12/2004 |
| WO | WO2005037152 A1 | 4/2005 |
| WO | WO2005058415 A2 | 6/2005 |
| WO | WO2005060869 A2 | 7/2005 |
| WO | WO2005060882 A1 | 7/2005 |
| WO | WO2005065412 A2 | 7/2005 |
| WO | WO2005097012 A2 | 10/2005 |
| WO | WO2005099591 A2 | 10/2005 |
| WO | WO2005110244 A1 | 11/2005 |
| WO | WO2005110280 A2 | 11/2005 |
| WO | WO2005112822 A1 | 12/2005 |
| WO | WO2005120363 A1 | 12/2005 |
| WO | WO2006014496 A2 | 2/2006 |
| WO | WO2006016894 A1 | 2/2006 |
| WO | WO2006020370 A2 | 2/2006 |
| WO | WO2006028898 A2 | 3/2006 |
| WO | WO2006034062 A1 | 3/2006 |
| WO | WO2006060049 A2 | 6/2006 |
| WO | WO2006062996 A2 | 6/2006 |
| WO | WO2006078781 A1 | 7/2006 |
| WO | WO2006078927 A1 | 7/2006 |
| WO | WO2006102012 A1 | 9/2006 |
| WO | WO2006102240 A2 | 9/2006 |
| WO | WO2006124880 A2 | 11/2006 |
| WO | WO2006127593 A2 | 11/2006 |
| WO | WO2006133311 A2 | 12/2006 |
| WO | WO2007019117 A1 | 2/2007 |
| WO | WO2007030829 A2 | 3/2007 |
| WO | WO2007038715 A1 | 4/2007 |
| WO | WO2007041598 A1 | 4/2007 |
| WO | WO2007075396 A2 | 7/2007 |
| WO | WO2007092390 A2 | 8/2007 |
| WO | WO2007107990 A2 | 9/2007 |
| WO | WO2007127209 A2 | 11/2007 |
| WO | WO2007136468 A2 | 11/2007 |
| WO | WO2007139920 A2 | 12/2007 |
| WO | WO2007142829 A1 | 12/2007 |
| WO | WO2007142832 A1 | 12/2007 |
| WO | WO2007142833 A1 | 12/2007 |
| WO | WO2007142834 A1 | 12/2007 |
| WO | WO2007145684 A2 | 12/2007 |
| WO | WO2008005510 A2 | 1/2008 |
| WO | WO2008030403 A1 | 3/2008 |
| WO | WO2008033409 A1 | 3/2008 |
| WO | WO2008033474 A2 | 3/2008 |
| WO | WO2008039800 A2 | 4/2008 |
| WO | WO2008101048 A2 | 8/2008 |
| WO | WO2008106041 A1 | 9/2008 |
| WO | WO2008106279 A1 | 9/2008 |
| WO | WO2008112942 A2 | 9/2008 |
| WO | WO2008127552 A2 | 10/2008 |
| WO | WO2008141288 A1 | 11/2008 |
| WO | WO2008148047 A2 | 12/2008 |
| WO | WO2008150905 A1 | 12/2008 |
| WO | WO2008154450 A1 | 12/2008 |
| WO | WO2008154594 A2 | 12/2008 |
| WO | WO2009011881 A1 | 1/2009 |
| WO | WO2009011882 A2 | 1/2009 |

(56) References Cited

FOREIGN PATENT DOCUMENTS

| WO | WO2009012335 A1 | 1/2009 |
|---|---|---|
| WO | WO2009036244 A1 | 3/2009 |
| WO | WO2009046126 A1 | 4/2009 |
| WO | WO2009082710 A1 | 7/2009 |
| WO | WO2009085107 A1 | 7/2009 |
| WO | WO2009086549 A1 | 7/2009 |
| WO | WO2009097582 A1 | 8/2009 |
| WO | WO2009097585 A1 | 8/2009 |
| WO | WO2010115011 A1 | 10/2010 |
| WO | WO2011062882 A1 | 5/2011 |
| WO | WO2011073970 A1 | 6/2011 |
| WO | WO2011099940 A8 | 8/2011 |
| WO | WO2012103531 A2 | 8/2012 |

OTHER PUBLICATIONS

Schouten, Ruben et al., "A Multicenter, Randomized Efficacy Study of the endoBarrier Gastrointestinal Liner for Presurgical Weight Loss Prior to Bariatric Surgery", Annals of Surgery, vol. 251, No. 2, Feb. 2010, pp. 236-243.

Buchwald, Henry et al., "Bariatric Surgery: A Systematic Review and Meta-Analysis", JAMA, Oct. 13, 2004, 292 (14), pp. 1724-1737.

Cummings, David E. et al., "Role of the bypassed proximal intestine in the anti-diabetic effects of bariatric surgery", Surgery for Obesity and Related Diseases 3 2007, pp. 109-115.

International Search Report and Written Opinion issued in PCT/US12/58202, mailed Jan. 23, 2013, 14 pages.

International Search Report and Written Opinion issued in PCT/US2010/029648, mailed Aug. 24, 2010.

International Search Report and Written Opinion issued in PCT/US2010/041574, mailed Jan. 25, 2011.

International Search Report and Written Opinion issued in PCT/US2011/020560, mailed Mar. 28, 2011, 10 pages.

International Search Report and Written Opinion issued in PCT/US2011/061193.

International Search Report and Written Opinion issued in PCT/US2012/023048, mailed Jun. 22, 2012.

Invitation to Pay Additional Fees issued in PCT/US2010/029648, mailed Jun. 1, 2010.

Pories, Walter J. et al., "Surgical Treatment of Obesity and its Effect on Diabetes: 10-6 Follow-up", Am J Clin Nutr 1992, 55, 582S-585S.

Pories, Walter J. et al., "Who Would Have Thought It? An Operation Proves to be the Most Effective Therapy for Adult-Onset Diabetes Mellitus", Annals of Survery, Sep. 1995, 222(3), pp. 339-352.

Rodriguez-Grunert, Leonardo et al., "First Human Experience With endoscopically Delivered and retrieved duodenal-jejunal bypass sleeve", Surgery for Obesity and Related diseases 4 (2008) 55-59.

Rubino, Francesco et al,, "Effect of Duodenal-Jejunal Exclusion in a Non-Obese Animal Model of Type 2 Diabetes", Annals of Surgery, vol. 239, No. 1, Jan. 2004, pp. 1-11.

Rubino, Francesco et al., "Potential of Surgery for Curing Type 2 Diabetes Mellitus", Annals of Surgery, Nov. 2002, 236(5), 554-559.

Rubino, Francesco et al., "The Mechanism of Diabetes Control After Gastrointestinal Bypass Surgery Reveals a Role of the Proximal Small Intestine in the pathophysiology of Type 2 Diabetes", Annals of Surgery, 244(5), Nov. 2006, pp. 741-749.

Strader, April et al., "Weight Loss Through Ileal transposition is accompanied by increased ileal hormone secretion and synthesis in rats", Am J Physiol Endocrinol Metab 288: E447-E453, 2005.

Troy, Stephanie et al., "Intestinal Gluconeogenesis is a key factor for early metabolic changes after gastric bypass but not after gastric lap-band in mice", Cell metabolism 8, 201-211, Sep. 3, 2008.

Vetter, Marion et al., "Narrative Review: Effect of bariatric Surgery on Type 2 Diabetes Mellitus", Annals of Internal Medicine, Jan. 20, 2009, 150(2), pp. 94-104.

Daniels, Stephen, "Probiotics may 'counter obesity and diabetes': NIH study", Jul. 10, 2013, downloaded from http://www.nutraingredients-usa.com/research/probiotics-may-counter-obesity-and-diabetes-NIH-study, 2 pp.

Ley, Ruth E. et al., "Microbial ecology: human gut microbes associated with obesity", Nature, vol. 44, No. 7122, pp. 1022-1023, 2006.

Yadav, Hariom et al., Beneficial Metabolic Effects of a Probiotic via Butyrate-induced GLP-1 Hormone Secretion, Journal of Biological Chemistry, 2013, vol. 288, pp. 25088-25097.

\* cited by examiner

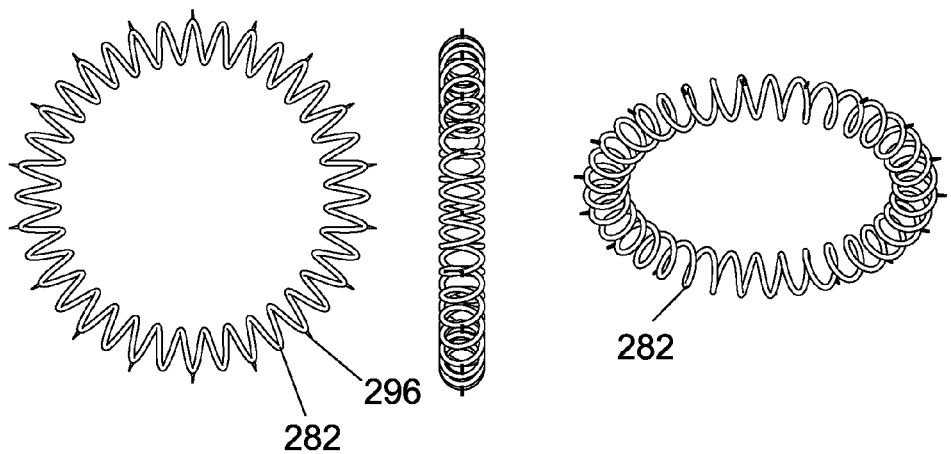
FIG 13A
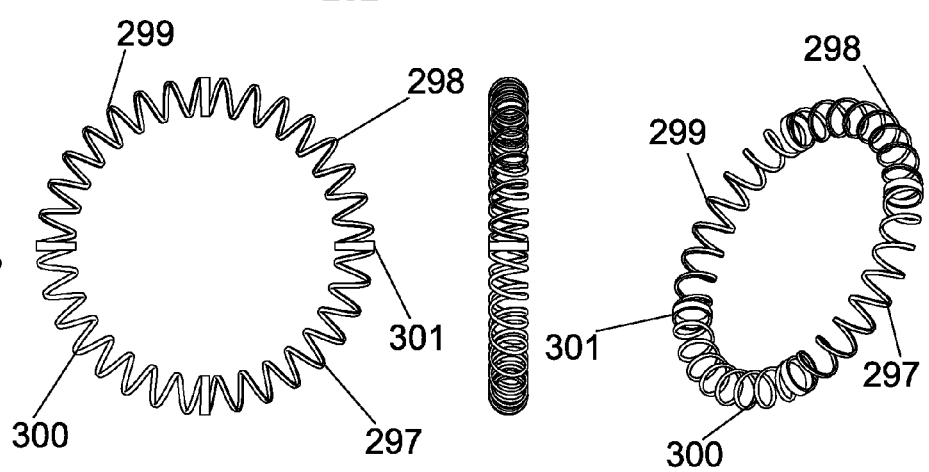
FIG 13B
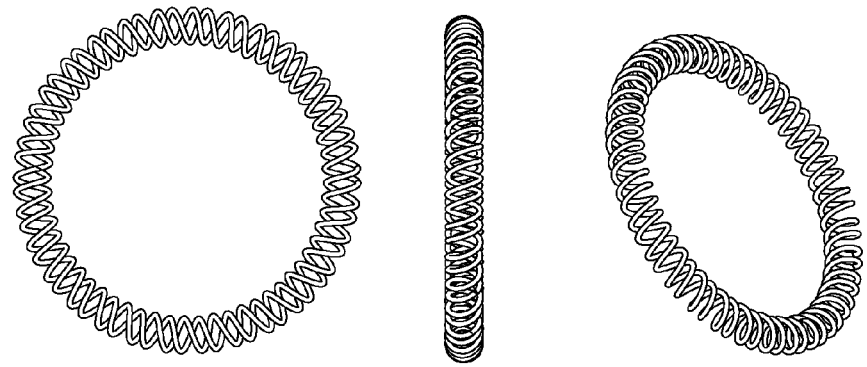
FIG 13C
FIG. 13

DELIVERY DEVICES AND METHODS FOR GASTROINTESTINAL IMPLANTS

CROSS-REFERENCE TO RELATED APPLICATION

This application claims the benefit under 35 U.S.C. section 119(e) of U.S. provisional patent application 61/626,658, filed Sep. 30, 2011. This application is a continuation-in-part of each of the following applications, each of which are hereby incorporated by reference in their entirety: (1) U.S. patent application Ser. No. 13/493,144, filed Jun. 11, 2012, which is a divisional of U.S. patent application Ser. No. 12/752,697, filed Apr. 1, 2010, which claims the benefit of U.S. provisional patent application 61/211,853, filed Apr. 3, 2009 (now granted as U.S. Pat. No. 8,211,186); (2) U.S. patent application Ser. No. 12/833,605, filed Jul. 9, 2010, which claims the benefit of U.S. provisional patent application 61/270,588, filed Jul. 10, 2009; (3) U.S. patent application Ser. No. 12/986,268, filed Jan. 7, 2011, which claims the benefit of U.S. provisional patent application 61/335,472, filed Jan. 7, 2010; (4) U.S. patent application Ser. No. 13/298,867, filed Nov. 17, 2011, which claims the benefit of U.S. provisional patent application 61/458,060, filed Nov. 17, 2010; and (5) U.S. patent application Ser. No. 13/360,689, filed Jan. 28, 2012, which claims the benefit of U.S. provisional patent application 61/462,156, filed Jan. 28, 2011, and U.S. provisional patent application 61/519,507, filed May 24, 2011.

TECHNICAL FIELD

This invention generally relates to implants placed within gastrointestinal systems, including the esophagus, the stomach and the intestines. In particular it relates to implant systems having components implantable and removable using endoscopic techniques for treatment of obesity, diabetes, reflux, gastroparesis and other gastrointestinal conditions.

BACKGROUND

Bariatric surgery procedures, such a sleeve gastrectomy, the Rouen-Y gastric bypass (RYGB) and the bileo-pancreatic diversion (BPD), modify food intake and/or absorption within the gastrointestinal system to effect weight loss in obese patients. These procedures affect metabolic processes within the gastrointestinal system, by either short circuiting certain natural pathways or creating different interaction between the consumed food, the digestive tract, its secretions and the neuro-hormonal system regulating food intake and metabolism. In the last few years there has been a growing clinical consensus that obese patients who undergo bariatric surgery see a remarkable resolution of their type-2 Diabetes Mellitus (T2DM) soon after the procedure. The remarkable resolution of diabetes after RYGB and BPD typically occurs too fast to be accounted for by weight loss alone, suggesting there may be a direct impact on glucose homeostasis. The mechanism of this resolution of T2DM is not well understood, and it is quite likely that multiple mechanisms are involved.

One of the drawbacks of bariatric surgical procedures is that they require fairly invasive surgery with potentially serious complications and long patient recovery periods. In recent years, there is an increasing amount of ongoing effort to develop minimally invasive procedures to mimic the effects of bariatric surgery using minimally invasive procedures. One such procedure involves the use of gastrointestinal implants that modify transport and absorption of food and organ secretions. For example, U.S. Pat. No. 7,476,256 describes an implant having a tubular sleeve with anchoring barbs, which offer the physician limited flexibility and are not readily removable or replaceable. Moreover, stents with active fixation means, such as barbs that deeply penetrate into surrounding tissue, may potentially cause tissue necrosis and erosion of the implants through the tissue, which can lead to complications, such as bacterial infection of the mucosal tissue or systemic infection. Also, due to the intermittent peristaltic motion within the digestive tract, implants such as stents have a tendency to migrate.

Gastroparesis is a chronic, symptomatic disorder of the stomach that is characterized by delayed gastric emptying in the absence of mechanical obstruction. The cause of gastroparesis is unknown, but it may be caused by a disruption of nerve signals to the intestine. The three most common etiologies are diabetes mellitus, idiopathic, and postsurgical. Other causes include medication, Parkinson's disease, collagen vascular disorders, thyroid dysfunction, liver disease, chronic renal insufficiency, and intestinal pseudo-obstruction. The prevalence of diabetic gastroparesis (DGP) appears to be higher in women than in men, for unknown reasons.

Diabetic gastroparesis affects about 40% of patients with type-1 diabetes and up to 30% of patients with type-2 diabetes and especially impacts those with long-standing disease. Both symptomatic and asymptomatic DGP seem to be associated with poor glycemic control by causing a mismatch between the action of insulin (or an oral hypo-glycemic drug) and the absorption of nutrients. Treatment of gastroparesis depends on the severity of the symptoms.

Several inventors have recently described intra-luminal implants and implant delivery tools to mimic the effect of bariatric surgery procedures such as gastric and intestinal bypass for the treatment of obesity. In particular to mimic the effects of a popular surgical procedure called the Rouen-Y Gastric bypass in which most of the stomach is excised and a lower part of the small intestine is anastamosed to a small stomach pouch, several inventors have proposed implants that anchor at the gastroesophageal junction and reroute food to the small intestine. In many instances these implants then also anchor sleeves or stented sleeves that act as bypass conduits for mimicking stomach and intestinal bypass surgeries.

These systems, however, have significant shortcomings in terms of clinical side effects and complications. Implants that bypass the stomach with artificial sleeve like structures or conduits do not have motility like in a surgical gastric bypass where the anastomosed section of the intestine actively propels food from the esophagus (e.g., the system described in U.S. Pat. No. 7,837,669). Hence in early clinical results using this approach patients have complained about dysphagia (difficulty swallowing) as the solid undigested food is not easily pushed forward in to the small intestine from the esophagus through these artificial passageways. Also, the delivery system contemplated to be used to perform this procedure is complicated (e.g., U.S. Patent Publication 2008/0167606). It involves placing a sleeve element into the small intestine, where the sleeve element is first delivered in a sock-like configuration and then is extended into the small intestine by unrolling it. Accurate placement with this system is difficult.

SUMMARY

According to various embodiments, the present invention provides for an apparatus and method to place and anchor an intestinal bypass sleeve within one or more of the pyloric antrum, the pylorus, the duodenum and the jejunum. The gastrointestinal implant herein disclosed can be inserted endoscopically (when the device is loaded into a delivery catheter) through the mouth, throat, stomach and intestines. The gastrointestinal implant device includes a flexible thin-walled sleeve and an expandable anchor attached to the proximal end of the sleeve; secondary anchors may also anchor other portions of the thin-walled sleeve.

The present invention herein disclosed (with a short bypass sleeve or no bypass sleeve) can also be used to hold open the pylorus and may help to reduce the symptoms of gastroparesis, by allowing the stomach contents to exit the stomach easier through the pylorus into the duodenum. An active pumping means may also be attached to the expandable anchor to actively pump the stomach contents from the pyloric antrum into the duodenum.

According to various embodiments, the delivery system includes a thin sleeve element having a proximal anchoring element attached to it and distal end that is open. A single or multi-lumen sleeve delivery catheter carries the sleeve element by being releasably attached to its distal end, but the delivery catheter does not pass through the lumen of the sleeve. A multi-lumen implant delivery catheter with a distal end in the form of a capsule that can accommodate the anchoring implant within its bore. A mechanical retention feature releasably attaches the distal end of the sleeve element to the distal end of the catheter.

According to various embodiments, a method of using this delivery system to deliver an implant for creating an intestinal bypass includes (1) introducing an endoscope within the stomach, (2) placing a guide wire through the lumen of the endoscope and placing it past the pylorus in to the small intestine under endoscopic and or fluoroscopic guidance, (3) withdrawing the endoscope out the patient, (4) placing the implant delivery catheter system that is pre-loaded with a sleeve delivery catheter and the sleeve element (including the proximal anchoring element) over the guide-wire in to the stomach, (5) advancing the sleeve delivery catheter which extends beyond the implant delivery catheter with the sleeve in to the small intestine so that its distal end is at the position where you want to locate the distal end of the sleeve and the capsule is correctly positioned at the pylorus under endoscopic and/or fluoroscopic guidance, (6) reintroducing the endoscope in to the stomach adjacent to the capsule at the distal end of the implant delivery catheter, (7) releasing the distal end of the sleeve by activating a release mechanism, (8) retracting the sleeve delivery catheter and the guide wire to a position proximal to the capsule, (9) deploying the intestinal side of the anchoring element with an actuator carried in one of the lumens in the implant delivery catheter, (10) deploying the stomach side of the anchoring element either with an actuator carried in one of the lumens in the implant delivery catheter or by retracting the entire implant delivery system backwards towards the mouth of the patient, and (11) withdrawing the endoscope, the guide wire and the implant delivery system out of the patient.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 13 is a drawing of alternative embodiments of toroidally wound springs.

Figure 1:
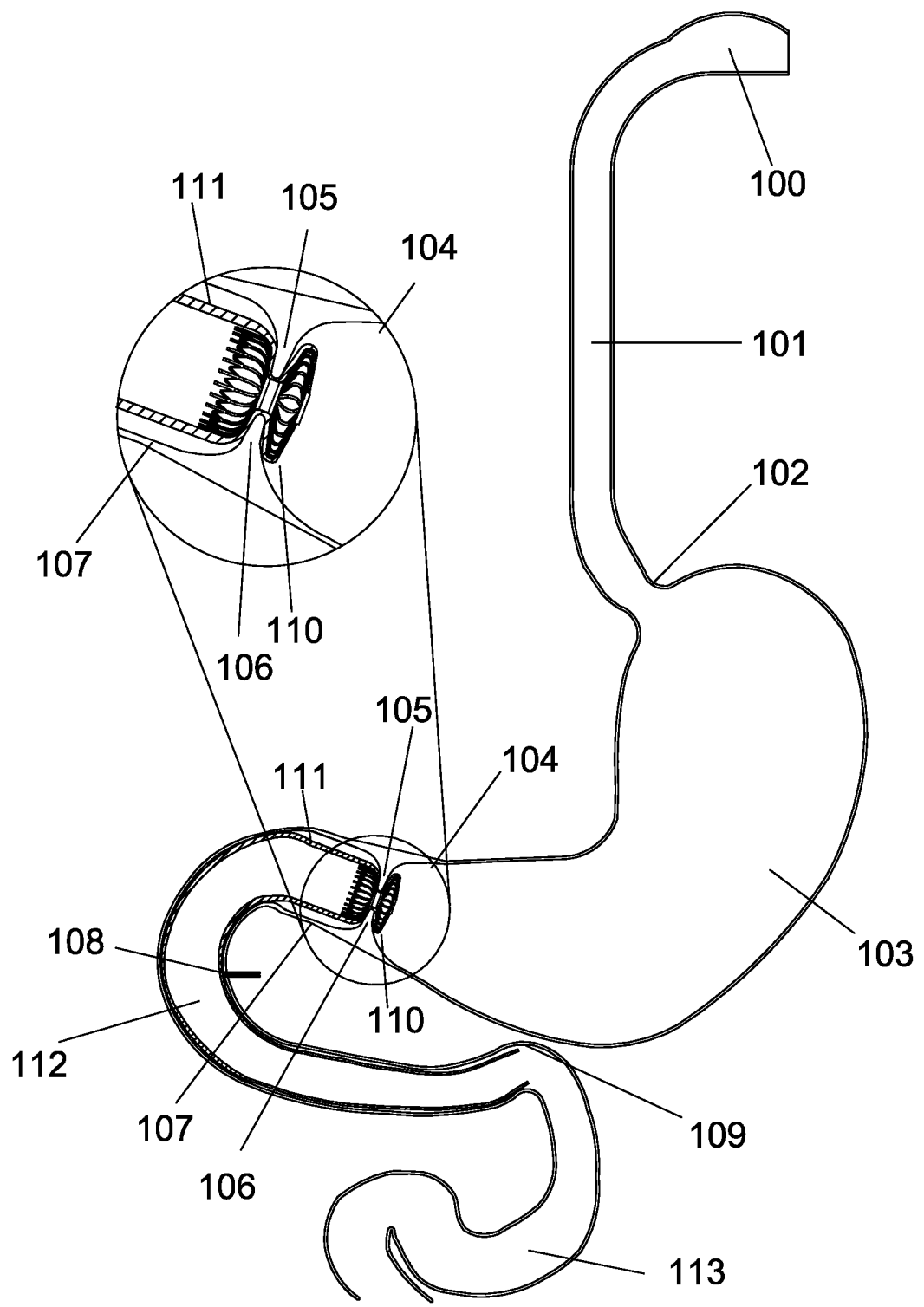
FIG. 1 is a cross-sectional view of a portion of the digestive tract in a human body with an intestinal bypass sleeve implanted in the duodenum from the pylorus to the ligament of Treitz. The sleeve is held in place at the pylorus by an expandable anchor that anchors on the pylorus.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a sectional view of an embodiment of the invention implanted in a portion of a human digestive tract. As a person ingests food, the food enters the mouth 100, is chewed, and then proceeds down the esophagus 101 to the lower esophageal sphincter at the gastroesophageal junction 102 and into the stomach 103. The food mixes with enzymes in the mouth 100 and in the stomach 103. The stomach 103 converts the food to a semi-fluid substance called chyme. The chyme enters the pyloric antrum 104 and exits the stomach 103 through the pylorus 106 and pyloric orifice 105. The small intestine is about 21 feet long in adults. The small intestine is comprised of three sections: the duodenum 112, jejunum 113 and ileum (not shown). The duodenum 112 is the first portion of the small intestine and is typically 10-12 inches long. The duodenum 112 is comprised of four sections: the superior, descending, horizontal and ascending. The duodenum 112 ends at the ligament of Treitz 109. The papilla of Vater 108 is the duct that delivers bile and pancreatic enzymes to the duodenum 112. The duodenal bulb 107 is the portion of the duodenum which is closest to the stomach 103. As shown, an intestinal bypass sleeve 111 is implanted in the duodenum from the pyloric antrum 104 and pylorus 106 to the ligament of Treitz 109. The intestinal bypass sleeve 111 is held in place at the pylorus 106 by an expandable anchor 110 that anchors on the pylorus 106.

In various exemplary embodiments, the sleeve 111 is integrally formed with or coupled to the expandable anchor 110. According to other exemplary embodiments, the sleeve 111 is removably or releasably coupled to the expandable anchor 110. According to various embodiments, the bypass sleeve has a diameter of between about 10 mm and about 35 mm. According to various embodiments, the bypass sleeve has a thickness of between about 0.001 and about 0.015 inches. Exemplary structures for removably or releasably coupling or attaching the sleeve 111 to the expandable anchor 110 are disclosed for example in U.S. patent application Ser. No. 12/752,697, filed Apr. 1, 2010, entitled "Modular Gastrointestinal Prostheses," which is incorporated herein by reference. According to various embodiments, the sleeve 111 or the expandable anchor 110 (or both) are further coupled at the pylorus 106 using one or more of the techniques described in either of U.S. patent application Ser. No. 12/752,697 or U.S. patent application Ser. No. 12/833,605, filed Jul. 9, 2010, entitled "External Anchoring Configuration for Modular Gastrointestinal Prostheses," both of which are incorporated herein by reference. According to various embodiments of the invention, the sleeve 111 may be configured and coupled to the expandable anchor 110, using one or more of the configurations disclosed in U.S. patent application Ser. No. 12/986, 268, filed Jan. 7, 2011, entitled "Gastrointestinal Prostheses Having Partial Bypass Configurations," which is incorporated herein by reference.

Figure 2:
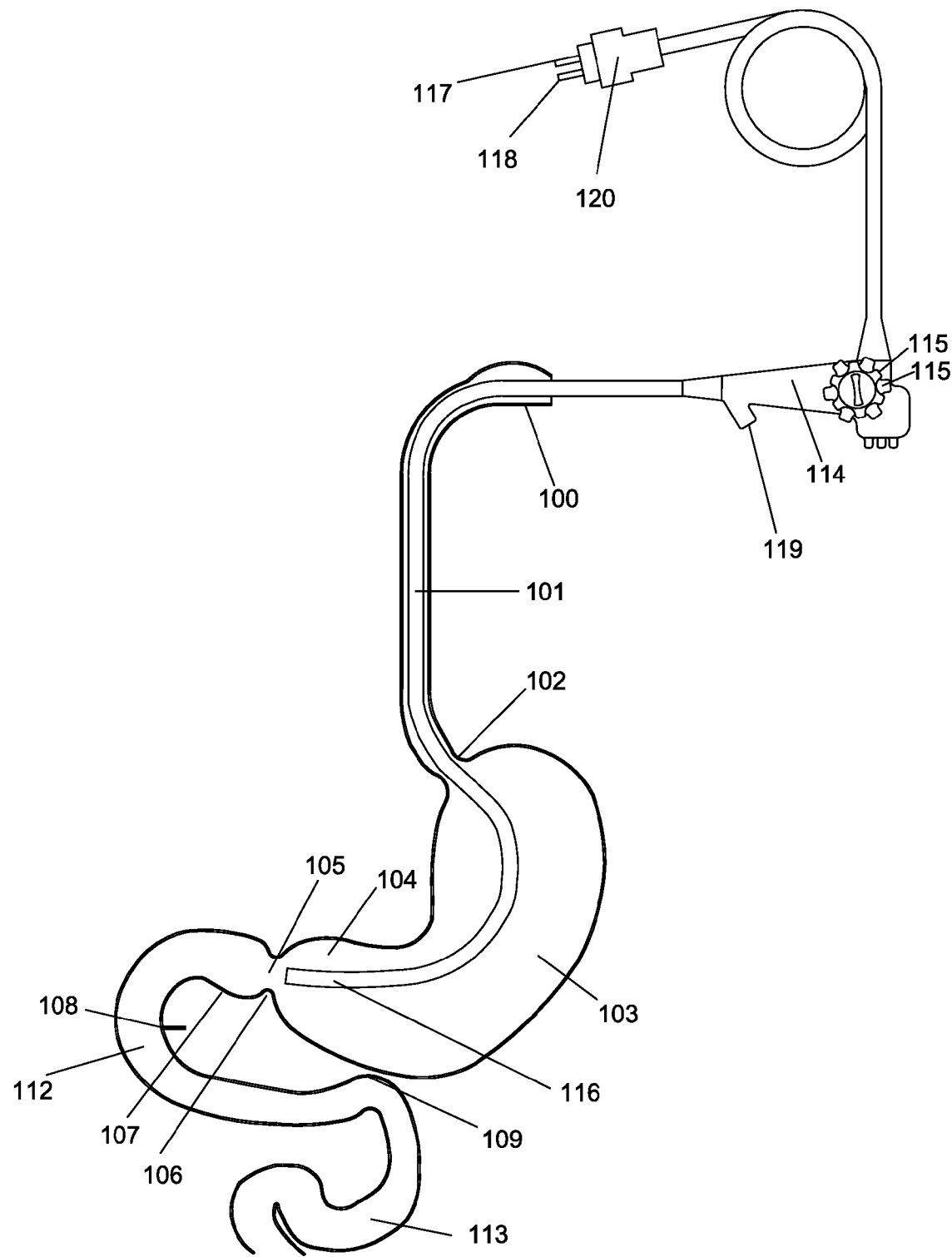
FIG. 2 is a cross-sectional view of a portion of the digestive tract in a human body with an endoscope inserted through the mouth, esophagus and stomach to the pylorus.

FIG. 2 is a sectional view of a portion of the digestive tract in a human body. As shown, an endoscope 114 has been inserted through: the mouth 100, esophagus 101, stomach 103 and pyloric antrum 104 to allow visualization of the pylorus 106. Endoscopes 114 are used for diagnostic and therapeutic procedures in the gastrointestinal tract. The typical endoscope 114 is steerable by turning two rotary dials 115 to cause deflection of the working end 116 of the endoscope. The working end of the endoscope or distal end 116, typically contains two fiber bundles for lighting 117, a fiber bundle for imaging 118 (viewing) and a working channel 119. The working channel 119 can also be accessed on the proximal end of the endoscope. The light fiber bundles and the image fiber bundles are plugged into a console at the plug in connector 120. The typical endoscope has a working channel in the 2.6 to 3.2 mm diameter range. The outside diameter is typically in the 8 to 12 mm diameter range depending on whether the endoscope is for diagnostic or therapeutic purposes.

Figure 3:
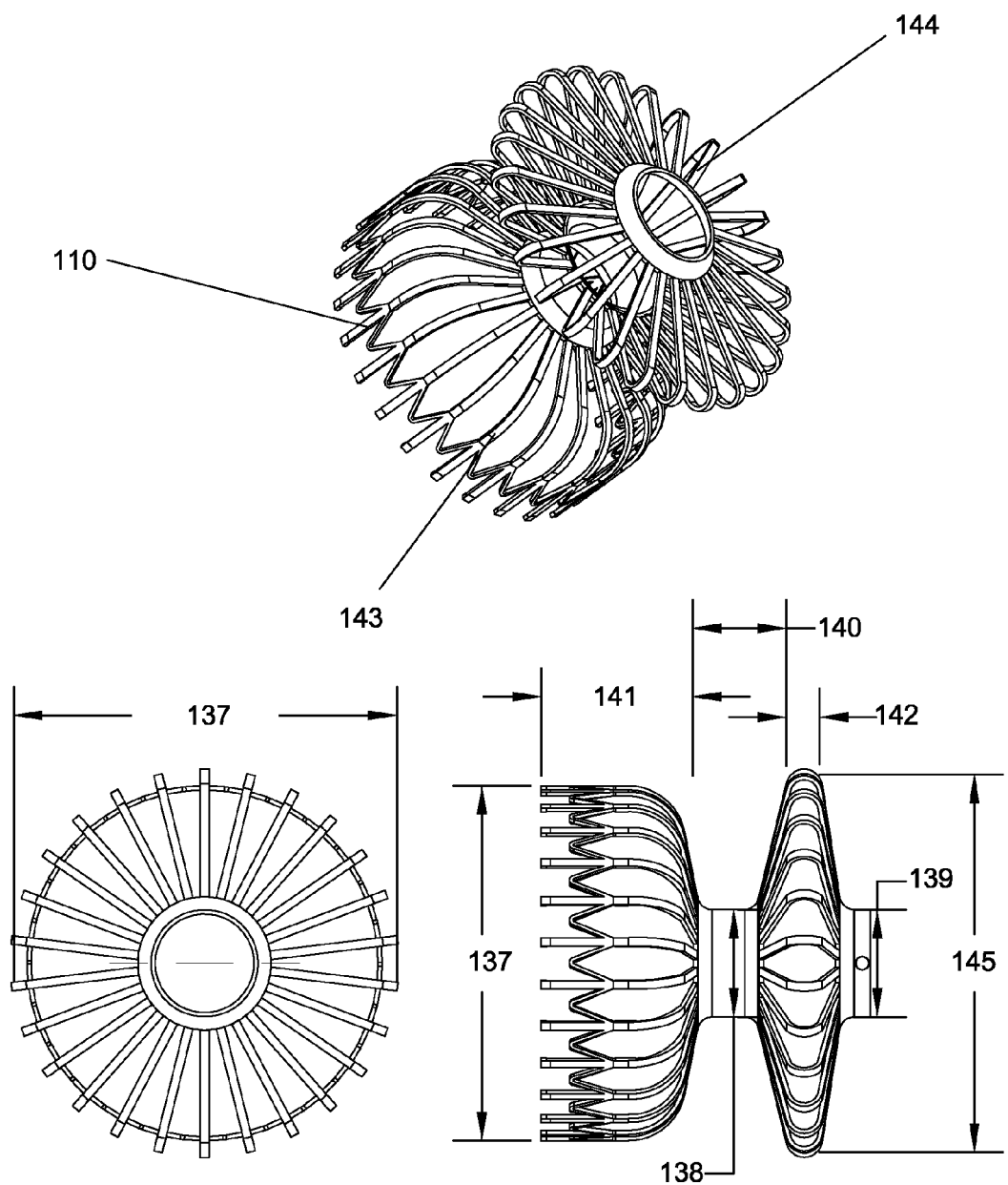
FIG. 3 is a drawing of an expandable anchor according to exemplary embodiments of the invention.

FIG. 3 is a drawing of an expandable anchor 110. The expandable anchor 110 provides for an anchoring means to hold an intestinal bypass sleeve 111 within the small intestine. In exemplary embodiments, the expandable anchor 110 is designed to allow the anchor to be of a self-expanding design. A self-expanding anchor design can be compressed in diameter to allow the device to be compressed in diameter to be loaded onto a delivery catheter. The anchor 110 can then recover elastically to the original starting diameter, with the anchor diameter decreasing only a small amount due to non-elastic recovery. The anchor 110 can also be made of a plastically deformable design and require a mechanical force applied to it in the radial or longitudinal direction to accomplish the expansion of the anchor. The mechanical force can be accomplished with an inflatable balloon type device, radially expanding the anchor 110, or it may also be accomplished by a longitudinal compression of the anchor 110 by a screw type mechanism or cable tensioning means. As shown, the anchor 110 has a proximal portion or proximal disk 144 that is comprised of 26 spring arms.

As shown, the anchor 110 has a distal portion (e.g., open-ended cylindrical portion) 143 that is comprised of 26 spring arms. According to various embodiments, the anchor 110 could have from 3 to 72 spring arms for the proximal disk and the open ended cylinder.

According to exemplary embodiments, the expandable anchor 110 is made from a nickel titanium alloys (Nitinol). Other alternative suitable alloys for manufacturing the anchor 110 are stainless steel alloys: 304, 316L, BioDur® 108 Alloy, Pyromet Alloy® CTX-909, Pyromet® Alloy CTX-3, Pyromet® Alloy 31, Pyromet® Alloy CTX-1, 21Cr-6Ni-9Mn Stainless, Pyromet® Alloy 350, 18Cr-2Ni-12Mn Stainless, Custom 630 (17Cr-4Ni) Stainless, Custom 465® Stainless, Custom 455® Stainless, Custom 450® Stainless, Carpenter 13-8 Stainless, Type 440C Stainless, cobalt chromium alloys—MP35N, Elgiloy, L605, Biodur® Carpenter CCM alloy, titanium and titanium alloys, Ti-6Al-4V/ELI and Ti-6Al-7Nb, Ti-15Mo, Tantalum, Tungsten and tungsten alloys, pure platinum, platinum-iridium alloys, platinum-nickel alloys, niobium, iridium, conichrome, gold and gold alloys. The anchor 110 may also be comprised of the following absorbable metals: pure iron and magnesium alloys. The anchor 110 may also be comprised of the following plastics: Polyetheretherketone (PEEK), polycarbonate, polyolefins, polyethylenes, polyether block amides (PEBAX), nylon 6, 6-6, 12, Polypropylene, polyesters, polyurethanes, polytetrafluoroethylene (PTFE) Poly(phenylene sulfide) (PPS), poly (butylene terephthalate) PBT, polysulfone, polyamide, polyimide, poly(p-phenylene oxide) PPO, acrylonitrile butadiene styrene (ABS), Polystyrene, Poly(methyl methacrylate) (PMMA), Polyoxymethylene (POM), Ethylene vinyl acetate, Styrene acrylonitrile resin, Polybutylene. The anchor 110 may also be comprised of the following absorbable polymeres: Polyglycolic acid (PGA), Polylactide (PLA), Poly(ϵ-caprolactone), Poly(dioxanone) Poly(lactide-co-glycolide).

The anchor 110, according to exemplary embodiments, is laser cut from a round tubing or from a flat sheet of Nitinol and then is rolled into a cylindrical shape after laser cutting. The anchor 110, according to exemplary embodiments, is made from a Nitinol tube of about 9 mm outside diameter by a wall thickness of 0.006 inch thick. Alternatively a starting tube outside diameter can range from about 2 mm to 16 mm. An alternative construction method is to laser cut or chemical etch the pattern from a flat sheet of Nitinol with a thickness of 0.002 inch to 0.020 inch.

According to various embodiment, anchor 110 has an inside diameter 139 in the range of about 2 mm to 20 mm. Anchor 110 has an expanded open end 137 in the range of about 12 mm to 60 mm. Anchor 110 has a disk-shaped feature 144 that has a diameter 145 in the range of about 12 mm to 60 mm. Anchor 110 has a central cylinder 138 that has an outside diameter in the range of 4 mm to 20 mm. Anchor 110 has a flange 141 adjacent to the large diameter open end that has a length of about 8 mm in length. According to various embodiments, this length 141 could range from a length of about 1 mm to 30 mm in length. Central cylinder section 138 can have a length 140 of about 1 mm to 30 mm and is close to the width of the pylorus 106. The proximal disk can have a length of 1 mm to 20 mm. The proximal disk 144 can alternatively be formed in the shape of a sphere. The central cylinder 138, in various embodiments, is made from a material having a stiffness sufficient to resist compressive forces applied by the pylorus.

Figure 4:
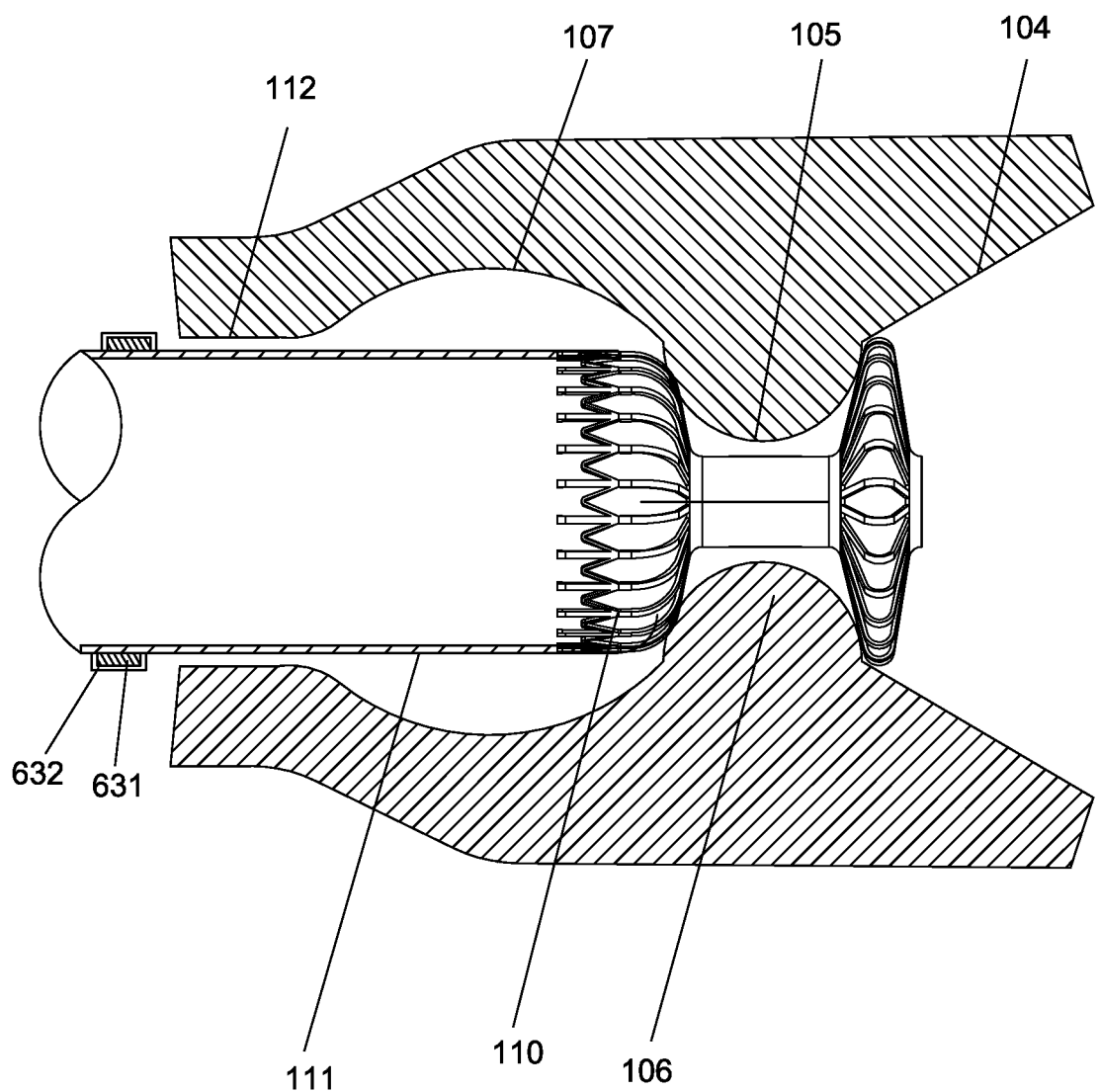
FIG. 4 is a cross-sectional drawing of the pyloric antrum, pylorus, duodenal bulb and duodenum. An expandable anchor and intestinal bypass sleeve is implanted into the pylorus.
Figure 16:
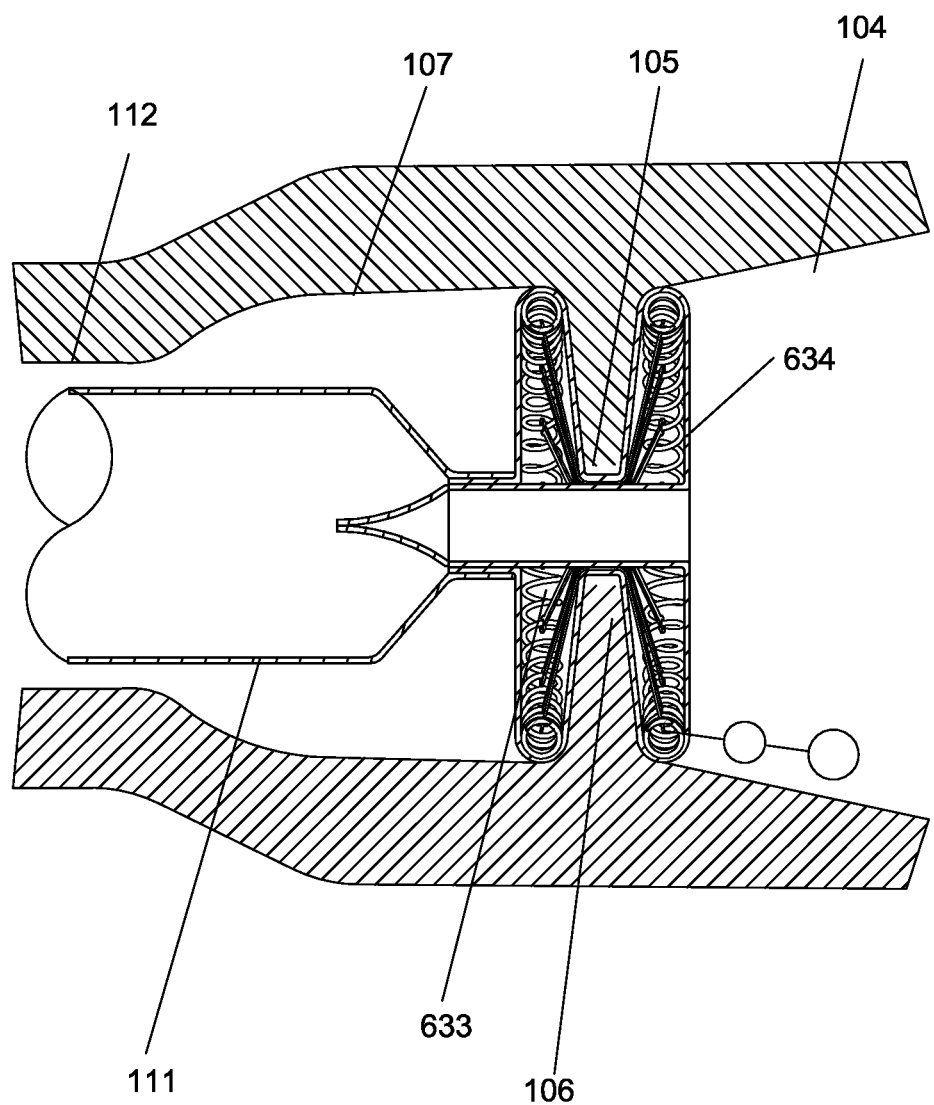
FIG. 16 is a sectional view of the expandable anchor as in FIG. 7 and intestinal bypass sleeve implanted across the pylorus.

FIG. 4 is a sectional view of the pyloric antrum 104, pyloric aperture 105, pylorus 106, duodenal bulb 107 and duodenum 112. An expandable anchor 110 and intestinal bypass sleeve 111 are implanted into the pylorus 106. The expandable anchor 110 is shown here without a covering material to allow for better visualization of the expandable anchor 110. In various exemplary embodiments, the expandable anchor 110 is not covered, while in other exemplary embodiments, it is covered with a polymer membrane made from a material such as silicone, flourosilicone elastomers such as Viton, polyurethane, PTFE (polytetrafluoroethylene), FEP (fluorinated ethylene propylene), polyethylene, ePTFE (expanded polytetrafluoroethylene), PFA (Perfluoroalkoxy), PVDF (Polyvinylidene Fluoride, Tetrafluoroethylene), THV (Hexafluoropropylene and Vinylidene Fluoride), ETFE (Ethylenetetrafluoroethylene), ECTFE (Chloro Trifluoro Ethylene/Ethylene Copolymer) EFEP (copolymer of ethylene, tetrafluoroethylene, and hexafluoropropylene), PVF (polyvinyl fluoride) or other suitable material. FIG. 16, for example, shows an embodiment of the expandable anchor 110 covered with a polymer film. The expandable anchor 110 can be made from metal or plastic. The intestinal bypass sleeve 111 can vary in length from 1-2 inches in length up to several feet. In some embodiments, the sleeve bypasses the length of the duodenum up to the ligament of Treitz. The sleeve can be longer and bypass into the jejunum. The intestinal bypass sleeve 111 may be made from a thin-walled polymer material such as silicone, flourosilicone elastomers such as Viton, polyurethane, PTFE (polytetrafluoroethylene), FEP (fluorinated ethylene propylene), polyethylene, expanded polytetrafluoroethylene (ePTFE), PFA (Perfluoroalkoxy), PVDF (Polyvinylidene Flouride, Tetrafluoroethylene), THV (Hexafluoropropylene and Vinylidene Fluoride), ETFE (Ethylenetetrafluoroethylene), ECTFE (Chloro Trifluoro Ethylene/Ethylene Copolymer) EFEP (copolymer of ethylene, tetrafluoroethylene, and hexafluoropropylene), PVF (polyvinyl fluoride) or other suitable material or combinations of the listed materials. In exemplary embodiments, the wall thickness of the intestinal bypass sleeve 111 may be in the range of 0.001 inch to 0.012 inch thick. The intestinal bypass sleeve 111 may be made by extrusion, into a tubular form or a lay flat tubing, dip coated from a liquid solution, powder coated from fine particles of polymer or paste extruded and then stretched as is the case with ePTFE.

Tantalum radiopaque markers 361 are attached to the intestinal bypass 111 by encapsulation in a polymer 362 such as FEP. The radiopaque markers 361 can be attached to the intestinal bypass sleeve at fixed increments along the length of the bypass sleeve 111 to allow visualization of the sleeve during deployment and at patient follow-up to confirm the position of the bypass sleeve. The radiopaque markers 361 can be made of disc of tantalum. A tantalum ball bearing or sphere can be flattened to provide such a disk.

Figure 5:
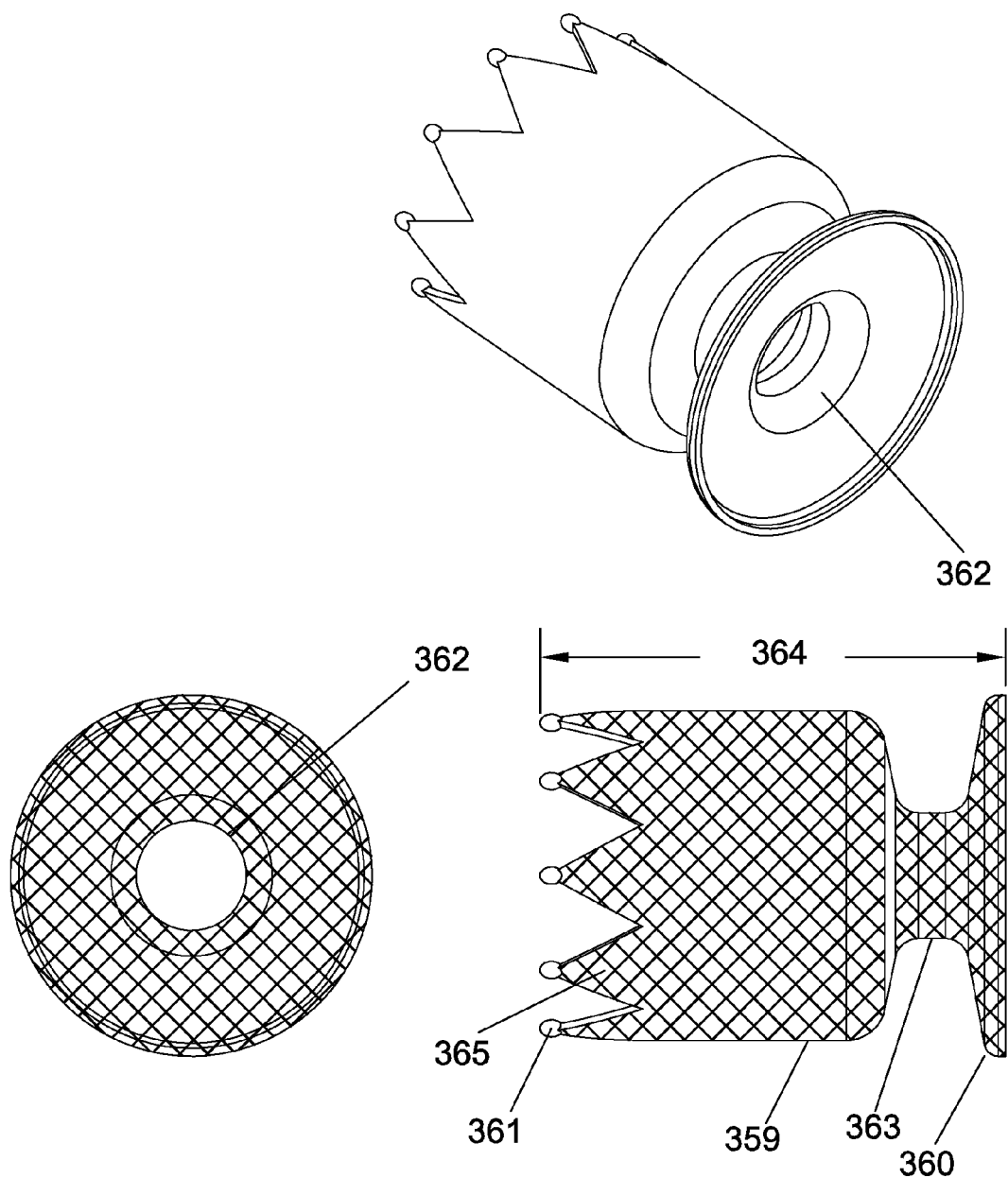
FIG. 5 is a drawing of an alternative embodiment of the invention herein disclosed. The expandable anchor is comprised of a hollow tubular braided structure of wire. The wire form has been shaped to conform to the shape of the pylorus and the duodenal bulb.

FIG. 5 is a drawing of an alternative embodiment of the invention herein disclosed. The expandable anchor is comprised of a hollow tubular braided structure of wire. The tubular braid can be braided in the diameter range from 10 mm in diameter up to about 70 mm in diameter. The wire diameter can range from 0.001 inch to 0.014 inch. In exemplary embodiments, the number of wire ends in the braid is 96 ends, but it can range from as few as 4 ends up to 256 ends. The wire can be made from a metal such as Nitinol, MP35N, L605, Elgiloy, stainless steel or from a plastic such as PET, PEEK or Delrin or other suitable material. The tubular wire braid is formed into a shape with a disk 360, a central cylinder portion 363 and a cylindrical portion 359. Wire ends are gathered into bunches 361 and welded together or a sleeve is crimped onto wires to keep the braided ends from fraying and unraveling. Alternatively, the structure could be made from a braid using a single wire end. Central cylinder 363 has a through lumen 362 that allows chyme to flow from the stomach to the duodenum. The central cylinder 363 can be rigid to hold the pylorus 106 open or it may be compliant to allow the opening and closure through lumen 362 with the pylorus 106.

The length 364 of the device is typically about 50 mm but can range from about 10 mm to 100 mm. The diameter of the cylindrical portion 359 is typically about 25 mm in diameter, but can range from 10 mm to 75 mm. The diameter of the central cylinder portion is typically about 10 mm in diameter but can range from 2 mm up to 25 mm in diameter. The length of the central cylinder 363 is approximately that of the width of the pylorus 106, but the central cylinder 363 can be slightly longer to provide a gap between central cylinder and pylorus or slightly shorter to provide for a compressive force to be applied to the pylorus. The expandable anchor is compressible in diameter and the diameter can be reduced to about 5 mm to 10 mm in diameter typically to allow the anchor to be loaded into a catheter. The expandable anchor can be covered on the outside and/or inside side with a polymer membrane covering. The membrane 365 covering the expandable anchor may be made from a thin-walled polymer material such as silicone, polyurethane, polytetrafluoroethylene (PTFE), fluorinated ethylene propylene, polyethylene, expanded polytetrafluoroethylene (ePTFE) or other suitable material. In some embodiments, the wall thickness of the membrane covering the expandable anchor may be in the range of 0.001 inch to 0.030 inch thick. The membrane 365 may be made by extrusion, dip coating from a liquid solution, powder coated from fine particles of polymer or paste extruded and then stretched as is the case with ePTFE. The expandable anchor membrane 365 may also be cut from a flat sheet of material such as ePTFE and then bonded or sewn into a disk shape or spherical shaped structure and then attached to the expandable anchor by sewing or gluing with a polymer such as FEP.

Figure 6:
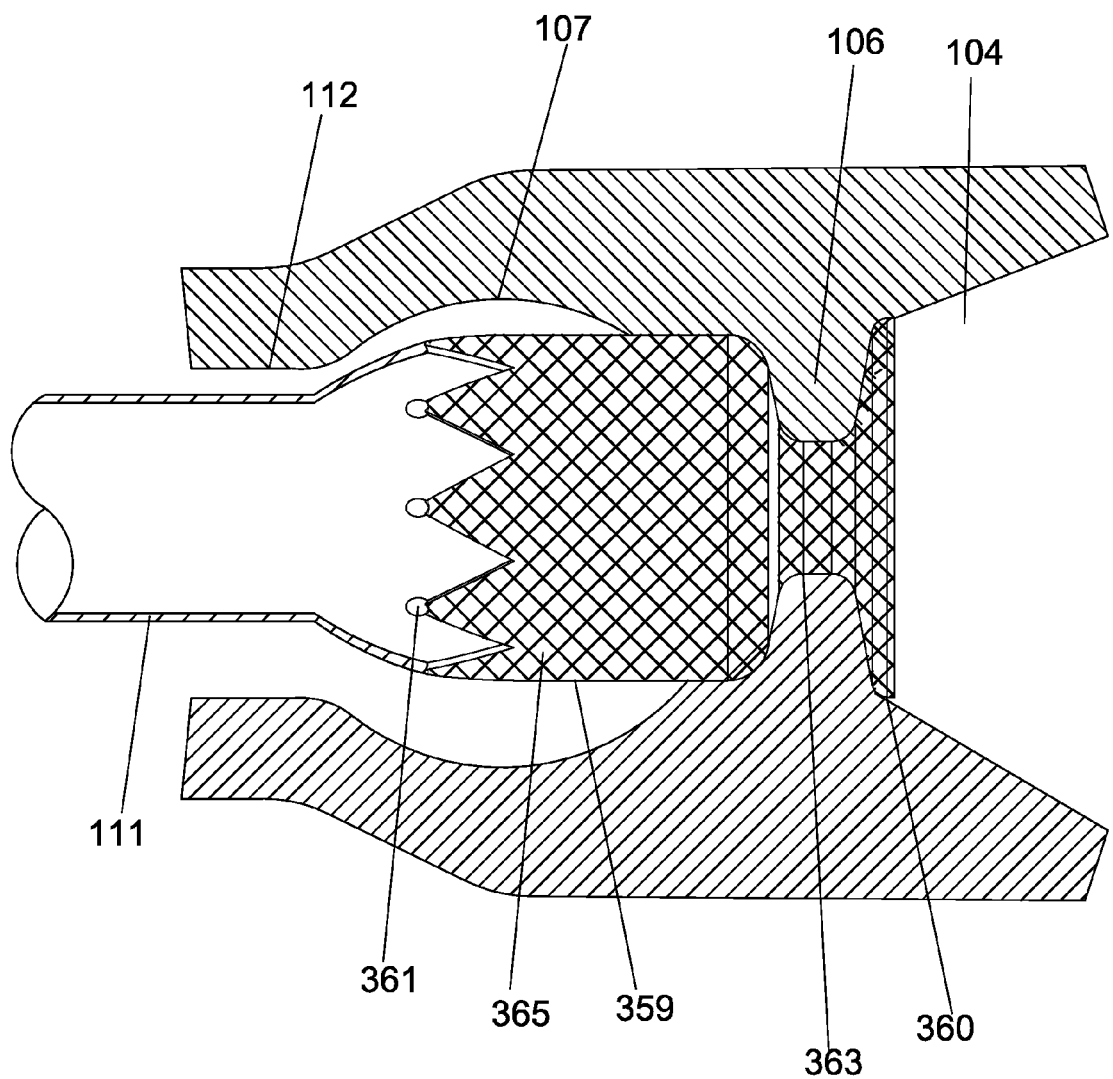
FIG. 6 is a sectional view of an alternative embodiment of an anchor and sleeve implanted into the pylorus and duodenal bulb and duodenum.

FIG. 6 is a sectional view of the invention herein disclosed in FIG. 5 implanted into the pyloric antrum 104, pylorus 106, duodenal bulb 107, and duodenum 112. An intestinal bypass sleeve 111 is attached to the anchor.

Figure 7:
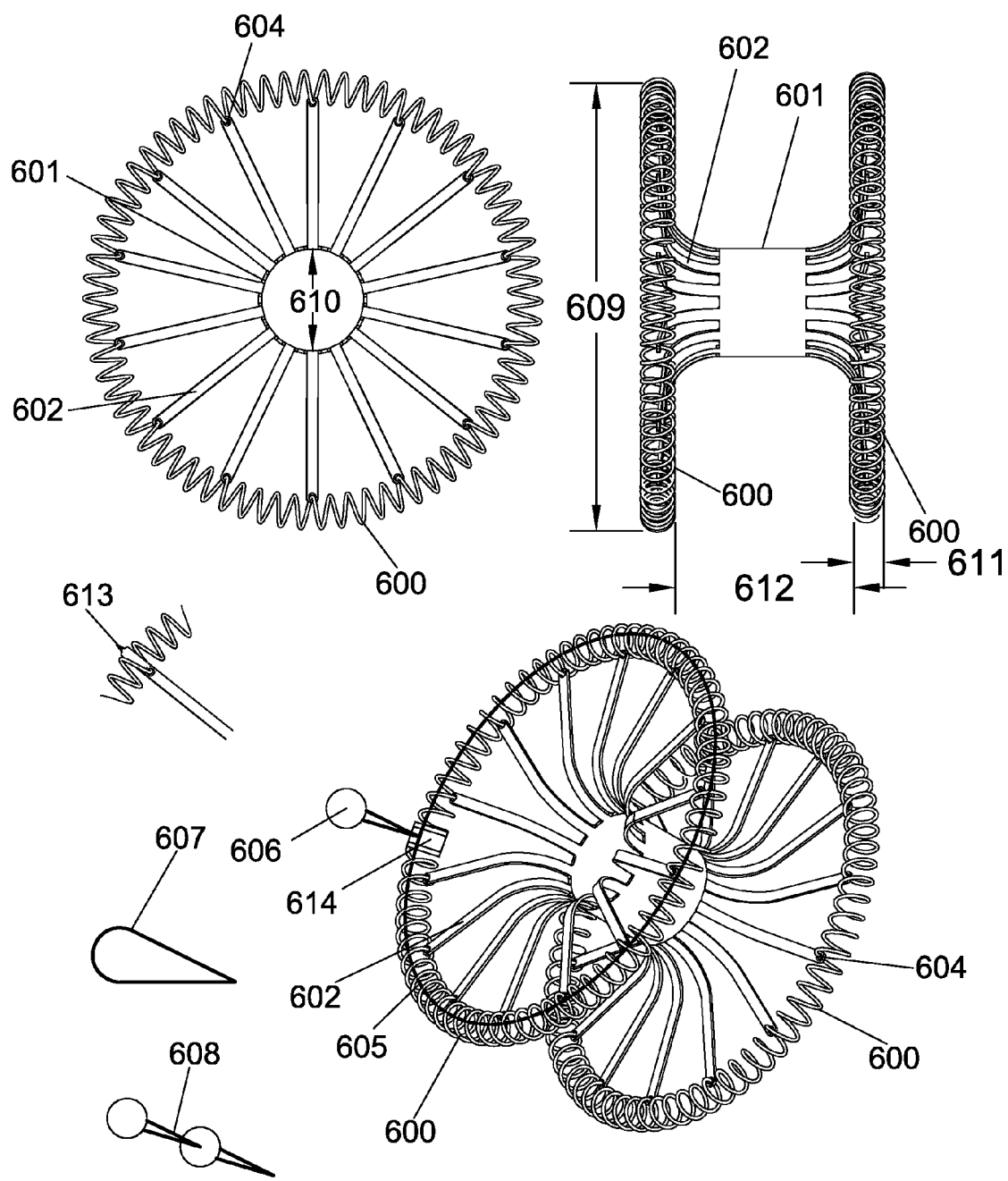
FIG. 7 is a drawing of an alternative embodiment of an expandable anchor. The expandable anchor is comprised of two toroidally shaped wound springs connected to a central cylinder by control arms.

FIG. 7 is a drawing of an alternative embodiment of an expandable anchor. The expandable anchor provides for an anchoring means to hold an intestinal bypass sleeve 111 within the small intestine. The expandable anchor is comprised of two toroidally shaped wound springs 600 connected to a central cylinder 601 by control arms 602. The toroidal springs 600 are prewound in a straight configuration and then the springs 600 are wound through the eyelets 604 on the end of the control arms and formed into the toroidal shape. The expandable anchor can be non-covered or it can have a polymer covering on the outside and inside as disclosed in FIG. 16. The spring ends are joined together at a spring joiner 614. The spring ends may be fastened to the spring joiner 614 by mechanical means or they may be laser welded to the spring joiner 614. The spring joiner serves two purposes, to provide for a means of spring end termination and joining of the two spring ends and also provides for an exit point for the drawstring 605 to exit the spring 600. The drawstring 605 is fed through the central axis of the toroidal spring 600. A drawstring 605 may be used only on the proximal disk or on both the proximal and distal disks.

Figure 15:
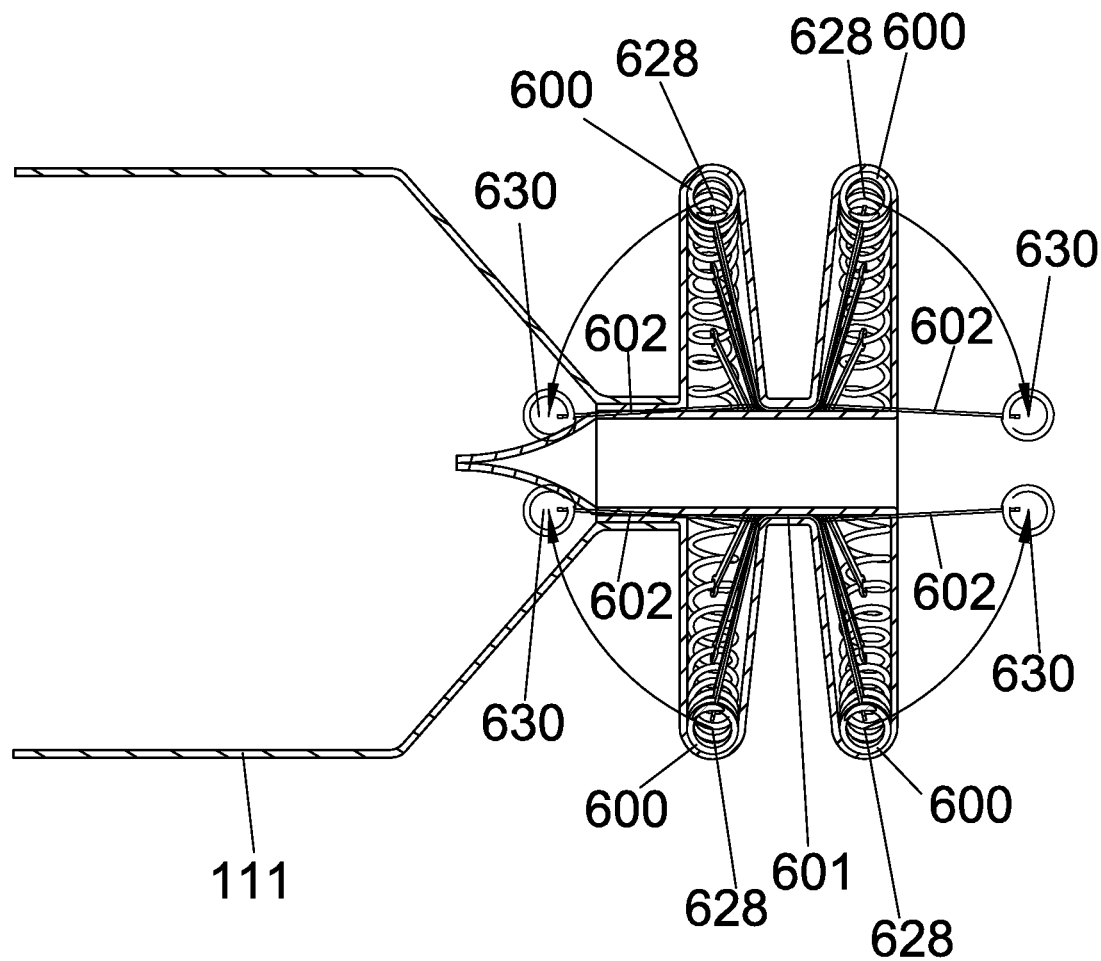
FIG. 15 is a drawing of an expandable anchor and intestinal bypass sleeve.

The two ends of the drawstring 605 both exit the spring joiner 614 and are terminated at ball 606. Pulling on the ball 606 and drawing the drawstring 605 through the spring joiner 614 causes the diameter of the spring 600 to be reduced and the control arms to bend and deflect as shown in FIG. 15. The drawstring 605 can also be terminated in loop 607 or with two balls 608 spaced apart.

Figure 12:
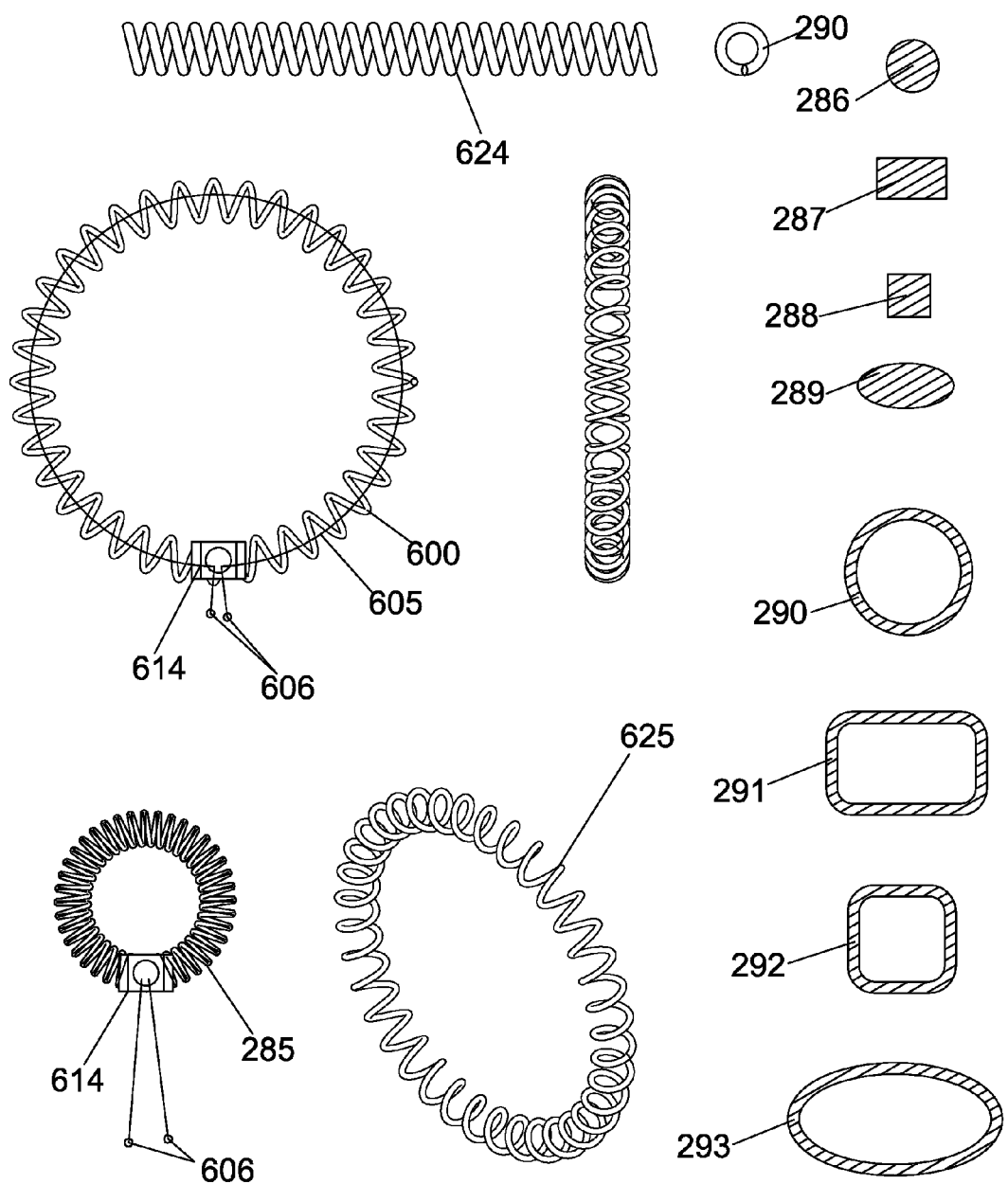
FIG. 12 is a drawing of the toroidally wound springs in a straight configuration, before the toroidally wrapped spring is assembled onto the control arms.

The toroidal springs are further disclosed in FIG. 12 and FIG. 13. The central cylinder and the control arms of the exemplary embodiment are laser cut from a piece of Nitinol tubing. In the exemplary embodiments, the expandable anchor is designed to allow the anchor to be of a self-expanding design. A self-expanding anchor design can be compressed in diameter to allow the device to be loaded onto a delivery catheter. The anchor can then recover elastically to the original starting diameter, with the anchor diameter decreasing only a small amount due to nonelastic recovery. The anchor can also be made of a plastically deformable design and require a mechanical force applied to it in the radial or longitudinal direction to accomplish the expansion of the anchor. The mechanical force can be accomplished with an inflatable balloon type device, radially expanding the anchor or it may also be accomplished by a longitudinal compression of the anchor by a screw type mechanism or cable tensioning means. As shown, the anchor has a distal disk and a proximal disk that is comprised of 14 control arms on each portion. According to various embodiments, the anchor could have from 3 to 72 control arms for the proximal disk and the distal disk.

According to exemplary embodiments, the central cylinder 601 and control arms 602 are made from a nickel titanium alloy (Nitinol). Springs 600 are made from MP35N LT. Other alternative suitable alloys for manufacturing the central cylinder 601, control arms 602 and springs 600 are stainless steel alloys: 304, 316L, BioDur®108 Alloy, Pyromet Alloy® CTX-909, Pyromet® Alloy CTX-3, Pyromet® Alloy 31, Pyromet® Alloy CTX-1, 21 Cr-6Ni-9Mn Stainless, Pyromet Alloy 350, 18Cr-2Ni-12Mn Stainless, Custom 630 (17Cr-4Ni) Stainless, Custom 465® Stainless, Custom 455® Stainless, Custom 450® Stainless, Carpenter 13-8 Stainless, Type 440C Stainless, cobalt chromium alloys-MP35N, Elgiloy, L605, Biodur® Carpenter CCM alloy, titanium and titanium alloys, Ti-6Al-4V/ELI and Ti-6Al-7Nb, Ti-15Mo, Tantalum, Tungsten and tungsten alloys, pure platinum, platinum-iridium alloys, platinum-nickel alloys, niobium, iridium, conichrome, gold and gold alloys. The anchor may also be comprised of the following absorbable metals: pure Iron and magnesium alloys. The central cylinder 601, control arms 602 and springs 600 may also be comprised of the following plastics: Polyetheretherketone (PEEK), polycarbonate, polyolefins, polyethylenes, polyether block amides (PEBAX), nylon 6, 6-6, 12, Polypropylene, polyesters, polyurethanes, polytetrafluoroethylene (PTFE) Poly(phenylene sulfide) (PPS), poly(butylene terephthalate) PBT, polysulfone, polyamide, polyimide, poly(p-phenylene oxide) PPO, acrylonitrile butadiene styrene (ABS), Polystyrene, Poly(methyl methacrylate) (PMMA), Polyoxymethylene (POM), Ethylene vinyl acetate, Styrene acrylonitrile resin, Polybutylene. The anchor, according to exemplary embodiments, is laser cut from a round tubing or from a flat sheet of Nitinol and then is rolled into a cylindrical shape after laser cutting. The anchor, according to exemplary embodiments, is made from a Nitinol tube of about 9 mm outside diameter by a wall thickness of 0.012 inch thick. Alternatively a starting tube outside diameter can range from about 2 mm to 16 mm. An alternative construction method is to laser cut or chemical etch the pattern from a flat sheet of Nitinol with a thickness of 0.002 inch to 0.020 inch.

According to various embodiments, the anchor has an inside diameter 610 in the range of about 2 mm to 20 mm. The anchor has disk-shaped features that have a diameter 609 in the range of about 20 mm to 66 mm. Anchor has a central cylinder 601 that has an outside diameter in the range of 4 mm to 20 mm. Central cylinder section 601 can have a length 612 of about 1 mm to 30 mm and is close to width of the pylorus 106. The disks can have a length 611 of 1 mm to 10 mm. The proximal disk and distal disk can alternatively be formed in the shape of a cup. The central cylinder 601, in various embodiments, is made from a material having a stiffness sufficient to resist compressive forces applied by the pylorus. The control arms 602 can radially project out through the diameter of the spring 600 and form a barb 613 on the outside diameter of the spring 600.

Figure 8:
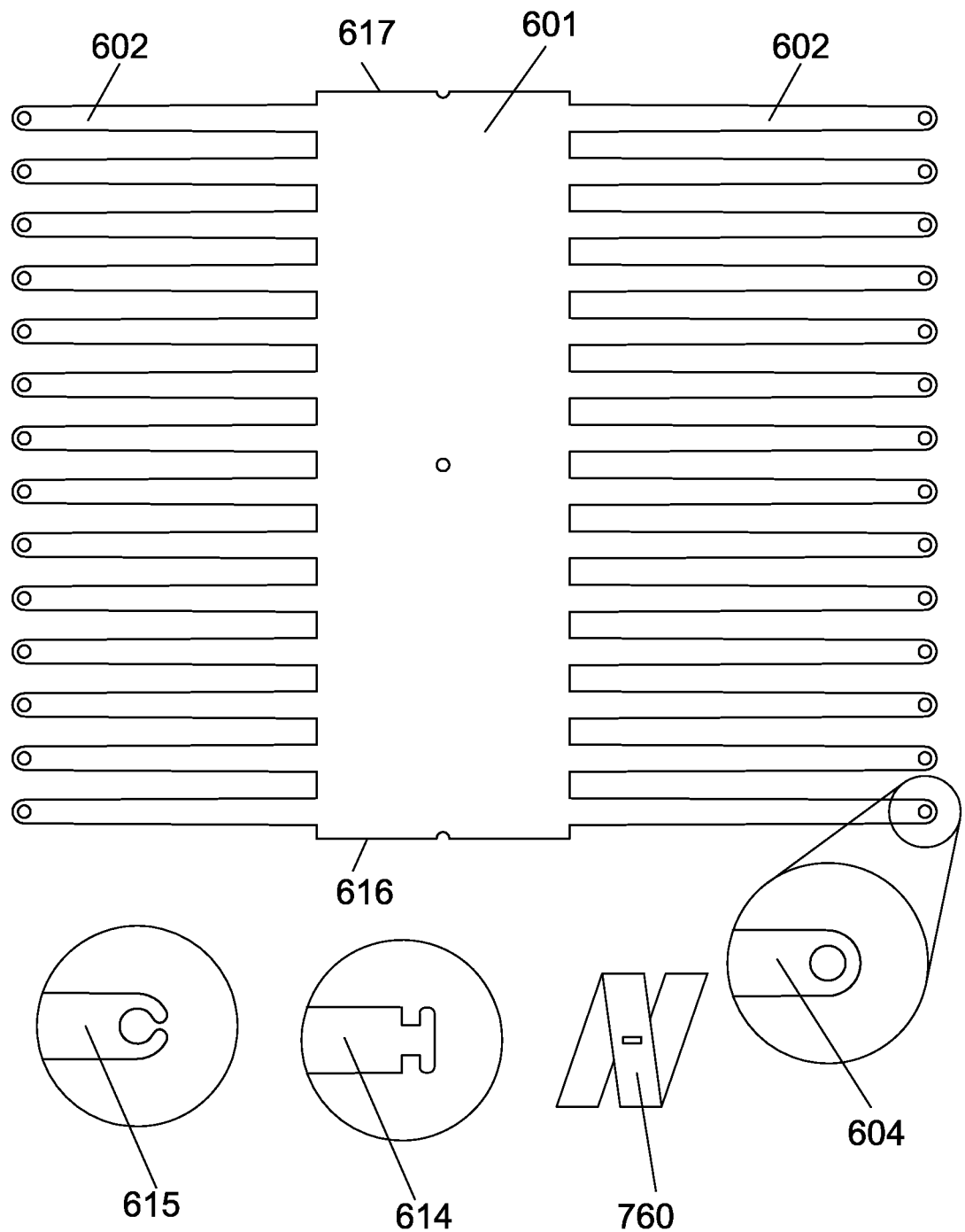
FIG. 8 is a drawing of a flat representation of the control arms and central cylinder as in FIG. 7 as laser cut from a piece of tubing.

FIG. 8 is a drawing of a flat representation of the circumference of the central cylinder 601 and control arms 602. The control arms have round holes at the end of the arms to wind the toroidal spring through when assembling the springs 600 onto the control arms 602 to make an expandable anchor. The holes 604 at the end of the control arms 602 can be made in an alternative shape such as elliptical, rectangular or square. Alternatively the control arms 602 may have an open slot 615 to allow the spring to be snap fit into the opening on the control arms 602. The end of the control arms 602 may also have a t-shape that could be inserted into a slot 760 laser cut into the wire of the spring 600. The two edges of the flat representation 616 and 617 will touch when the flat representation is wrapped around a cylinder.

Figure 9:
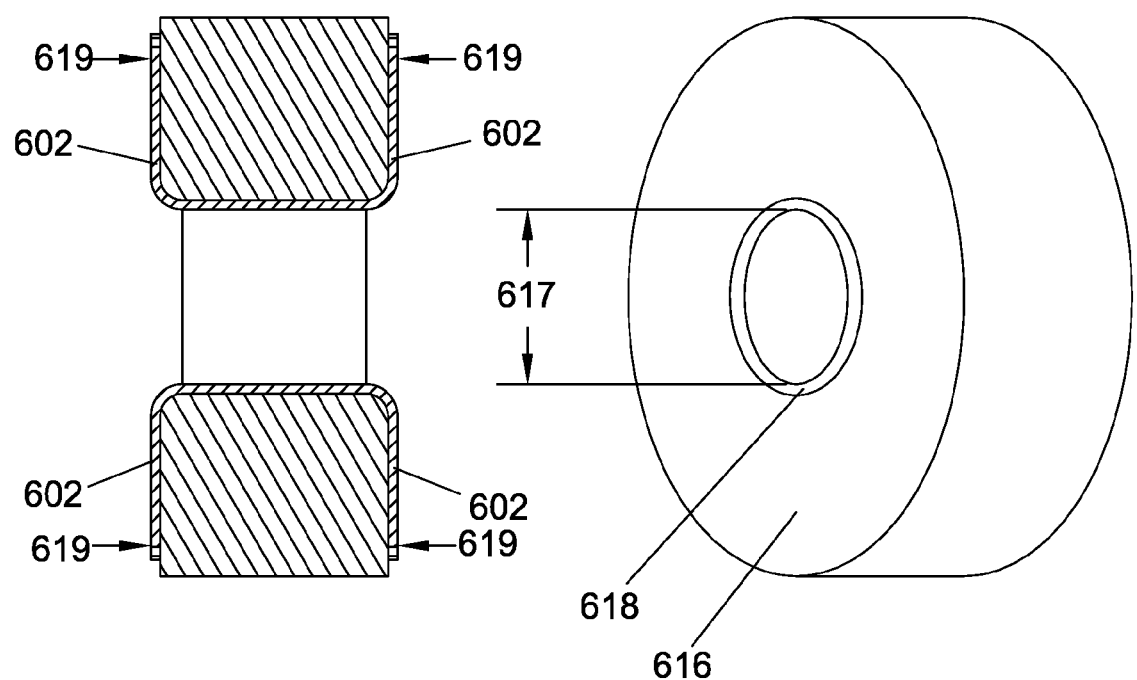
FIG. 9 is a drawing of a heat set mandrel used for heat setting or forming the FIG. 8 part into the final shape of expandable anchor in FIG. 7
Figure 10:
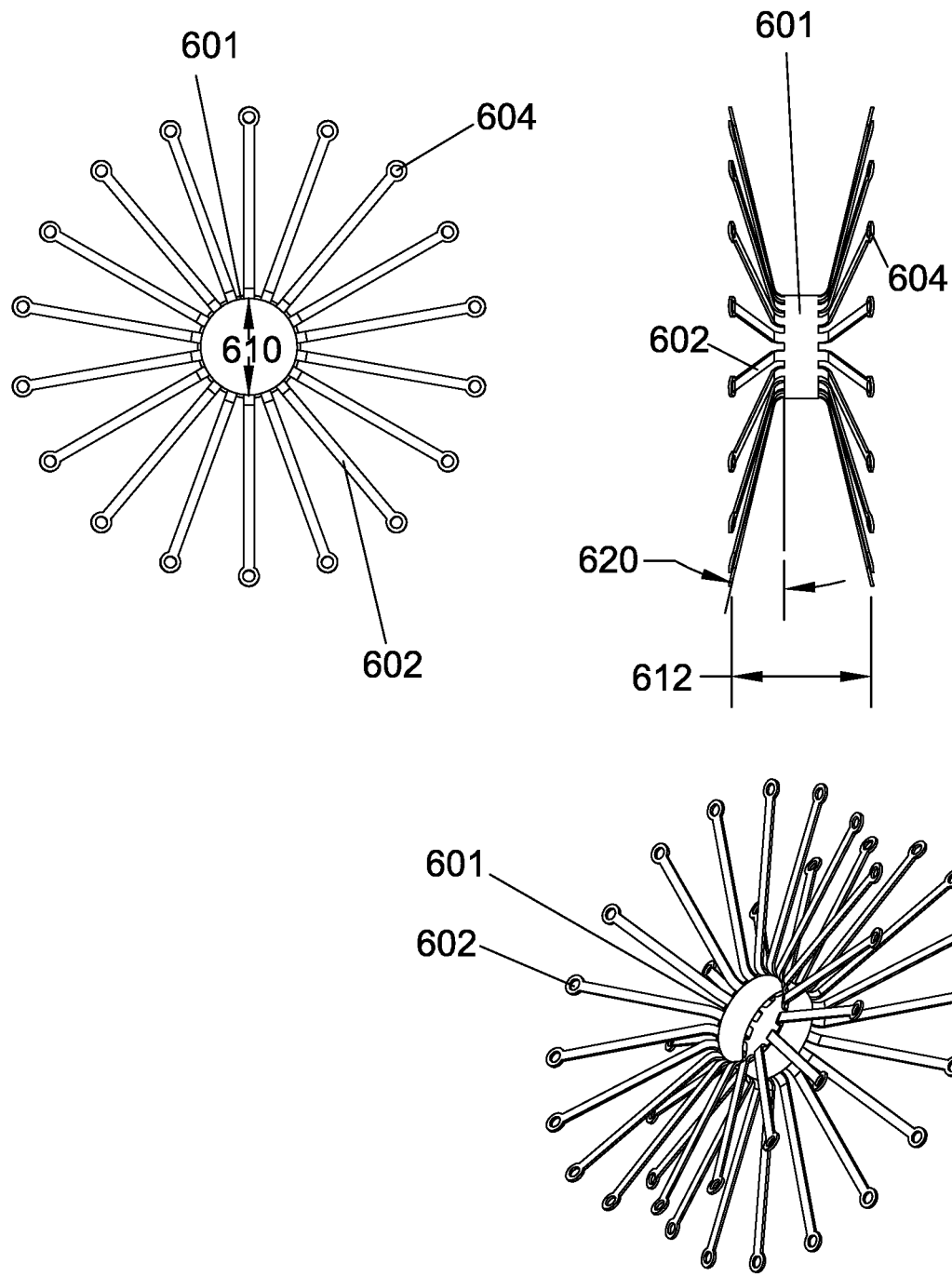
FIG. 10 is drawing of the control arms heat set to the final shape before the toroidally shaped wound springs are assembled on the control arms.

FIG. 9 is a drawing of a heat set mandrel 616 used to heat set the laser cut Nitinol tube shown in FIG. 8 into the final shape of the central cylinder 601 and control arms 602 of FIG. 10. The inside diameter 617 of the heat set mandrel 616 closely approximates the outside diameter of the central cylinder 601. A radius 618 is cut into the mandrel to force the Nitinol to bend to a gradual radius to control the strain level during shape setting of the Nitinol part into the final shape of FIG. 10. Laser cut tube of FIG. 8 is inserted into the heat set mandrel of FIG. 9. The control arms are bend outward and then compressed longitudinally to the final location 619 on the heat set mandrel. The Nitinol laser cut tube and the heat set mandrel 616 are then heated to a temperature of 500 degree centigrade for 10 minutes and then quickly cooled to room temperature. The laser cut tube is then removed from the inside of the heat set mandrel 616 and the laser cut tube is now set to the shape in FIG. 10.

FIG. 10 is a drawing of the laser cut tube of FIG. 8. After it has been heat set and formed into the final shape for the expandable anchor. Control arms 602 are formed radially outward from the central cylinder 601. The bend angle 620 of the control arms can be from −30 degrees to approximately 45 degrees.

Figure 11:
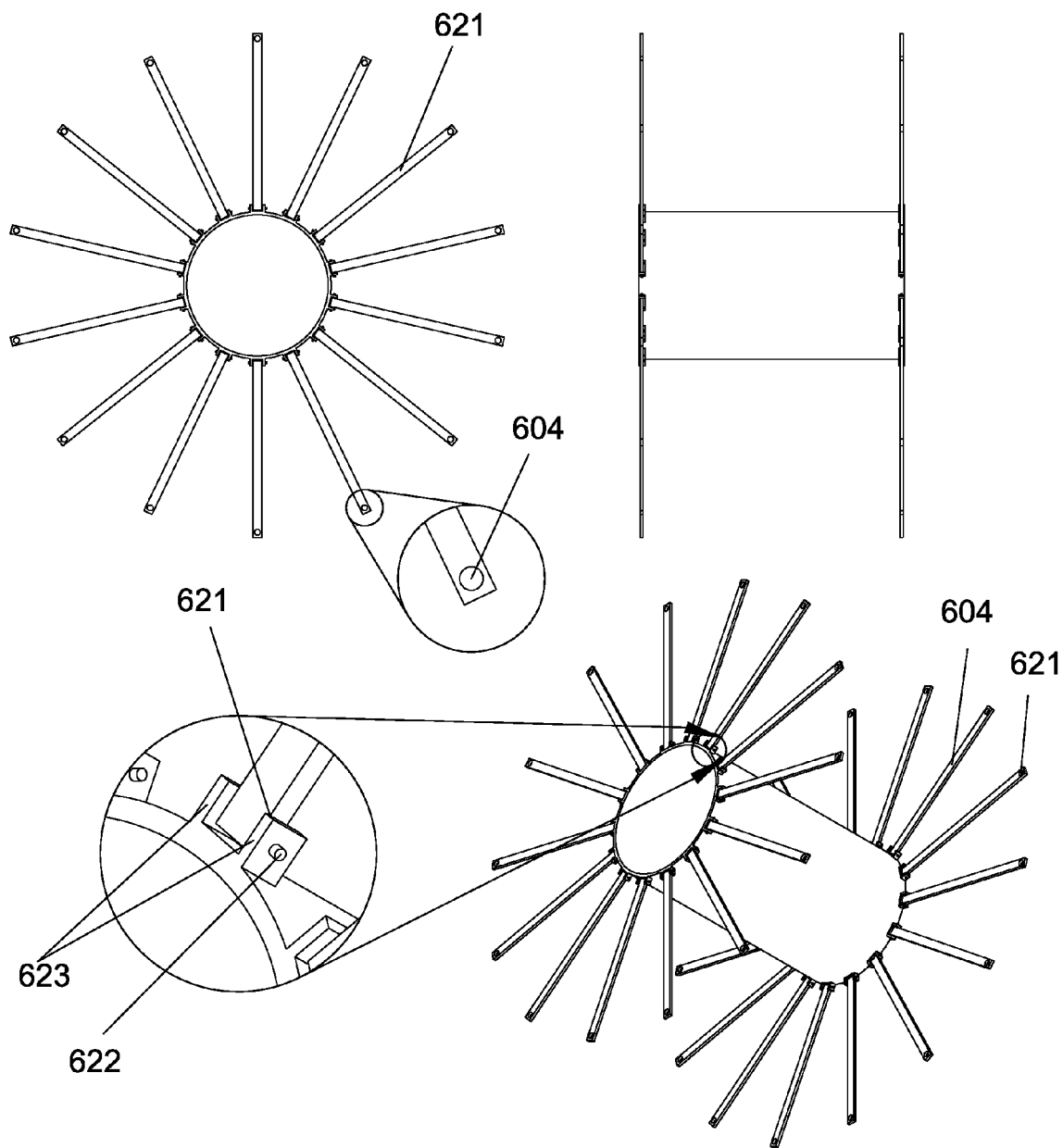
FIG. 11 is a drawing of an alternative embodiment of a central cylinder and control arms.

FIG. 11 is a drawing of an alternative embodiment of a central cylinder and control arms. The control arms are attached to the central cylinder by a simple pin 622 and socket 623 arrangement like used in four bar linkages. The number of arms control arms can range from 3 to 72.

FIG. 12 is a drawing of toroidal shaped spring 600 as used in the expandable anchor of FIG. 7. The toroidal spring 600 is shown separately here for ease of illustration, but the spring 600 will be assembled onto the control arms 602 to form an expandable anchor as in FIG. 7.

The toroidal-shaped spring 600 may be first formed by winding a straight compression spring 600. The compression spring 600 may be made from round wire 286, rectangular wire 287, square wire 288, or elliptical wire 289. The compression spring 600 can be wound to have a round shape 290, rectangular shape 291, square shape 292, or an elliptical shape 293. The wire may be made from Nitinol, stainless steel, Elgiloy, L605, MP35N titanium, niobium or other suitable metal. The wire is, in various embodiments, made of a solid wire but can alternatively be made of stranded or braided wire. The outer diameter or inner core of the wire may be clad or plated with gold, tantalum, platinum, iridium, or other suitable material. The wire may be co-drawn (e.g., drawn filled tube-Fort Wayne Metals) and have an outer core of a high strength material such as Nitinol, stainless steel, Elgiloy, L605, MP35N, titanium, niobium and an inner core of a high radio-opacity material such as gold, tantalum, platinum, or iridium. Alternatively, the wire is made from a plastic monofilament such as PEEK, PET or Delrin. Compression spring 624 is formed into a toroidal shape by bending spring ends towards each other and winding the spring through the holes 604 in the ends of the control arms 602 and joining spring ends at spring joiner connector 614. A perspective view of the toroidal spring is shown in 625 (not assembled to control arms 602). A drawstring 605 is contained within the center of the toroidal spring 600. The drawstring 605 is threaded through a hole in the spring joiner 614. Drawstring 605 is terminated at spheres that can be crimped onto the end of the drawstring 605. The spheres may be made of metal or plastic and may be attached to the drawstring 605 by crimping, welding, gluing, insert molding or other suitable means. The drawstring may be comprised of plastic or metal and may be made of a monofilament or braided cable material. When spheres 605 are withdrawn from spring joiner 614, drawstring 605 is tensioned and the diameter of the toroidal spring and control arms 602 is reduced to the smaller diameter as in 285.

FIG. 13A is a drawing of an alternative embodiment of an expandable anchor formed in the shape of a toroidal-shaped spring 282 as previously disclosed in FIG. 12. The spring may have small tissue penetrating anchors 296 on the outer surface of the spring. Tissue penetrating anchor 296 may be made from, stainless steel, Elgiloy, L605, MP35N, titanium or niobium and may be crimped onto the wire or welded. Tissue penetrating anchors 296 may be an optional feature that can be added if the patient's anatomy does not have a pyloric ring that is adequate for anchoring.

FIG. 13B is a drawing of an alternative embodiment of an expandable anchor formed in the shape of a toroidal-shaped spring as previously disclosed in FIG. 12. The toroidal-shaped spring is formed of segments where the direction of the winding of the spring is reversed to cancel out the helical twisting action of the spring. The individual segments 297, 298, 299 and 300 can be connected at joiners 301. Alternatively the entire toroidal spring can be laser cut as one unitary piece by laser cutting the wound coil in the unformed shape as in 281 from a piece of round tubing.

FIG. 13C is a drawing of an alternative embodiment of an expandable anchor formed in the shape of a toroidal-shaped spring as previously disclosed in FIG. 12. The spring is wound to have double helices that are 180 degrees offset from each other.

Figure 14:
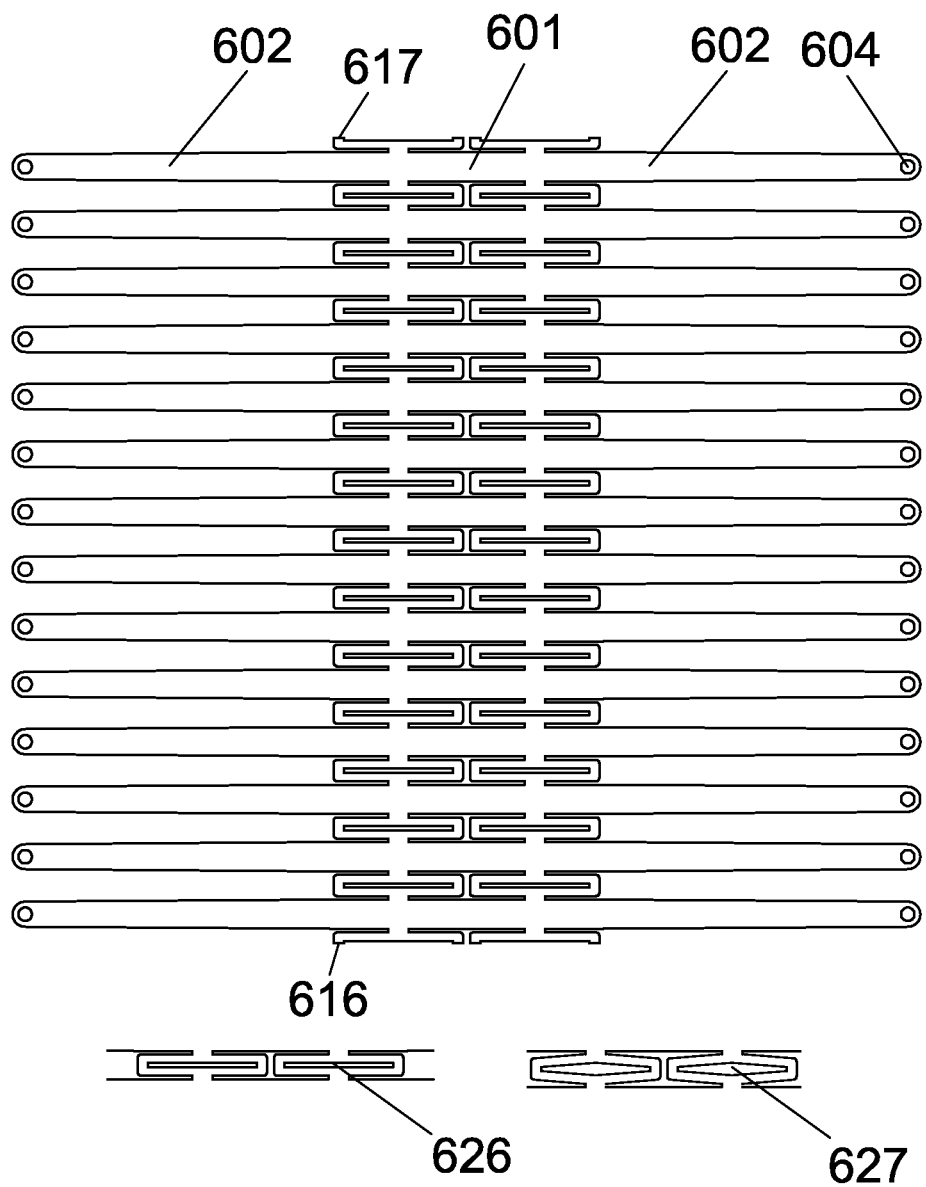
FIG. 14 is a drawing of an alternative embodiment of a central cylinder and control arms.

FIG. 14 is a drawing (a flat representation of the circumference) of an alternative embodiment of the central cylinder 601 and control arms 602 for an expandable anchor as disclosed in FIG. 7. The central cylinder 601 has slots 626 cut into the wall of the tubing. The slots 626 can elastically elongate and compress circumferentially as in 627 to allow the diameter of the central tube to be compressed to be loaded onto a delivery catheter and then elastically rebound to the original larger diameter when the expandable anchor is deployed through the delivery catheter. The control arms 602 have round holes 604 at the end of the arms to wind the toroidal spring through when assembling the springs 600 onto the control arms 602 to make an expandable anchor. The two edges of the flat representation 616 and 617 will touch when the flat representation is wrapped around a cylinder.

FIG. 15 is a drawing of an expandable anchor and an intestinal bypass sleeve 111. Expandable anchor can be reduced in diameter by applying tension to the drawstring at the balls 608. The diameter of the toroidal spring 600 decreases and the control arms 602 rotate from 628 to 630 as the diameter of the toroidal springs are decreased in size.

FIG. 16 is a sectional view of the pyloric antrum 104, pyloric aperture 105, pylorus 106, duodenal bulb 107 and duodenum 112. An expandable anchor 633 and intestinal bypass sleeve 111 is implanted into the pylorus 106. The expandable anchor 633 is shown here in cross section to allow for better visualization of the polymer covering on the expandable anchor 633. The expandable anchor 633 is encapsulated on the outside and inside with a polymer covering 634.

In various exemplary embodiments, the expandable anchor 633 is not covered, while in other exemplary embodiments, it is covered with a polymer membrane made from a material such as silicone, flourosilicone elastomers such as Viton, polyurethane, PTFE (polytetrafluoroethylene), FEP (fluorinated ethylene propylene), polyethylene, ePTFE (expanded polytetrafluoroethylene), PFA (Perfluoroalkoxy), PVDF (Polyvinylidene Flouride, Tetrafluoroethylene), THV (Hexafluoropropylene and Vinylidene Fluoride), ETFE (Ethylenetetrafluoroethylene), ECTFE (Chloro Trifluoro Ethylene/Ethylene Copolymer) EFEP (copolymer of ethylene, tetrafluoroethylene, and hexafluoropropylene), PVF (polyvinyl fluoride). The expandable anchor 633 can be made from metal or plastic. The intestinal bypass sleeve 111 can vary in length from 1-2 inches in length up to several feet. In some embodiments, the sleeve bypasses the length of the duodenum up to the ligament of Treitz. The sleeve can be longer and bypass into the jejunum. The intestinal bypass sleeve 111 may be made from a thin-walled polymer material such as silicone, flourosilicone elastomers such as Viton, polyurethane, PTFE (polytetrafluoroethylene), FEP (fluorinated ethylene propylene), polyethylene, expanded polytetrafluoroethylene (ePTFE), PFA (Perfluoroalkoxy), PVDF (Polyvinylidene Flouride, Tetrafluoroethylene), THV (Hexafluoropropylene and Vinylidene Fluoride), ETFE (Ethylenetetrafluoroethylene), ECTFE (Chloro Trifluoro Ethylene/Ethylene Copolymer) EFEP (copolymer of ethylene, tetrafluoroethylene, and hexafluoropropylene), PVF (polyvinyl fluoride) or other suitable material or combinations of the listed a materials. The ePTFE material may be coated with another polymer material such as silicone, FEP or other suitable material to render it totally impermeable. In exemplary embodiments, the wall thickness of the intestinal bypass sleeve 111 may be in the range of 0.001 inch to 0.012 inch thick. The intestinal bypass sleeve 111 may be made by extrusion, into a tubular form or a lay flat tubing, dip coated from a liquid solution, powder coated from fine particles of polymer or paste extruded and then stretched as is the case with ePTFE. Intestinal bypass sleeve may be made porous or nonporous. Sleeve may have surface coatings to close up pores of porous membrane. Such as a surface coating of silicone, polyurethane, FEP applied to porous substrate to render it non-permeable. ePTFE is inherently hydrophobic and has some resistance to water penetration, but it may be desirable to have a higher water entry pressure or make ePTFE impermeable. Intestinal bypass sleeve may have a lubricious (or sticky) hydrophilic coating or a hydrogel added to the inner or outer surface to reduce the friction of the surface or to make it easier for food to pass through the liner or to decrease the outer surface coefficient of friction or make the sleeve stay in place better in the intestines. Intestinal bypass sleeve or expandable anchor may be used for drug delivery, delivery of peptides or other therapeutics by incorporating a drug or peptide into the polymer wall thickness of the intestinal bypass sleeve. The drug or peptide may be added directly to the surface of the intestinal liner without a polymer or covalently bonded to the polymer surface.

The drug or peptide may be eluted from a surface coating on the sleeve or anchor which incorporates the drug into the coating. Polymers that may be used as a coating to elute a drug include silicone, polyurethane, Polyvinyl Alcohol, Ethylene vinyl acetate, Styrene acrylonitrile, Styrene-Butadiene, Pebax® or other suitable polymer. Absorbable polymers that may be used for drug delivery include, Polyglycolic acid (PGA), Polylactide (PLA), Poly(ε-caprolactone), Poly(dioxanone) Poly(lactide-co-glycolide) or other suitable polymer. Other suitable coatings for increased biocompatibility or drug release may include human amnion, collagen Type I, II, III, IV, V, VI—Bovine, porcine, or ovine. The coating on the intestinal bypass sleeve can also take the form of a liquid that can be used to release the drug or peptide include, Vitamin D, A, C, B, E, olive oil, polyethylene glycol, vegetable oils, essential fatty acids, alpha-linolenic acid, lauric acid, linoleic acid, gamma-linolenic acid, palmitoleic acid or other suitable liquids. The drug may serve to increase satiety, to interrupt the secretion of secondary hormones or digestive enzymes, release antibacterial agents to reduce infection, to increase the fibrotic reaction of the intestinal tract, to decrease the fibrotic reaction of the intestinal tract, to target changes in the cellular composition such as decreasing the number of receptor cells in the duodenum.

Intestinal bypass sleeve can release cholecystokinin, gastrin, secretin, gastric inhibitory peptide, motilin, glucagon like peptide 1, bile, insulin, pancreatic enzymes, ghrelin, penicillin, amoxicillin, ampicillin, carbenicillin, cloxacillin, dicloxacillin, nafcillin, oxacillin, penicillin g, penicillin V, Piperacillin, Ticarcillin Aminoglycosides, Amikacin, Gentamicin, Kanamycin, Neomycin, NEO-RX, Netilmicin, Streptomycin, Tobramycin, Carbapenems, Ertapenem, Doripenem, DORIBAX, Emipenem-cilastatin, Meropenem, Cefadroxil, Cefazolin, Cephalexin rapymicin, taxol, Vitamin A, Vitamin C, Vitamin D, Vitamin B, Vitamin E, fatty acids, oils, vegetable oils, aspirin, somastatin, motilin, trypsinogen, chymotrypsinogen, elastase, carboxypeptidase, pancreatic lipase, amylase, enteroglucagon, gastric inhibitory polypeptide, Vasoactive intestinal peptide, PYY, Peptide Tyrosine Tyrosine, Leptin, Pancreatic polypeptide.

Figure 17:
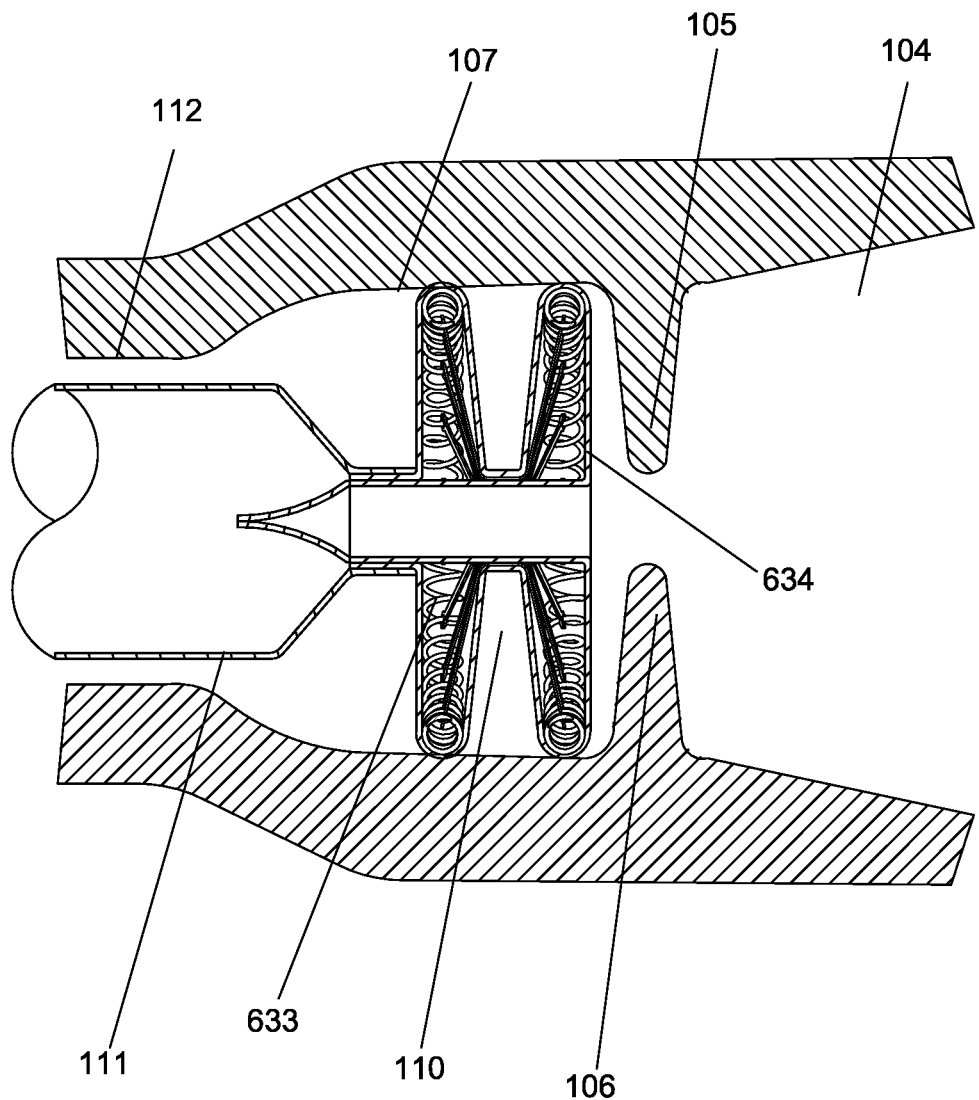
FIG. 17 is a sectional view of the expandable anchor and the intestinal bypass sleeve implanted into the duodenal bulb.

FIG. 17 is a drawing of the expandable anchor as shown in FIG. 16 wherein the expandable anchor 633 is deployed/placed into the duodenal bulb 107 instead of across the pylorus 106. Other alternative implant locations include the duodenum 112, pyloric antrum 104 and the gastroesophageal (GE) junction.

Figure 18:
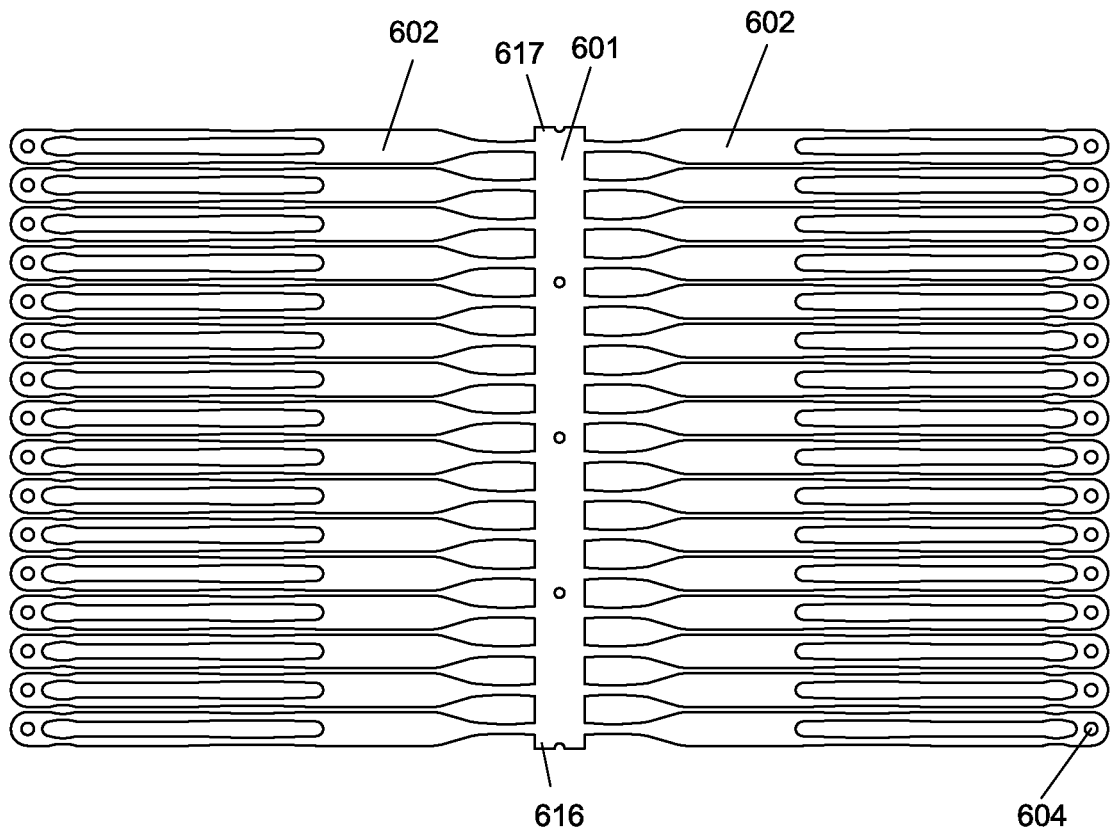
FIG. 18 shows a drawing flat representation of an alternative embodiment of the control arms and central cylinder as laser cut from a piece of tubing. The final heat set shape will be similar to the shape in FIG. 23.

FIG. 18 is a drawing of a flat representation of an alternate embodiment of the circumference of the laser cut central cylinder 601 and control arms 602. The control arms have round holes 604 at the end of the arms to wind the toroidal shape spring through when assembling the springs 600 onto the control arms 602 to make an expandable anchor. The two edges of the flat representation of the circumference 616 and 617 will touch when the flat representation is wrapped around a cylinder. The expanded final shape for the laser cut part disclosed in FIG. 18 will assume a shape similar to FIG. 23. An alternative embodiment of the final expandable anchor of FIG. 18 does not incorporate the toroidal wound spring 600 into the final expandable anchor.

Figure 19:
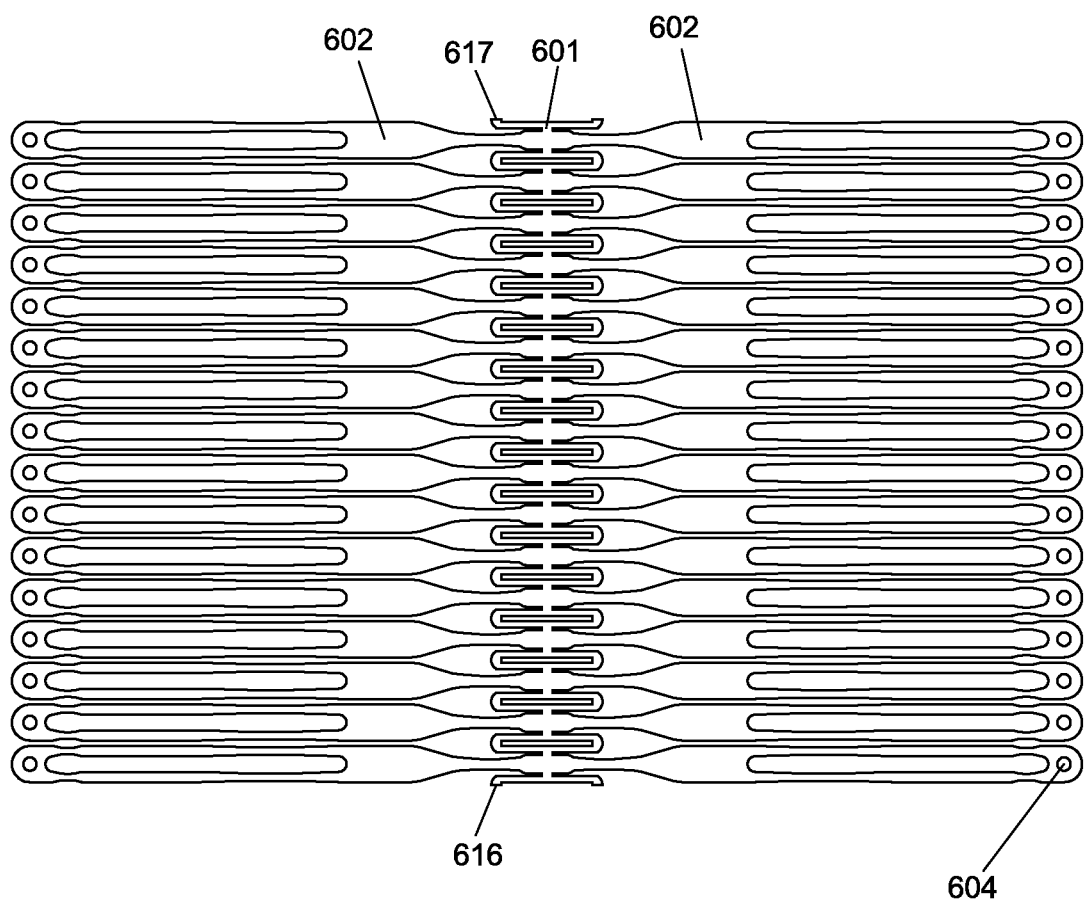
FIG. 19 shows a drawing flat representation of an alternative embodiment of the control arms and central cylinder as laser cut from a piece of tubing. The final heat set shape will be similar to the shape in FIG. 23.

FIG. 19 is a drawing of a flat representation of an alternate embodiment of the circumference of the laser cut central cylinder 601 and control arms 602. The control arms have round holes 604 at the end of the arms to wind the toroidal shaped spring through when assembling the springs 600 onto the control arms 602 to make an expandable anchor. The two edges of the flat representation of the circumference 616 and 617 will touch when the flat representation is wrapped around a cylinder. The expandable anchor of FIG. 19 incorporates an expandable and compressible central cylinder by including slots cut into the circumference of the tube. This was previously disclosed in FIG. 14.

Figure 23:
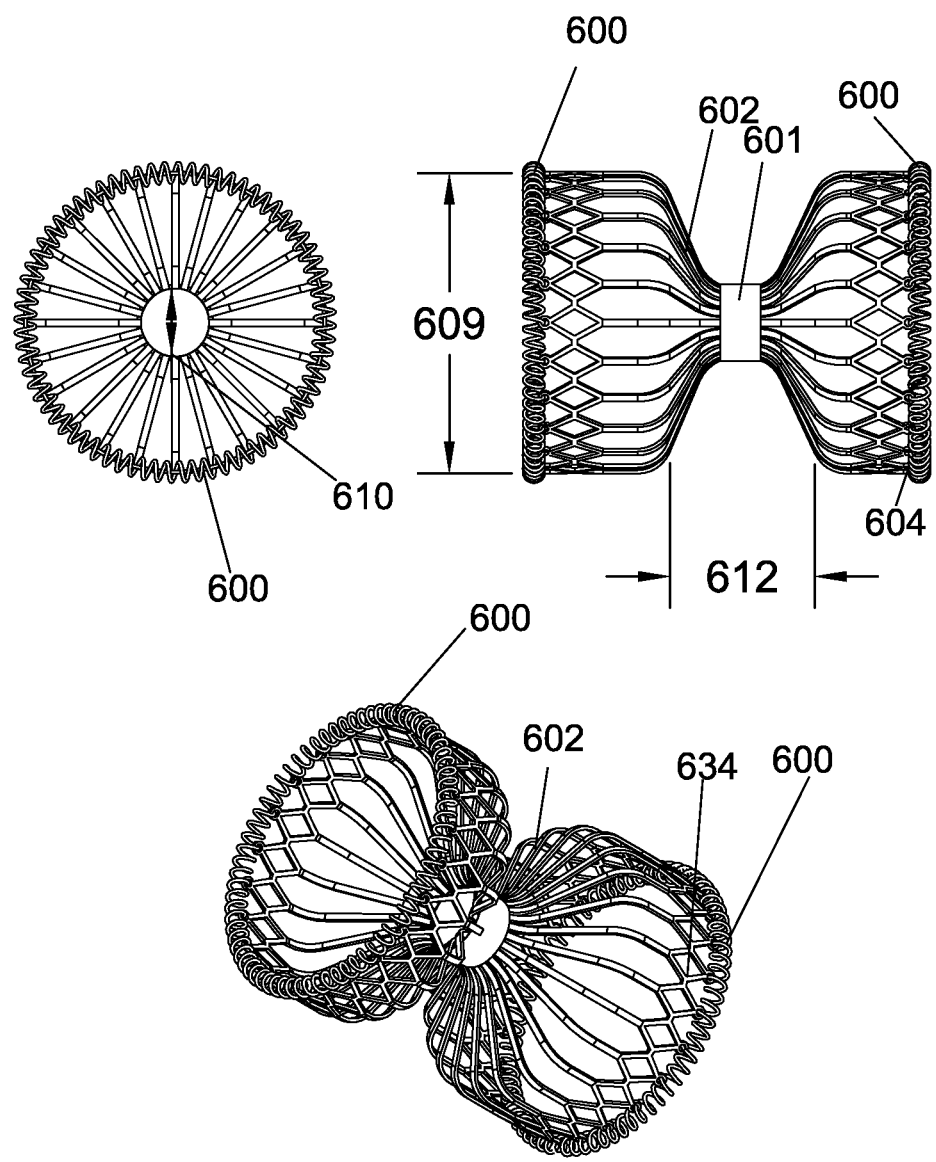
FIG. 23 is a drawing of an alternative embodiment of an expandable anchor. The expandable anchor is comprised of two toroidally shaped wound springs connected to a central cylinder by control arms.

The expanded final shape for the laser cut part disclosed in FIG. 19 will assume a shape similar to FIG. 23. An alternative embodiment of the final expandable anchor of FIG. 19 does not incorporate the toroidal wound spring 600 into the final expandable anchor.

Figure 20:
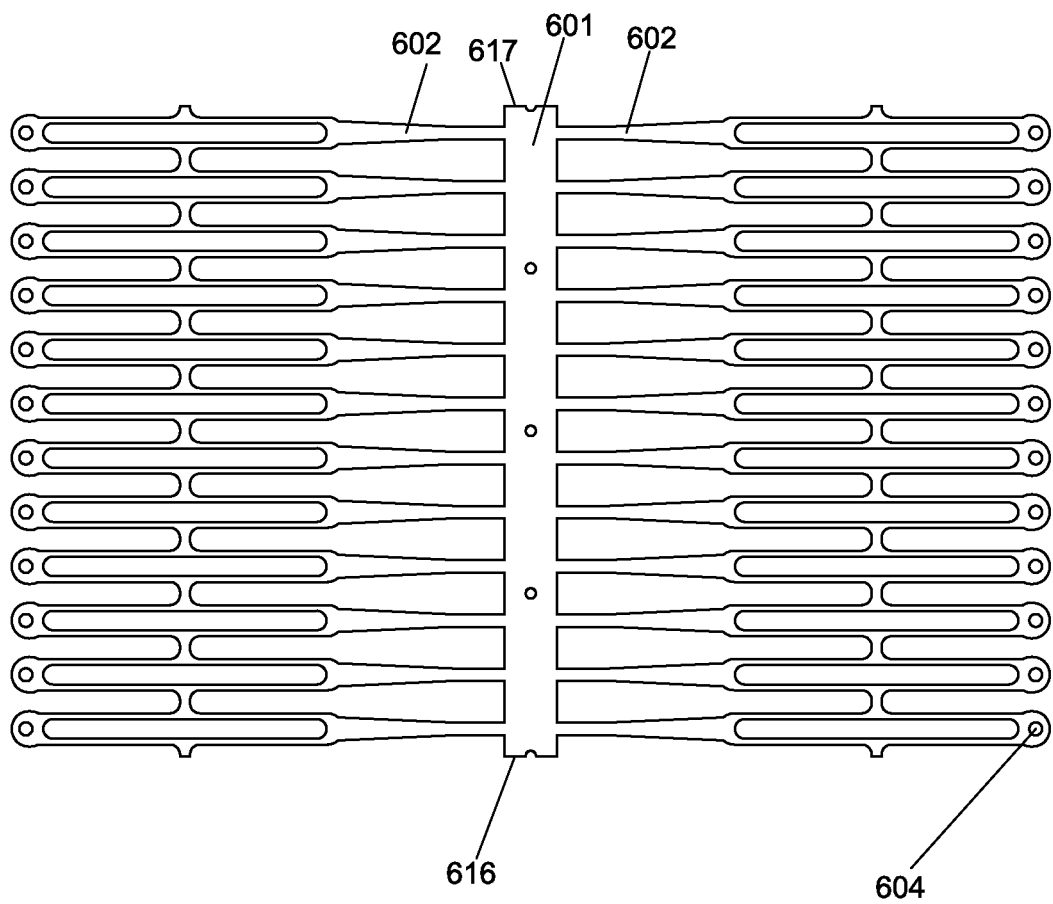
FIG. 20 is a drawing flat representation of an alternative embodiment of the control arms and central cylinder as laser cut from a piece of tubing. The final heat set shape will be similar to the shape in FIG. 23.

FIG. 20 is a drawing of a flat representation of an alternate embodiment of the circumference of the laser cut central cylinder 601 and control arms 602. The control arms have round holes 604 at the end of the arms to wind the toroidal shaped spring through when assembling the springs 600 onto the control arms 602 to make an expandable anchor. The two edges of the flat representation of the circumference 616 and 617 will touch when the flat representation is wrapped around a cylinder. The expanded final shape for the laser cut part disclosed in FIG. 20 will assume a shape similar to FIG. 23. An alternative embodiment of the final expandable anchor of FIG. 20 does not incorporate the toroidal wound spring 600 into the final expandable anchor.

Figure 21:
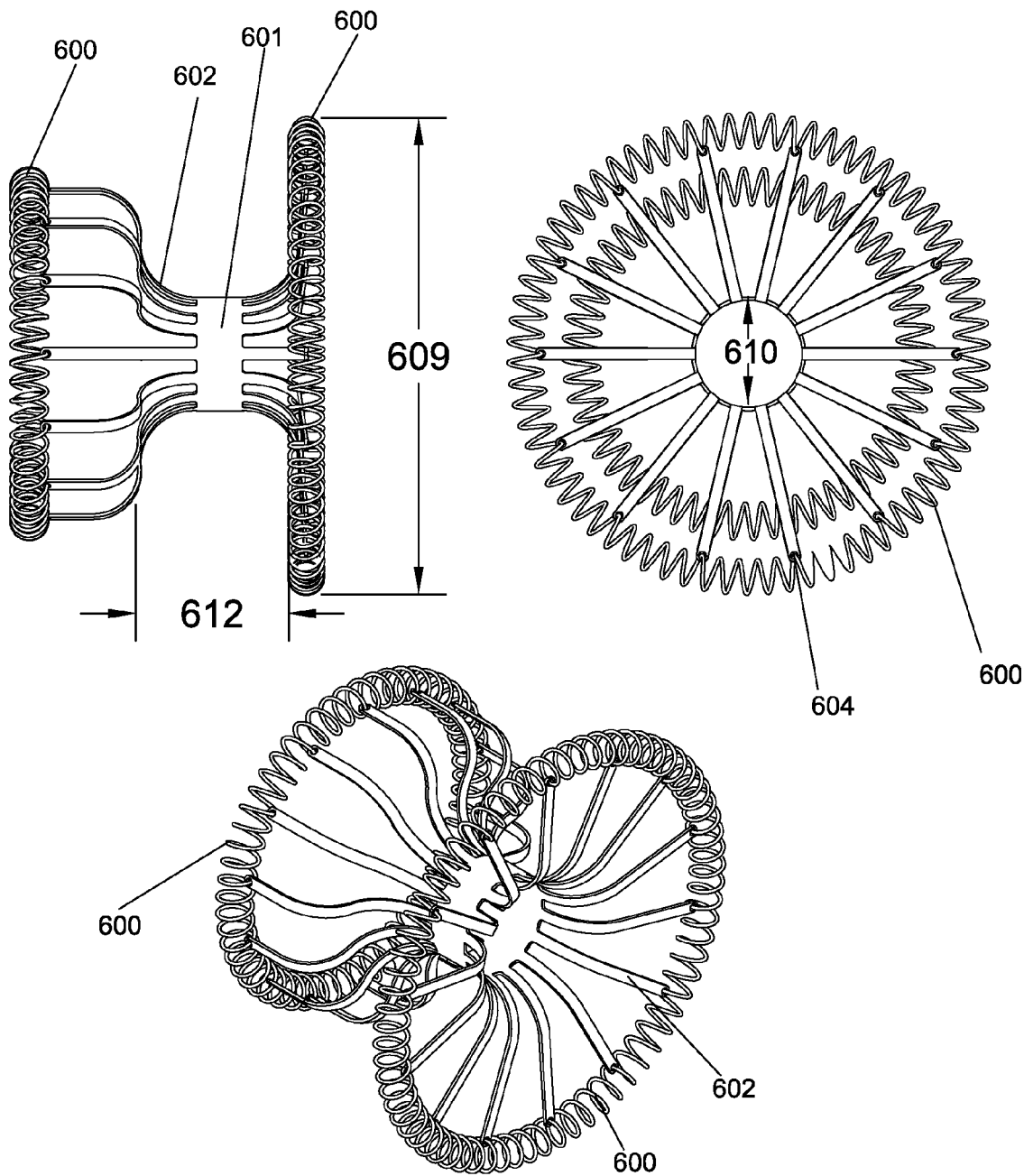
FIG. 21 is a drawing of an alternative embodiment of an expandable anchor. The expandable anchor is comprised of two toroidally shaped wound springs connected to a central cylinder by control arms.

FIG. 21 is a drawing of an alternative embodiment of an expandable anchor. The expandable anchor provides for an anchoring means to hold an intestinal bypass sleeve 111 within the small intestine. The expandable anchor is comprised of two toroidally shaped wound springs 600 connected to a central cylinder 601 by control arms 602. The toroidal springs 600 are prewound in a straight configuration and then the springs 600 are wound through the eyelets 604 on the end of the control arms and formed into the toroidal shape. The expandable anchor can be noncovered or it can have a polymer covering on the outside and inside as disclosed in FIG. 16. The spring ends are joined together at a spring joiner 614 (shown in FIG. 7). The spring ends may be fastened to the spring joiner 614 by mechanical means or they may be laser welded to the spring joiner 614. The spring joiner serves two purposes, to provide for a means of spring end termination and joining of the two spring ends and also provides for an exit point for the drawstring 605 to exit the spring 600. The drawstring 605 (shown in FIG. 7) is fed through the central axis of the toroidal spring 600. The two ends of the drawstring 605 both exit the spring joiner 614 and are terminated at ball 606. Pulling on the ball 606 and drawing the drawstring 605 through the spring joiner 614 causes the diameter of the spring 600 to be reduced and the control arms to bend and deflect as shown in FIG. 15. The drawstring 605 can also be terminated in loop 607 or with two balls spaced apart 608.

The toroidal springs are further disclosed in FIG. 12 and FIG. 13. The central cylinder and the control arms of the exemplary embodiment are laser cut from a piece of Nitinol tubing. In the exemplary embodiments, the expandable anchor is designed to allow the anchor to be of a self-expanding design. A self-expanding anchor design can be compressed in diameter to allow the device to be compressed in diameter to be loaded onto a delivery catheter. The anchor can then recover elastically to the original starting diameter, with the anchor diameter decreasing only a small amount due to nonelastic recovery. The anchor can also be made of a plastically deformable design and require a mechanical force applied to it in the radial or longitudinal direction to accomplish the expansion of the anchor. The mechanical force can be accomplished with an inflatable balloon type device, radially expanding the anchor or it may also be accomplished by a longitudinal compression of the anchor by a screw type mechanism or cable tensioning means. As shown, the anchor has a distal disk and a proximal disk that is comprised of 14 control arms on each portion. According to various embodiments, the anchor could have from 3 to 72 control arms for the proximal disk and the distal disk.

According to exemplary embodiments, the central cylinder 601, control arms 602 and springs 600 are made from a nickel titanium alloy (Nitinol). Other alternative suitable alloys for manufacturing the central cylinder 601, control arms 602 and springs 600 are stainless steel alloys: 304, 316L, BioDur® 108 Alloy, Pyromet Alloy® CTX-909, Pyromet® Alloy CTX-3, Pyromet® Alloy 31, Pyromet® Alloy CTX-1, 21 Cr-6Ni-9Mn Stainless, Pyromet Alloy 350, 18Cr-2Ni-12Mn Stainless, Custom 630 (17Cr-4Ni) Stainless, Custom 465® Stainless, Custom 455® Stainless, Custom 450® Stainless, Carpenter 13-8 Stainless, Type 440C Stainless, cobalt chromium alloys—MP35N, Elgiloy, L605, Biodur® Carpenter CCM alloy, Titanium and titanium alloys, Ti-6Al-4V/ELI and Ti-6Al-7Nb, Ti-15Mo, Tantalum, Tungsten and tungsten alloys, pure platinum, platinum-iridium alloys, platinum-nickel alloys, niobium, iridium, conichrome, gold and gold alloys. The anchor 110 may also be comprised of the following absorbable metals: pure iron and magnesium alloys. The central cylinder 601, control arms 602 and springs 600 may also be comprised of the following plastics: Polyetheretherketone (PEEK), polycarbonate, polyolefins, polyethylenes, polyether block amides (PEBAX), nylon 6, 6-6, 12, Polypropylene, polyesters, polyurethanes, polytetrafluoroethylene (PTFE) Poly(phenylene sulfide) (PPS), poly(butylene terephthalate) PBT, polysulfone, polyamide, polyimide, poly(p-phenylene oxide) PPO, acrylonitrile butadiene styrene (ABS), Polystyrene, Poly(methyl methacrylate) (PMMA), Polyoxymethylene (POM), Ethylene vinyl acetate, Styrene acrylonitrile resin, Polybutylene. The anchor, according to exemplary embodiments, is laser cut from a round tubing or from a flat sheet of Nitinol and then is rolled into a cylindrical shape after laser cutting. The anchor, according to exemplary embodiments, is made from a Nitinol tube of about 9 mm outside diameter by a wall thickness of 0.012 inch thick. Alternatively a starting tube is outside diameter can range from about 2 mm to 16 mm. An alternative construction method is to laser cut or chemical etch the pattern from a flat sheet of Nitinol with a thickness of 0.002 inch to 0.020 inch.

According to various embodiments, the anchor has an inside diameter 610 in the range of about 2 mm to 20 mm, anchor has a disk-shaped feature and a cup that has a diameter 609 in the range of about 20 mm to 66 mm. Anchor has a central cylinder 601 that has an outside diameter in the range of 4 mm to 20 mm. Central cylinder section 601 can have a length 612 of about 1 mm to 30 mm and is close to the width of the pylorus 106. The disks can have a length 611 of 1 mm to 10 mm. The cup shape portion can have a length of 1 mm to 50 mm. The central cylinder 601, in various embodiments, is made from a material having a stiffness sufficient to resist compressive forces applied by the pylorus.

Figure 22:
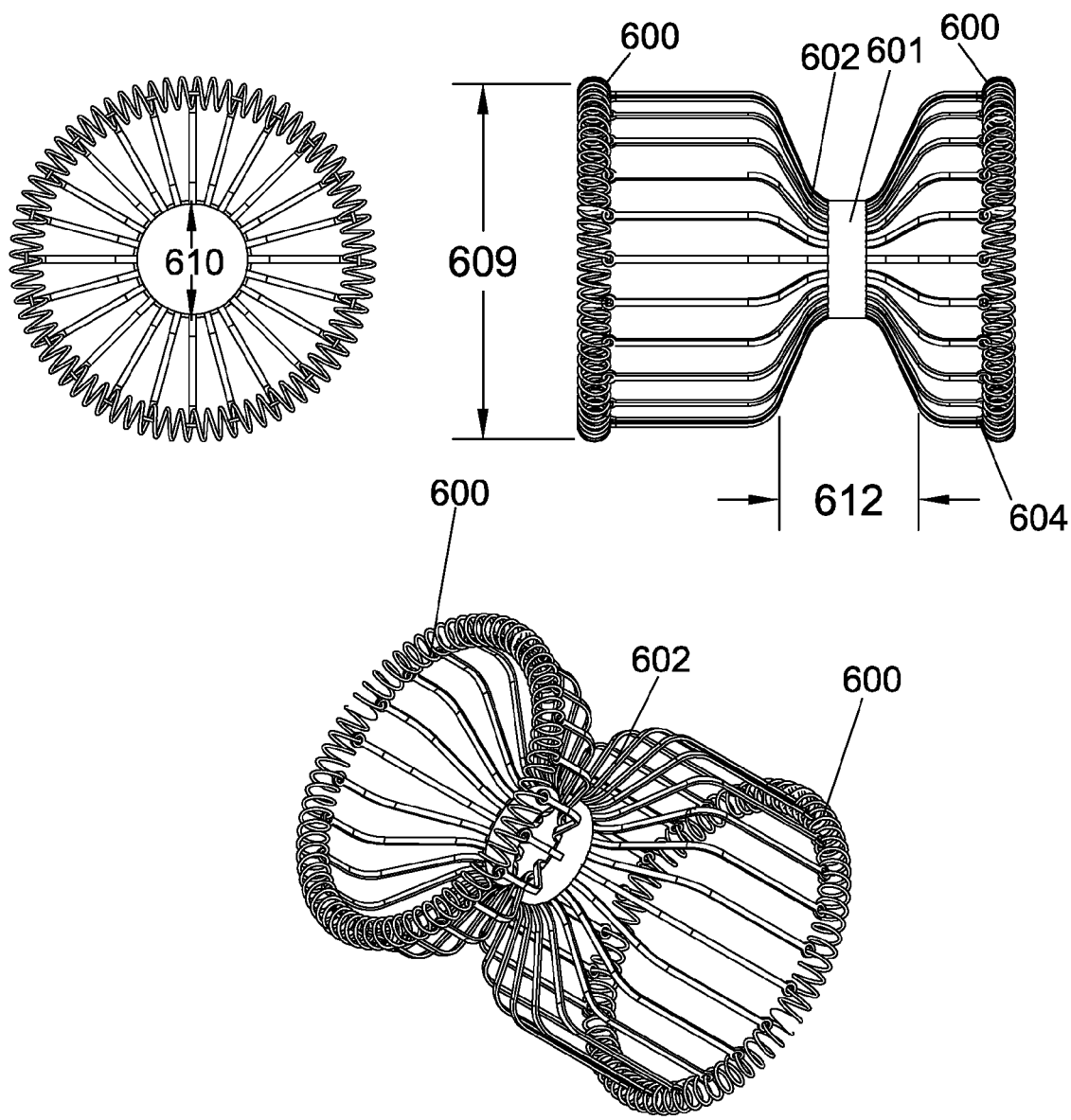
FIG. 22 is a drawing of an alternative embodiment of an expandable anchor. The expandable anchor is comprised of two toroidally shaped wound springs connected to a central cylinder by control arms.

FIG. 22 is a drawing of an alternative embodiment of an expandable anchor. The expandable anchor provides for an anchoring means to hold an intestinal bypass sleeve 111 within the small intestine. The expandable anchor is comprised of two toroidally shaped wound springs 600 connected to a central cylinder 601 by control arms 602. The toroidal springs 600 are prewound in a straight configuration and then the springs 600 are wound through the eyelets 604 on the end of the control arms and formed into the toroidal shape. The expandable anchor can be noncovered or it can have a polymer covering on the outside and inside as disclosed in FIG. 16. The spring ends are joined together at a spring joiner 614 (shown in FIG. 7). The spring ends may be fastened to the spring joiner 614 by mechanical means or they may be laser welded to the spring joiner 614. The spring joiner serves two purposes, to provide for a means of spring end termination and joining of the two spring ends and also provides for an exit point for the drawstring 605 to exit the spring 600. The drawstring 605 (shown in FIG. 7) is fed through the central axis of the toroidal spring 600. The two ends of the drawstring 605 both exit the spring joiner 614 and are terminated at ball 606 (shown in FIG. 7). Pulling on the ball 606 and drawing the drawstring 605 through the spring joiner 614 causes the diameter of the spring 600 to be reduced and the control arms to bend and deflect as shown in FIG. 15. The drawstring 605 can also be terminated in loop 607 or with two balls spaced apart 608.

According to various embodiments, anchor has an inside diameter 610 in the range of about 2 mm to 20 mm, the anchor has two cup shaped features that have a diameter 609 in the range of about 20 mm to 65 mm. The cup shape portions can have a length of 3 mm to 50 mm. Anchor has a central cylinder 601 that has an outside diameter in the range of 4 to 20 mm. Central cylinder section 601 can have a length 612 of about 1 mm to 30 mm and is close to the width of the pylorus 106. The cup shape portions can have a length of 1 mm to 50 mm. The central cylinder 601, in various embodiments, is made from a material having a stiffness sufficient to resist compressive forces applied by the pylorus. The materials and processing of FIG. 22 is identical to that disclosed previously in FIG. 21.

FIG. 23 is a drawing of an alternative embodiment of an expandable anchor. The expandable anchor provides for an anchoring means to hold an intestinal bypass sleeve 111 within the small intestine. The expandable anchor is comprised of two toroidally shaped wound springs 600 connected to a central cylinder 601 by control arms 602. The toroidal springs 600 are prewound in a straight configuration and then the springs 600 are wound through the eyelets 604 on the end of the control arms and formed into the toroidal shape. The expandable anchor can be noncovered or it can have a polymer covering on the outside and inside as disclosed in FIG. 16. The spring ends are joined together at a spring joiner 614 (shown in FIG. 7). The spring ends may be fastened to the spring joiner 614 by mechanical means or they may be laser welded to the spring joiner 614. The spring joiner serves two purposes, to provide for a means of spring end termination and joining of the two spring ends, and also provides for an exit point for the drawstring 605 to exit the spring 600. The drawstring 605 (shown in FIG. 7) is fed through the central axis of the toroidal spring 600. The two ends of the drawstring 605 both exit the spring joiner 614 and are terminated at ball 606 (shown in FIG. 7). Pulling on the ball 606 and drawing the drawstring 605 through the spring joiner 614 causes the diameter of the spring 600 to be reduced and the control arms to bend and deflect as shown in FIG. 15. The drawstring 605 can also be terminated in loop 607 or with two balls spaced apart 608.

According to various embodiments, the anchor has an inside diameter 610 in the range of about 2 mm to 20 mm, the anchor has two cup shaped features that have a diameter 609 in the range of about 20 mm to 65 mm. The cup shape portions can have a length of 3 mm to 50 mm. The anchor has a central cylinder 601 that has an outside diameter in the range of 4 mm to 20 mm. The central cylinder section 601 can have a length 612 of about 1 mm to 30 mm and is close to width of the pylorus 106. The cup shape portions can have a length of 1 mm to 50 mm. The central cylinder 601, in various embodiments, is made from a material having a stiffness sufficient to resist compressive forces applied by the pylorus. The materials and processing of FIG. 23 is identical to that disclosed previously in FIG. 21. Expandable anchor in FIG. 23 has control arms which are joined at the outer end by connectors 634. The diamond shape pattern at connectors 634 opens and closes as the diameter of the expandable anchor changes.

Figure 24:
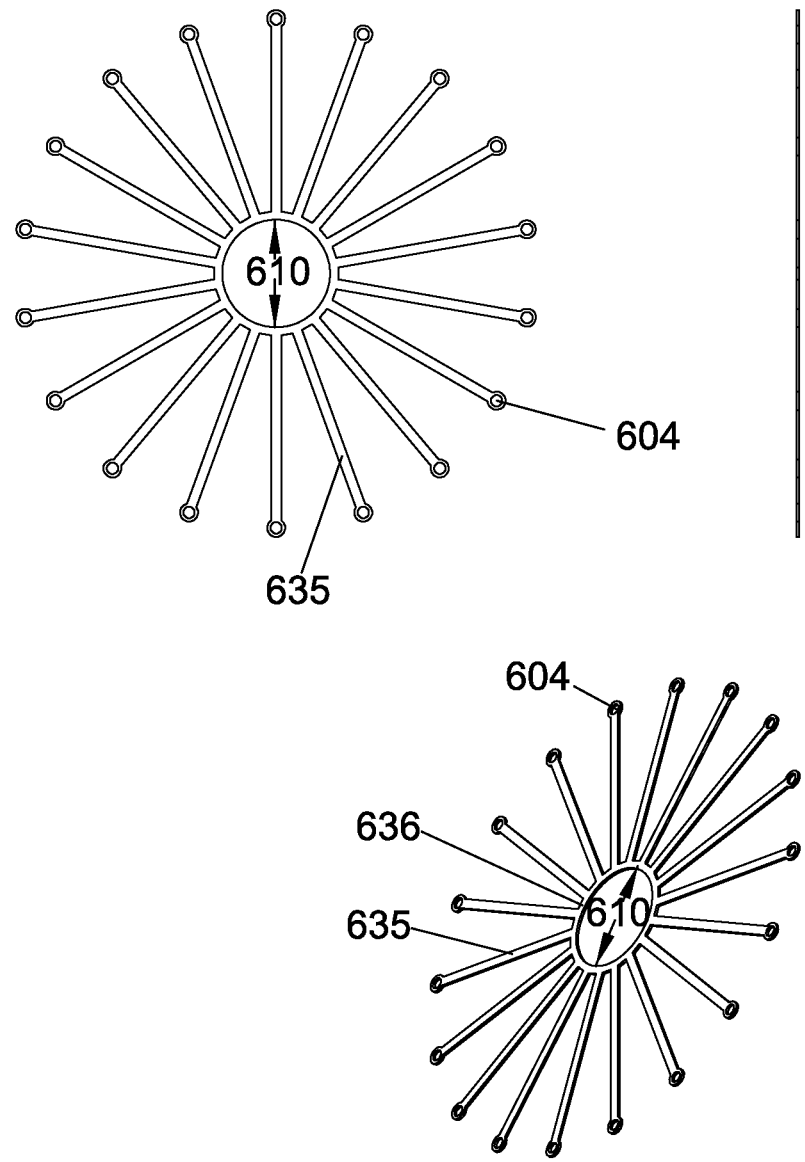
FIG. 24 is a drawing of an alternative embodiment of control arms.

FIG. 24 is a drawing of an alternative embodiment of control arms 635. The control arms 635 are laser cut from a flat sheet of Nitinol. The control arms are joined together at a central ring 636. The control arms 635 have holes 604 at the end of the arms. The diameter material and materials have been previously disclosed in FIG. 21.

Figure 25:
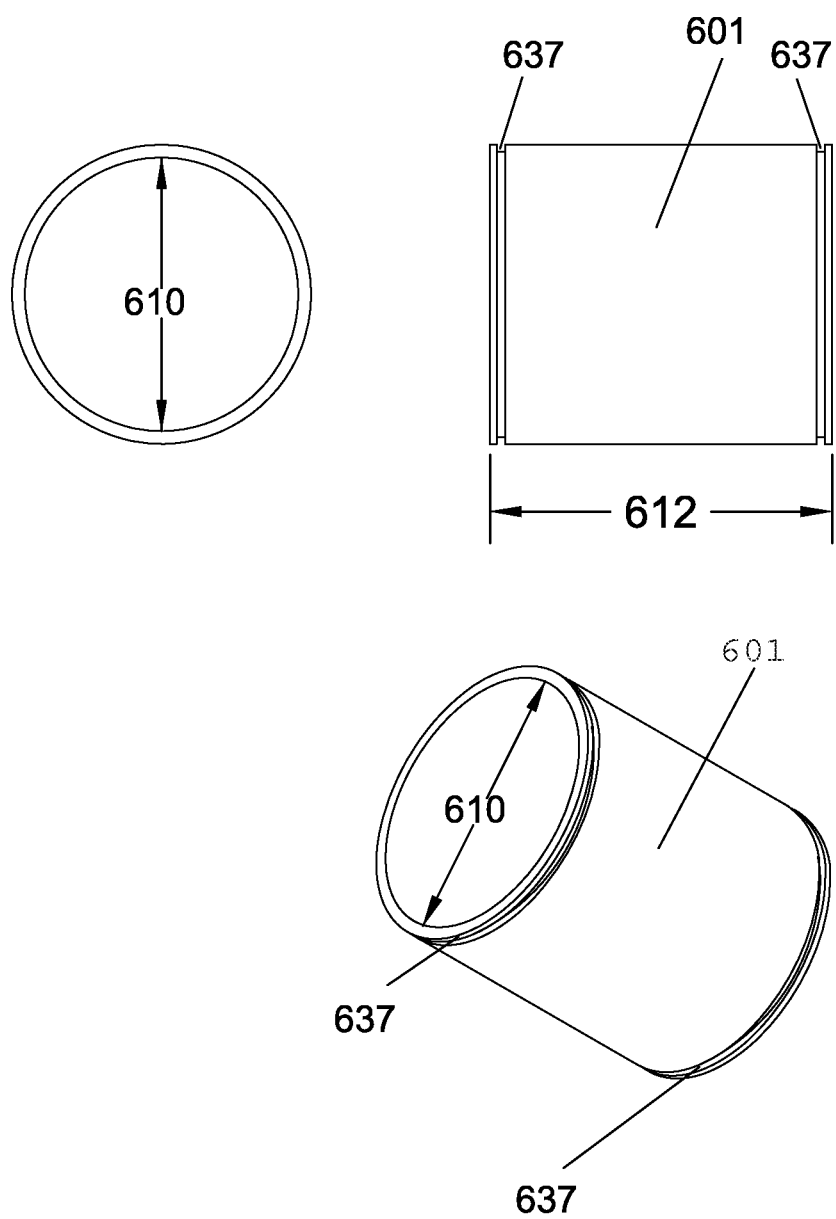
FIG. 25 is a drawing of an alternative embodiment of a central cylinder.

FIG. 25 is a drawing of an alternative embodiment of a central cylinder 601. The central cylinder 601 is made from a piece of metal or plastic tubing. The central cylinder has an annular groove on the outside diameter at each end to snap fit on the control arms from FIG. 25 into the annular groove. The central cylinder can be machined or molded and can be comprised of material previously disclosed in FIG. 7.

Figure 26:
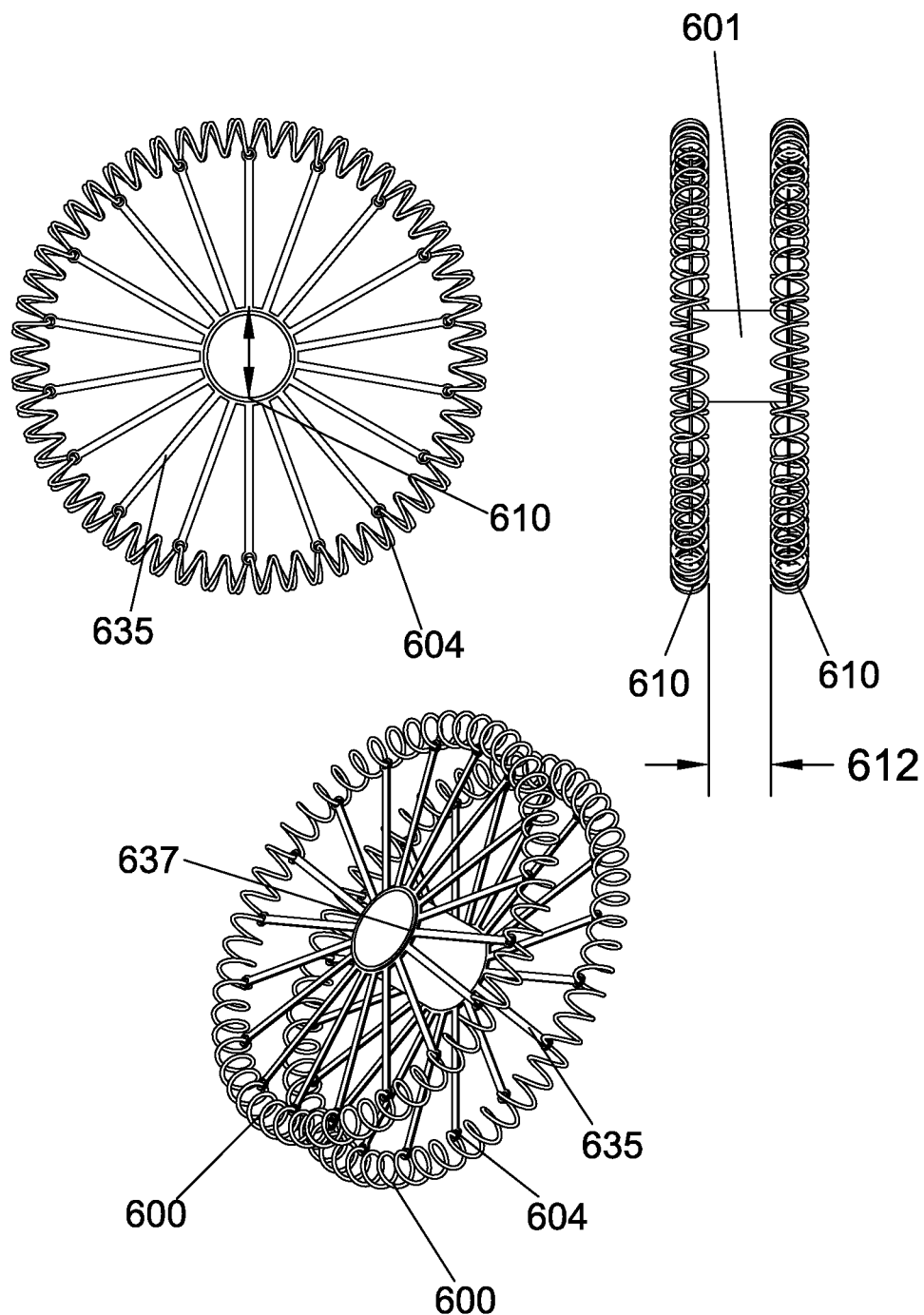
FIG. 26 is a drawing showing two pieces of FIG. 24 and FIG. 25 assembled together with two toroidal shaped springs.

FIG. 26 is a drawing of an expandable anchor assembly. The assembly is comprised of a control arm disk of FIG. 24, and a central cylinder of FIG. 25, assembled together with two toroidal shape springs 600. The control arm disk central ring 636 is elastically expanded in diameter and then snapped into annular groove 637 on the central cylinder. When the control arms 635 are bent towards the central cylinder 601, the central ring 636 rolls into the annular groove 637 and the central ring reverts and turns partially inside out as the control arms 635 deflect.

Figure 27:
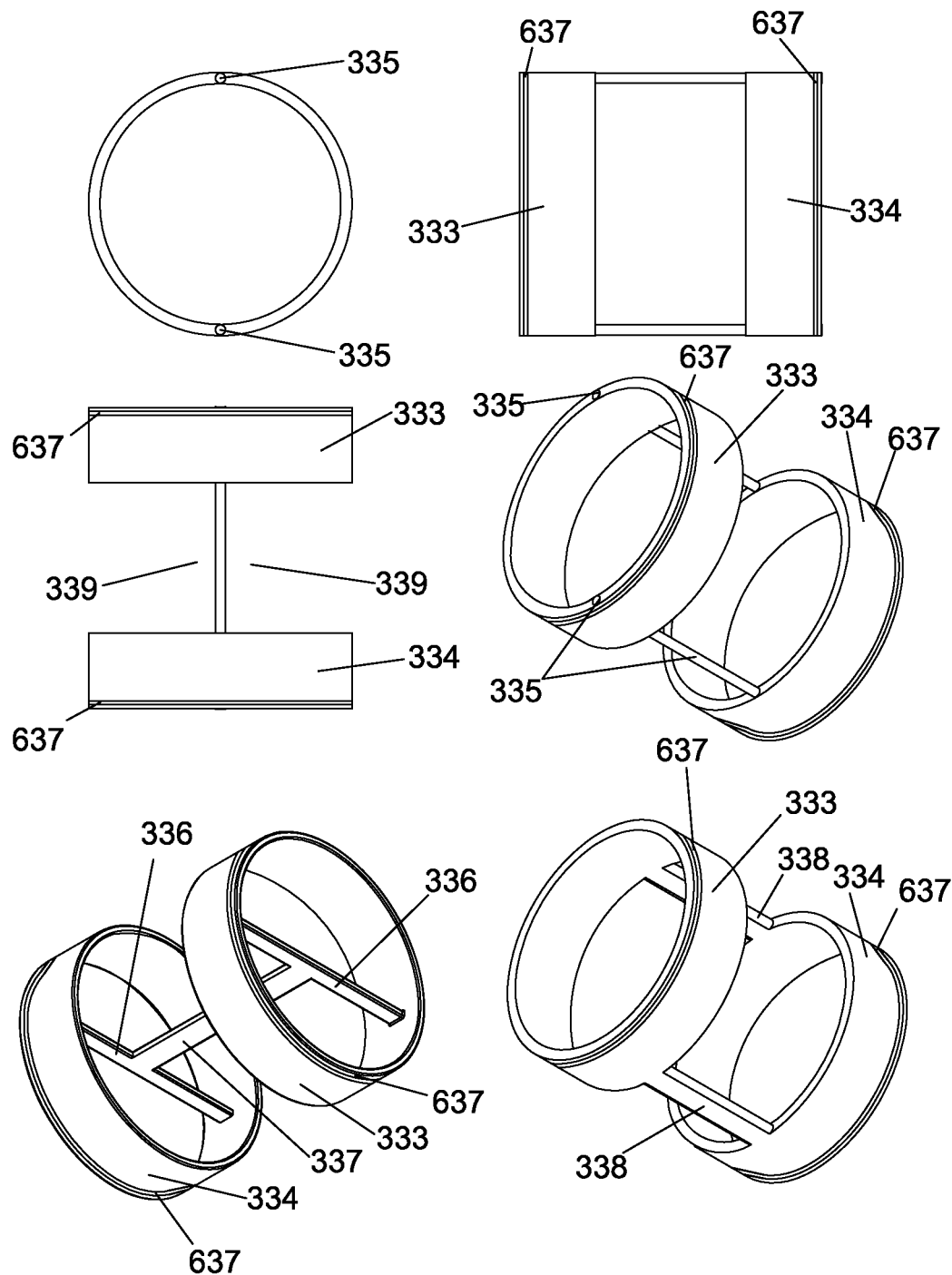
FIG. 27 is a drawing of alternative embodiments of a central cylinder.

FIG. 27 is drawing of a central cylinder pyloric portion for use with any of the anchor embodiments herein disclosed in which the mid-portion allows for normal opening and closing of the pylorus. There is a first ring 333 and a second ring 334 which are fixed rigidly together by connector links 335, 338 or 337. The central cylinder has an annular groove 637 on the outside diameter of the cylinder as previously disclosed in FIG. 25.

The connector links cross through the pyloric aperture 105 while not obstructing the pyloric aperture 105 or limiting opening or closing of the pylorus. In various embodiments, a thin polymeric membrane will be used over both rings 333 and 334 and will span the space between the two rings as disclosed in FIG. 26. The pylorus 106 can close by entering into the space 339 in between rings 333 and 334 to open and close. Rigid linking of rings 333 and 334 provides for a rigid structure to anchor expandable anchors to and helps to keep expandable anchor (disks) oriented in the proper orientation without canting within the pyloric antrum 104 or duodenal bulb 107. The rigid linking also does not allow rotational movement between the two rings 333 and 334 and still allows for normal opening and closing of the pylorus. Rotational movement between 333 and 334 may cause the pyloric polymer membrane portion to close. The expandable anchors in the pyloric antrum and the duodenal bulb are tethered to the first ring 333 and second ring 334 by a polymer membrane.

Figure 28:
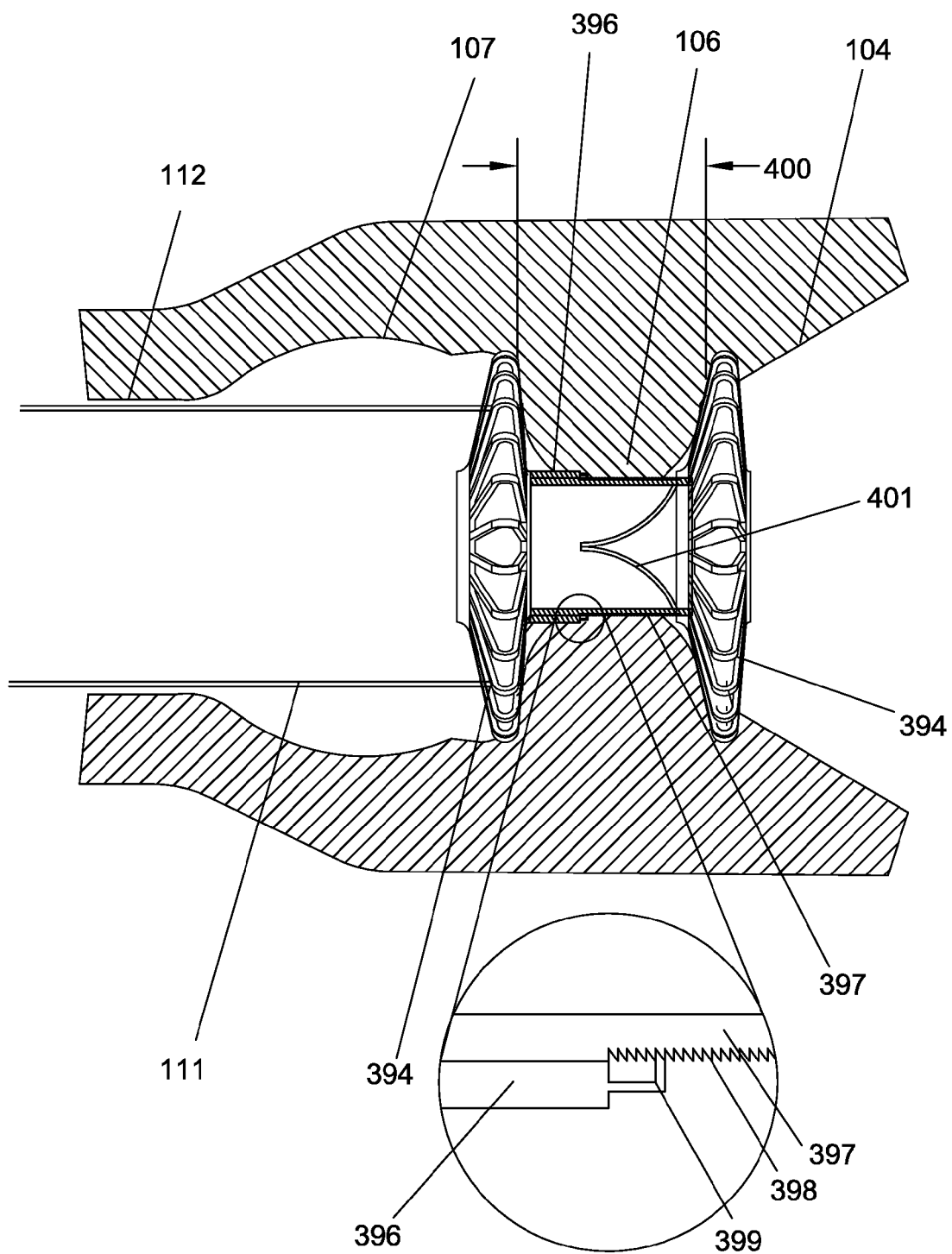
FIG. 28 is a drawing of an expandable anchor in which the central cylinder is adjustable in length.

FIG. 28 is a sectional view of the invention herein disclosed implanted into the pyloric antrum 104, pylorus 106, duodenal bulb 107 and duodenum 112. The anchoring device is comprised of two disk-shaped expandable anchors 394 that are connected to a central cylinder 396 and 397. Alternatively the disk can be constructed from a disk and toroidal springs as previously disclosed in FIG. 14 or FIG. 7. The central cylinder of the device 396 and 397 in between the two anchor rings 394 can be made from plastic material such as Delrin, PEEK, high density polyethylene, polycarbonate or other suitable polymer. The central cylinder portion 396 and 397 may also be made from stainless steel, titanium or Nitinol. The fixed diameter of the pyloric portion pieces 396 and 397 of the device can be sized to provide for a full opening of the pylorus and not allow the pylorus to close normally. The length of the pyloric portion of the device 400 can be adjusted by sliding the outer cylinder 396 over inner cylinder 397 by sliding on the ratcheting mechanism. This will change the spacing between the anchor rings 394 and will allow the device to be adjusted for ring spacing in-situ. It may be desirable to change the ring spacing to accommodate differences in the pylorus 106 dimensions from patient to patient. It may also be desirable to change the length 400 of the central cylinder portion to allow the anchor ring 394 spacing to be adjusted to allow the expandable anchor to put a clamping force on to the pylorus in a longitudinal direction. The mechanism used for 398 and 399 could also be a screw thread arrangement such as a male thread on 398 and a female thread on 399. In various embodiments, the inside diameter of the central cylinder 396 and 397 ranges from as small as 2 mm in diameter up to as large as 14 mm in diameter. The central lumen of the device has a one-way, anti-reflux valve 401. The anti-reflux valve 401 allows for unobstructed flow in the direction of the pyloric antrum 104 to the duodenal bulb 107, but limits flow in the reverse direction. The anti-reflux valve 401 can be constructed of a duck bill design with two flexible leaflets, or may utilize other designs such as a tri-leaflet valve or quad-leaflet valve. The anti-reflux valve may be constructed of silicone, polyurethane, polyethylene, ePTFE or other suitable polymer. The diameter of the central cylinder is fixed, but it may also be designed to allow it to be reduced in diameter during loading of the device onto a catheter.

Figure 29:
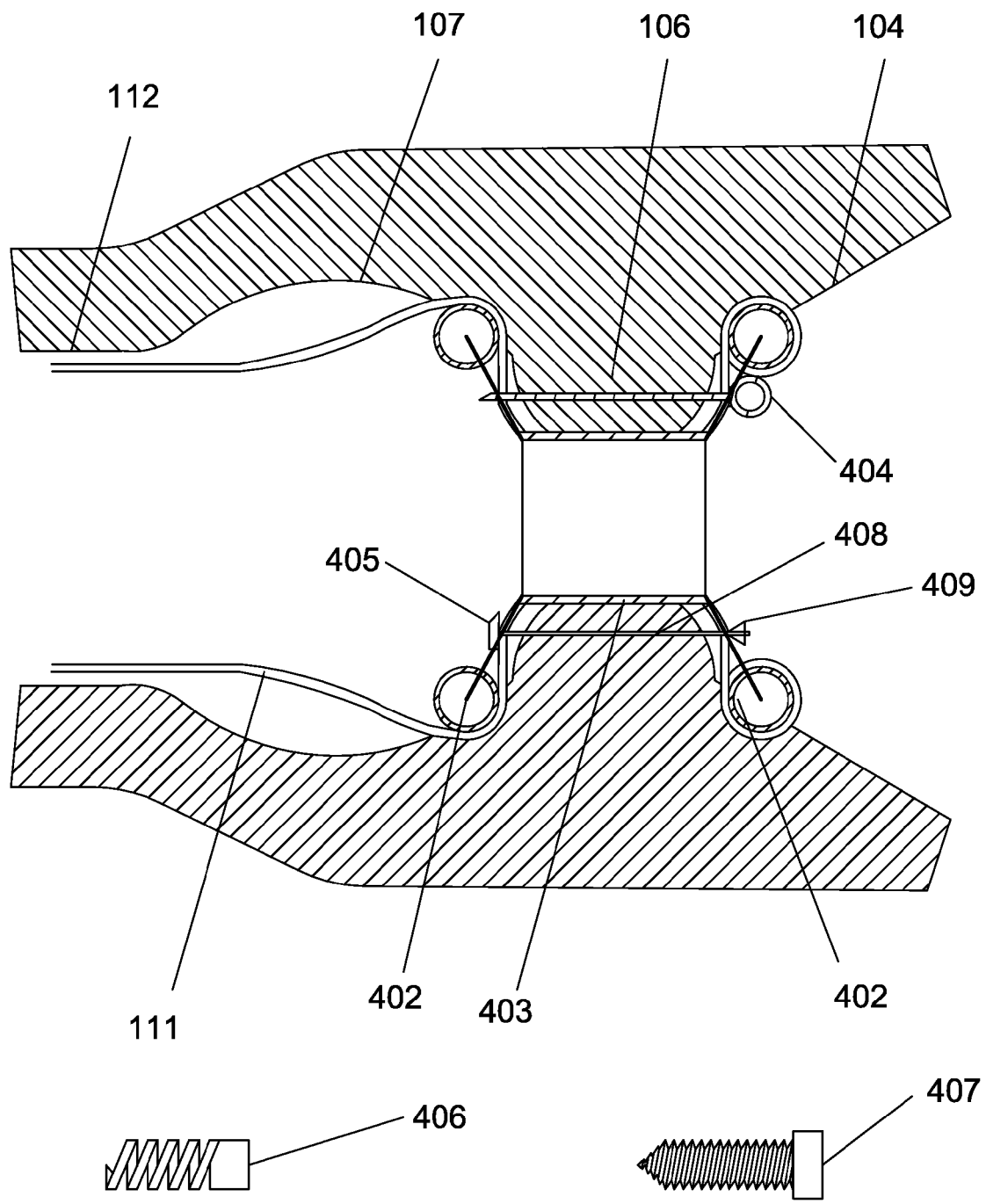
FIG. 29 is a drawing of an expandable anchor as herein disclosed in which the expandable anchor is secondarily anchored to the pylorus, duodenal bulb or pyloric antrum by secondary means.

FIG. 29 is a sectional view of the invention herein disclosed implanted into the pyloric antrum 104, pylorus 106 and duodenal bulb 107 and duodenum 112. The anchoring device is comprised of two toroidal-shaped expandable anchors 402 that are connected to a central cylinder 403. Alternatively the disk can be constructed from a disk and toroidal springs as previously disclosed in FIG. 14 or FIG. 7. The diameter of the central cylinder 403 is fixed, but it may also be elastic to allow it to be reduced in diameter during loading of the device onto a catheter. An optional needle 404, suture, T-bar 405, hollow helical anchor 406 or screw type anchor 407 is inserted into and/or through the tissue of the pylorus 106, pyloric antrum 104 or duodenum 107 to provide additional anchoring and securement of the intestinal bypass sleeve 111 anchoring device to the pylorus 106 anatomy. The T-bar 405 is anchored by a tensioning member 408 and cincher 409.

Figure 30:
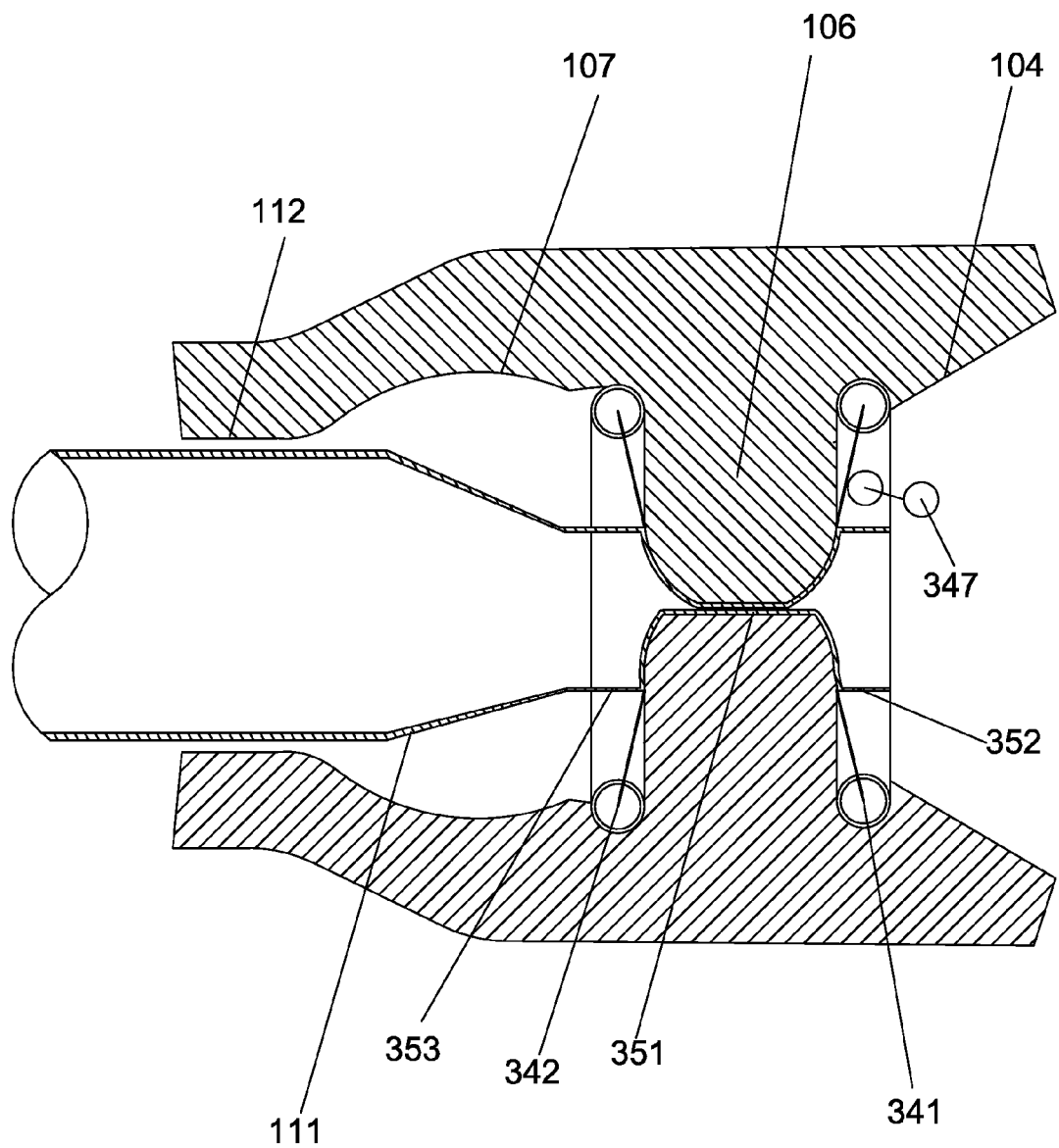
FIG. 30 is a drawing of an expandable anchor in which portion of the central cylinder is soft and conformable and allows the pylorus to open close with the membrane on the central cylinder.

FIG. 30 is a sectional view of the invention herein disclosed implanted into the pyloric antrum 104, pylorus 106, duodenal bulb 107 and duodenum 112. The anchoring device is comprised of two disk-shaped expandable anchors 341 and 342 as previously disclosed in this application that are connected to rings 352 and 353. Alternatively the disk can be constructed from a disk and toroidal springs as previously disclosed in FIG. 14 or FIG. 7.

The rings 352 and 353 are not rigidly connected to each other. Thin-walled central membrane 351 is connected to the two rings 352 and 353. Central membrane can open and close with the pylorus. Drawstring 347 can be tensioned to collapse the diameter of the expandable anchors for removal and for loading the device onto a delivery catheter.

Figure 31:
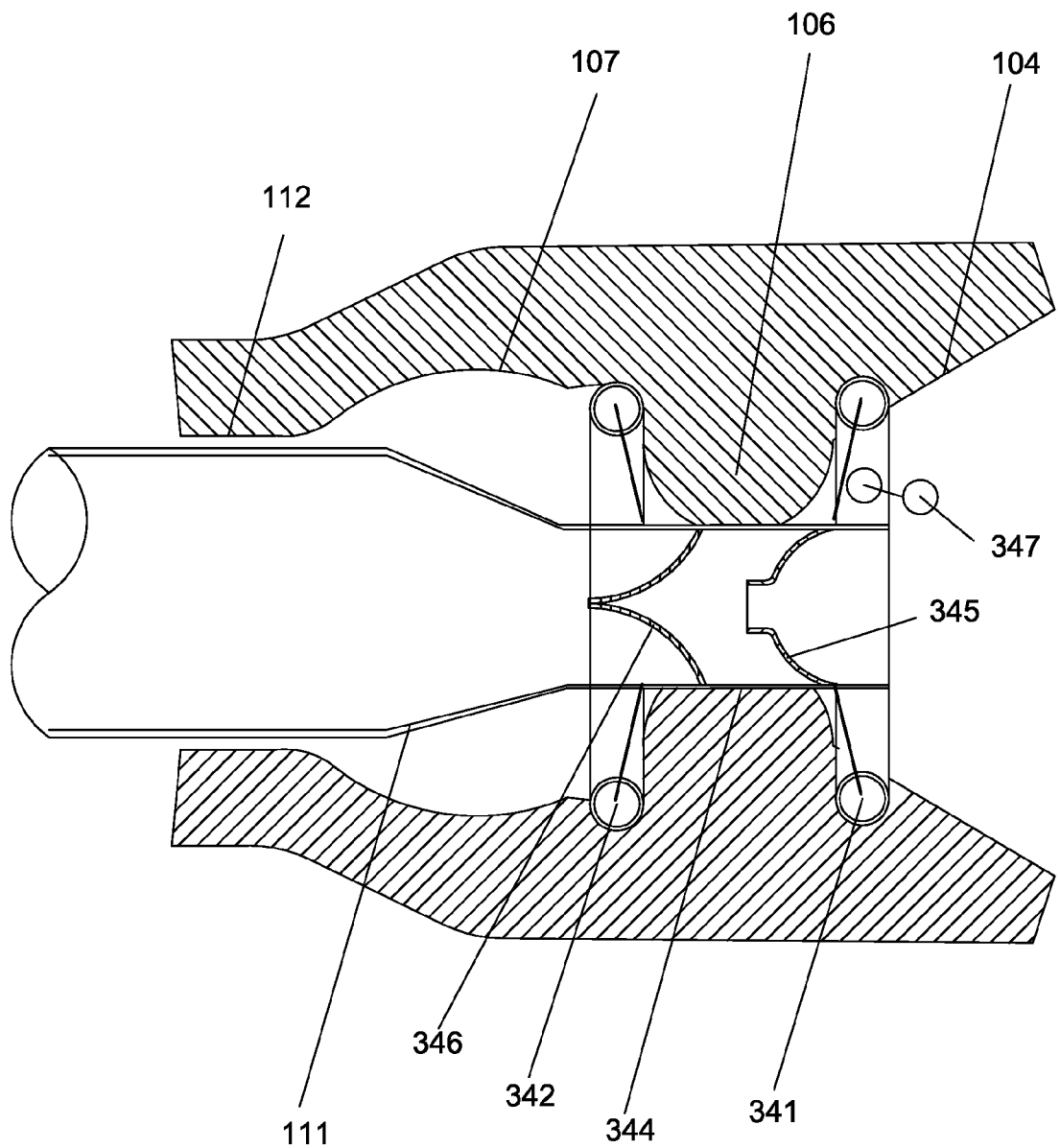
FIG. 31 is a drawing of an expandable anchor and an intestinal bypass sleeve. An optional anti-reflux valve and restrictor valve have been incorporated into the central cylinder.

FIG. 31 is a sectional view of the invention herein disclosed implanted into the pyloric antrum 104, pylorus 106, duodenal bulb 107 and duodenum 112. The anchoring device is comprised of two disk-shaped expandable anchors 341, 342 as previously disclosed in this application that are connected to a rigid central cylinder 344. The disk can be constructed from a disk and toroidal springs as previously disclosed in FIG. 14 or FIG. 7.

The lumen of the anchoring device has a one way anti-reflux valve 346 and a flow limiter 345. Drawstring 347 can be tensioned to collapse the diameter of the expandable anchors for removal and for loading the expandable anchor onto a delivery catheter.

Figure 32:
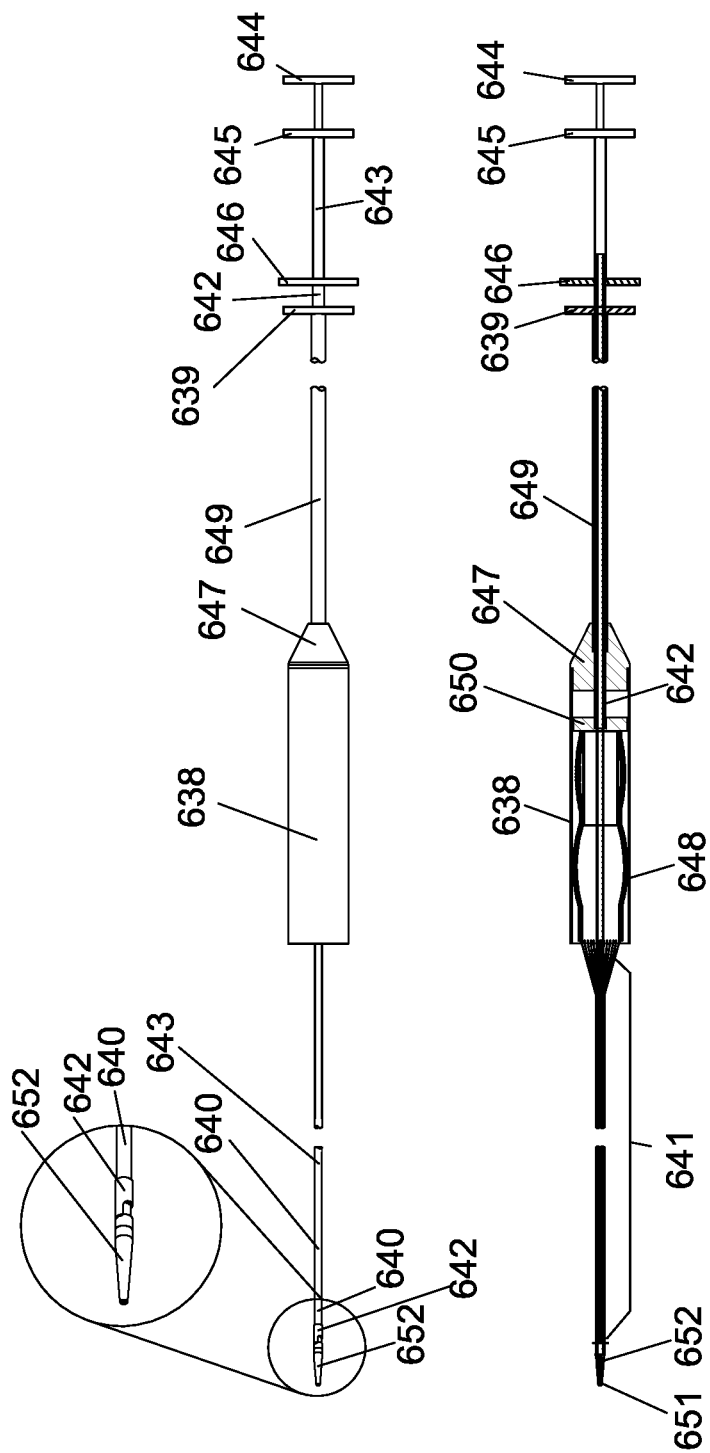
FIG. 32 is a drawing of an over the wire delivery catheter for placing the expandable anchor and intestinal bypass sleeve within the digestive tract.

FIG. 32 is a cross-sectional drawing of a delivery catheter for the invention herein disclosed. The delivery catheter is comprised of: distal outer capsule 638, which transitions down to a smaller diameter at the proximal outer sheath 649, proximal pusher catheter 642, sleeve delivery catheter outer tube 643, sleeve delivery catheter inner tube 642. There are four handles on the catheter: outer sheath handle 639, proximal pusher handle 646, sleeve delivery catheter outer tube 645 and sleeve delivery catheter inner tube 644. The implant pusher disk 650 serves as a mechanical stop or means to hold stationery or push out the expandable anchor 648 or implant from the inside of the distal outer capsule 638. The distal tip 652 provides for a flexible tip that will track over a guide wire. The guide wire may be inserted through the sleeve delivery catheter central lumen 651. Expandable anchor 648 and the intestinal bypass sleeve 641 are compressed and loaded onto the delivery catheter. The intestinal bypass sleeve 641 extends out beyond the end of the distal outer capsule 638. The sleeve delivery catheter 640 is coaxially inside the lumen of the intestinal bypass sleeve 641 and mechanically retains the intestinal bypass sleeve to the end of the sleeve delivery catheter. Capsule connector 647 joins the distal outer capsule 638 to the proximal outer sheath 649.

The distal outer capsule 638 may be made from a plastic polymer such as Pebax® (polyether block amide), Hytrel (polyester elastomer), nylon 12, nylon 11, nylon 6, nylon 6,6, polyethylene, polyurethane or other suitable polymer. The distal outer sheath 638 may have an inner lining made from a polymer with a low coefficient of friction such as PTFE. The distal outer capsule 638 may also have a metal re-enforcement in the wall thickness to improve the kink resistance or burst properties of the outer sheath. The metal re-enforcement may be comprised of a braided wire mesh or a coil in the wall thickness. The metal used for the braid may be stainless steel, Nitinol, MP35N, L605, Elgiloy or other suitable material. The distal outer capsule 638 length may range from 1-2 inches in length up to full length of the catheter.

The proximal outer sheath 649 may be made from a plastic polymer such as Pebax® (polyether block amide), Hytrel (polyester elastomer), nylon 12, nylon 11, nylon 6, nylon 6,6, polyethylene, polyurethane or other suitable polymer. The proximal outer sheath 649 may have an inner lining made from a polymer with a low coefficient of friction such as PTFE. The proximal outer sheath 649 may also have a metal re-enforcement in the wall thickness to improve the kink resistance or burst properties of the outer sheath. The metal re-enforcement may be comprised of a braided wire mesh or a coil in the wall thickness. The metal used for the braid may be stainless steel, Nitinol, MP35N, L605, Elgiloy or other suitable material.

The proximal pusher catheter 642 may be made from a plastic polymer such as Pebax® (polyether block amide), PEEK, Hytrel (polyester elastomer), nylon 12, nylon 11, nylon 6, nylon 6,6, polyethylene, polyurethane, polyimide, PTFE, FEP or other suitable polymer. The proximal pusher catheter 642 may have an inner lining made from a polymer with a low coefficient of friction such as PTFE. The proximal pusher catheter 642 may also have a metal re-enforcement in the wall thickness to improve the kink resistance or burst properties of the outer sheath. The metal re-enforcement may be comprised of a braided wire mesh or a coil in the wall thickness. The metal used for the braid may be stainless steel, Nitinol, MP35N, L605, Elgiloy or other suitable material The sleeve delivery catheter 640 may be made from a plastic polymer such as Pebax® (polyether block amide), PEEK, Hytrel (polyester elastomer), nylon 12, nylon 11, nylon 6, nylon 6,6, polyethylene, polyurethane or other suitable polymer. The sleeve advancement pusher 172 may have an inner lining made from a polymer with a low coefficient of friction such as PTFE. The sleeve delivery catheter 640 may also have a metal re-enforcement in the wall thickness to improve the kink resistance or burst properties of the outer sheath. The metal re-enforcement may be comprised of a braided wire mesh or a coil in the wall thickness. The metal used for the braid may be stainless steel, Nitinol, MP35N, L605, Elgiloy or other suitable material. The sleeve delivery catheter 640 may have a hollow core to allow passage over a guide wire or it may be solid without an opening. The sleeve delivery catheter 640 may also be constructed of a simple tightly wound metal wire coil construction or it may be wound from multiple wires such as Hollow Helical Strand tube made by Fort Wayne Metals. The distal tip 652 may be molded from Pebax®, polyurethane, Hytrel, silicone or other suitable elastomer. The delivery catheter handles may be molded or machined from metal or plastic. The outer sheath handle 639 is attached to the proximal outer sheath 649. The outer sheath handle 639 is used to hold or retract the distal outer sheath 638 and the proximal outer sheath 649 during the advancement of the delivery catheter into the human anatomy, and while deploying of the expandable anchor.

Figure 33:
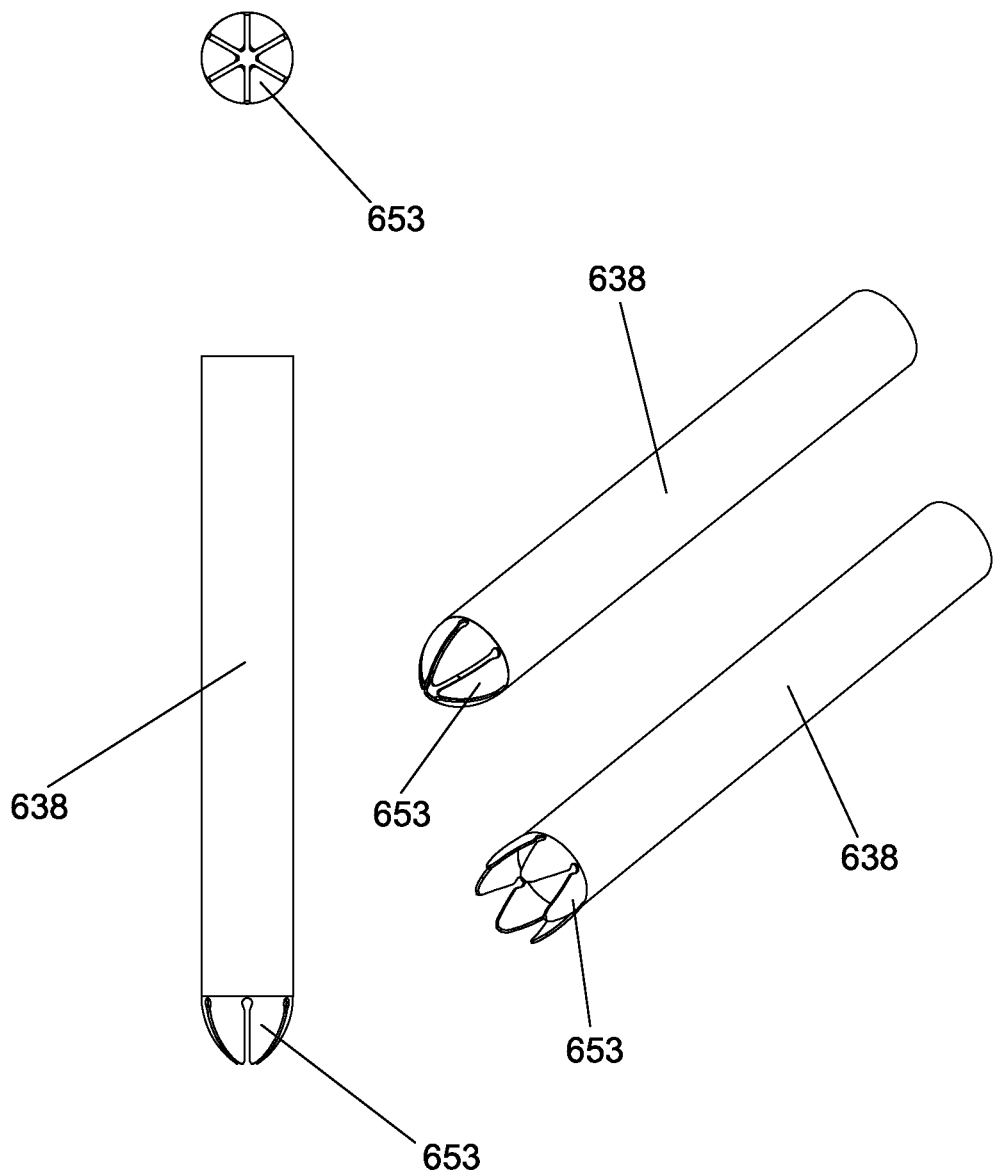
FIG. 33 is a drawing of a distal capsule tip for the delivery catheter as shown in FIG. 32.

FIG. 33 is an alternative embodiment of the distal outer capsule 638. The distal outer capsule has a formed tip 653 that has 6 leaflets that bend open to allow loading or deploying of the expandable anchor. The leaflets are preferably made from a plastic material such as PTFE or polyethylene. The leaflets are attached to the distal outer capsule 638 and can be made in a straight shape integral with the distal outer capsule 638 material and then heat formed into the final shape. The number of leafs can range from about 3 to 16.

Figure 34:
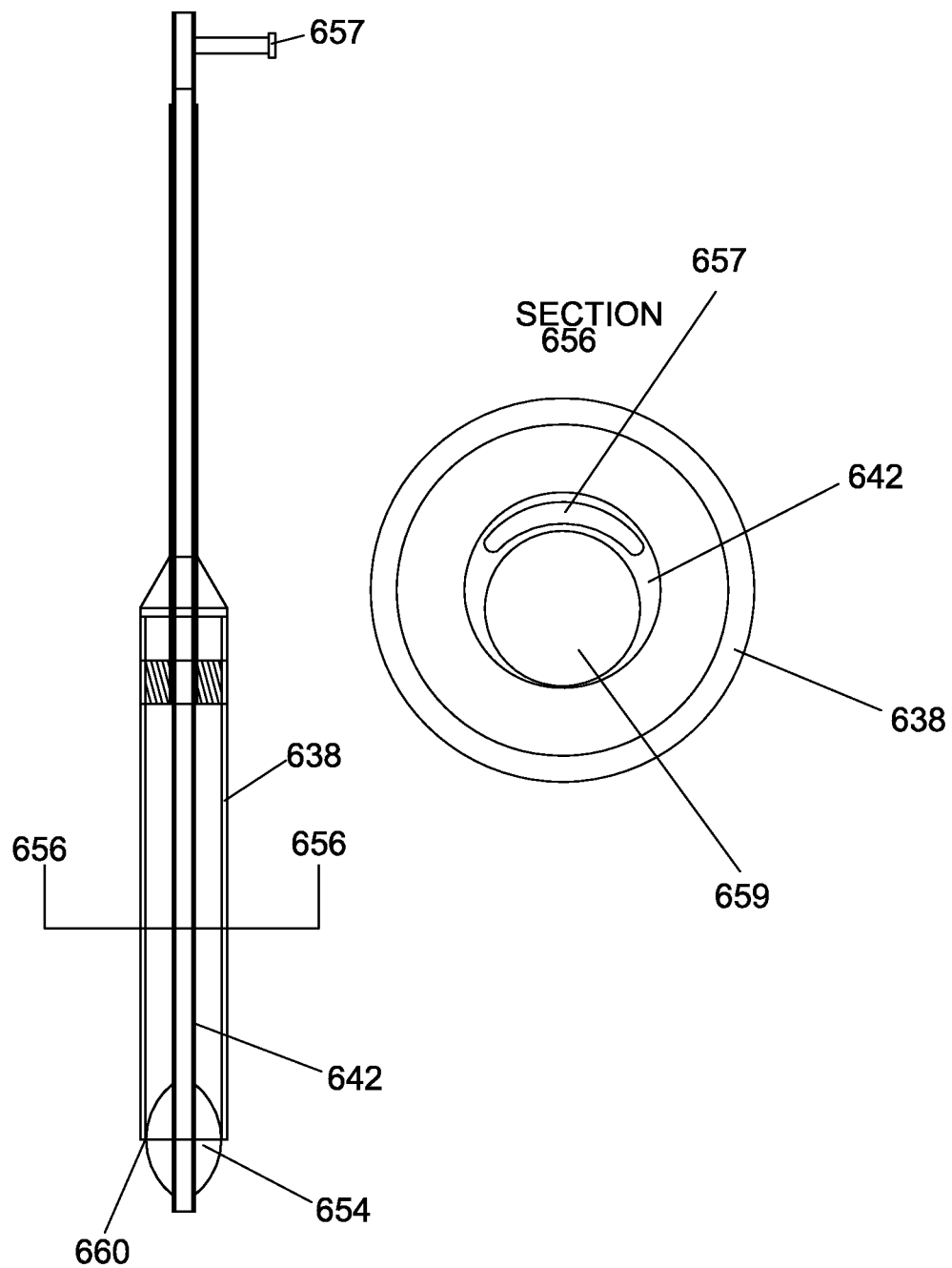
FIG. 34 is a drawing of an inflatable balloon tip for the distal capsule of the delivery device as shown in FIG. 32.

FIG. 34 is a drawing of an alternative embodiment of a tip for the inside diameter of distal outer capsule 638. Proximal pusher catheter 642 extends through the length of the distal capsule 638. Proximal pusher catheter 642 is a dual lumen tubing. The first lumen 659 is for advancement or retraction of the sleeve delivery catheter, the inflation lumen 657 is for inflating and deflating the inflatable balloon tip 654 bonded at the distal end of the pusher catheter 642. A thin wall compliant balloon tip 654 bonded onto the distal end of the proximal pusher catheter. The balloon tip 654 can be inflated or deflated through the side port 658 which is connected to the inflation lumen 657. The balloon tip 654 is inflated with air, CO2, water or saline after the expandable anchor and intestinal bypass sleeve have been loaded into the distal outer capsule. The intestinal bypass sleeve is compressed in between the annular space 660 between the inside diameter of the distal outer capsule 638 and the balloon tip 654.

Figure 35:
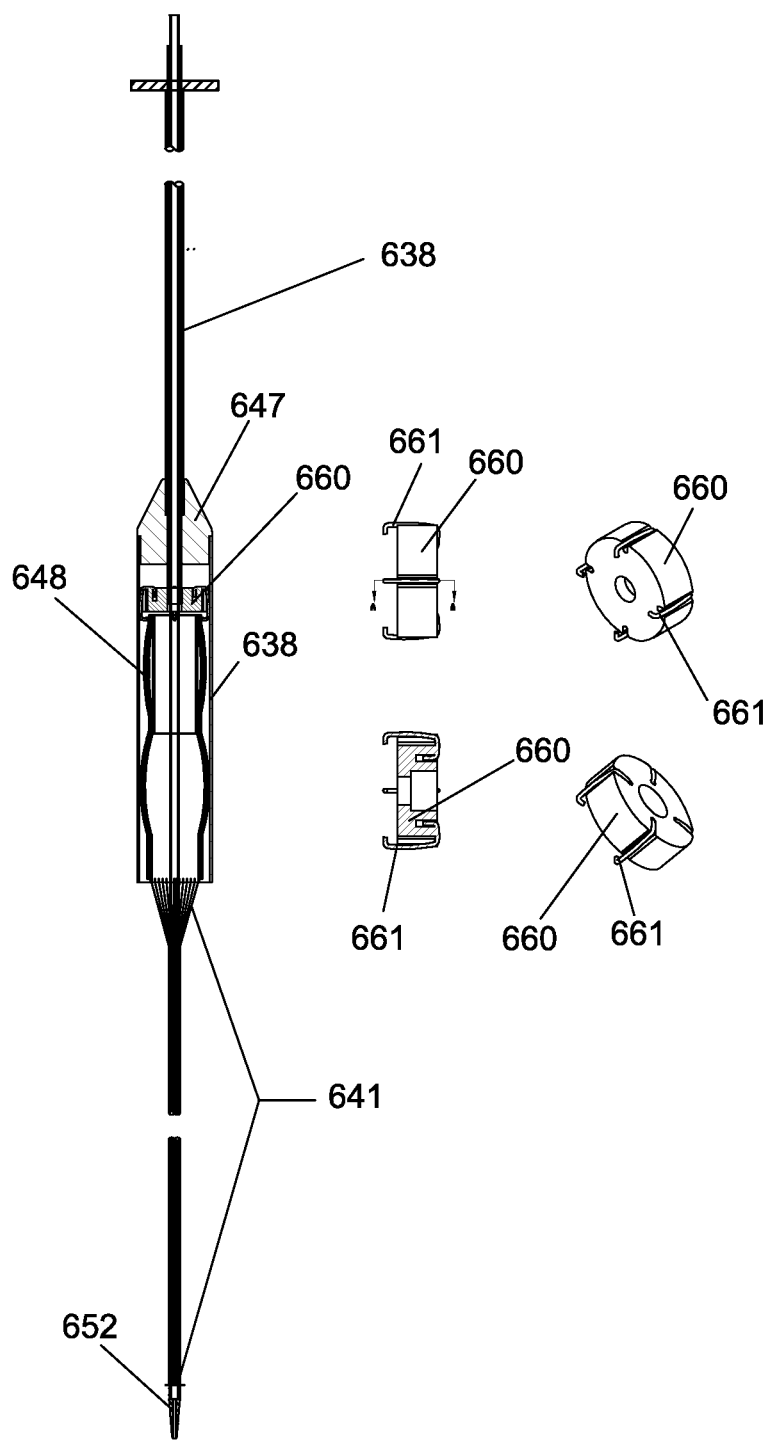
FIG. 35 is a drawing of a delivery catheter for placing the expandable anchor and intestinal bypass sleeve within the digestive tract. The delivery catheter has a retainer to prevent premature deployment of the expandable anchor and to allow it to be re-sheathed to adjust the placement location within the body.

FIG. 35 is a drawing of an alternative embodiment of the delivery catheter previously disclosed in FIG. 32. The implant pusher disk 650 as shown in FIG. 32 has been modified to incorporate a retention mechanism 660. Spring retainer arms 661 can engage with holes in the expandable anchor 648 central cylinder. The spring retainer arms 661 can securely hold the expandable anchor 648 and prevent the expandable anchor 648 from slipping out of the distal capsule and deploying prematurely before the expandable is in the proper implant location. The spring retainer arms 661 can also allow the distal capsule 638 to be advanced distally forward over a partially deployed expandable anchor 648 to resheath a partially deployed expandable anchor.

Figure 36:
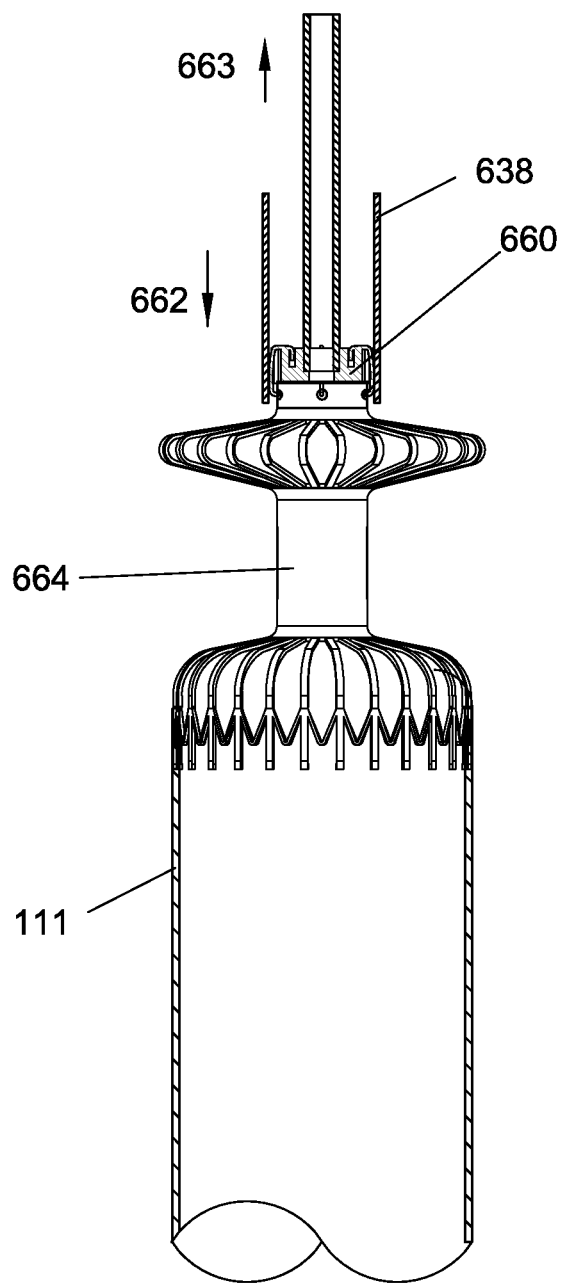
FIG. 36 is a drawing of a distal end of a delivery catheter and an expandable anchor and intestinal bypass sleeve.

FIG. 36 is a drawing of an expandable anchor 664 and an intestinal bypass sleeve 111 attached to a retention mechanism 660 on a deployment catheter. The distal outer sheath 638 is pushed in direction 662 while maintaining tension in the direction 663 will hold the expandable anchor in position while the distal outer capsule 638 is advanced distally over the expandable anchor 664 to re-collapse it.

Figure 37:
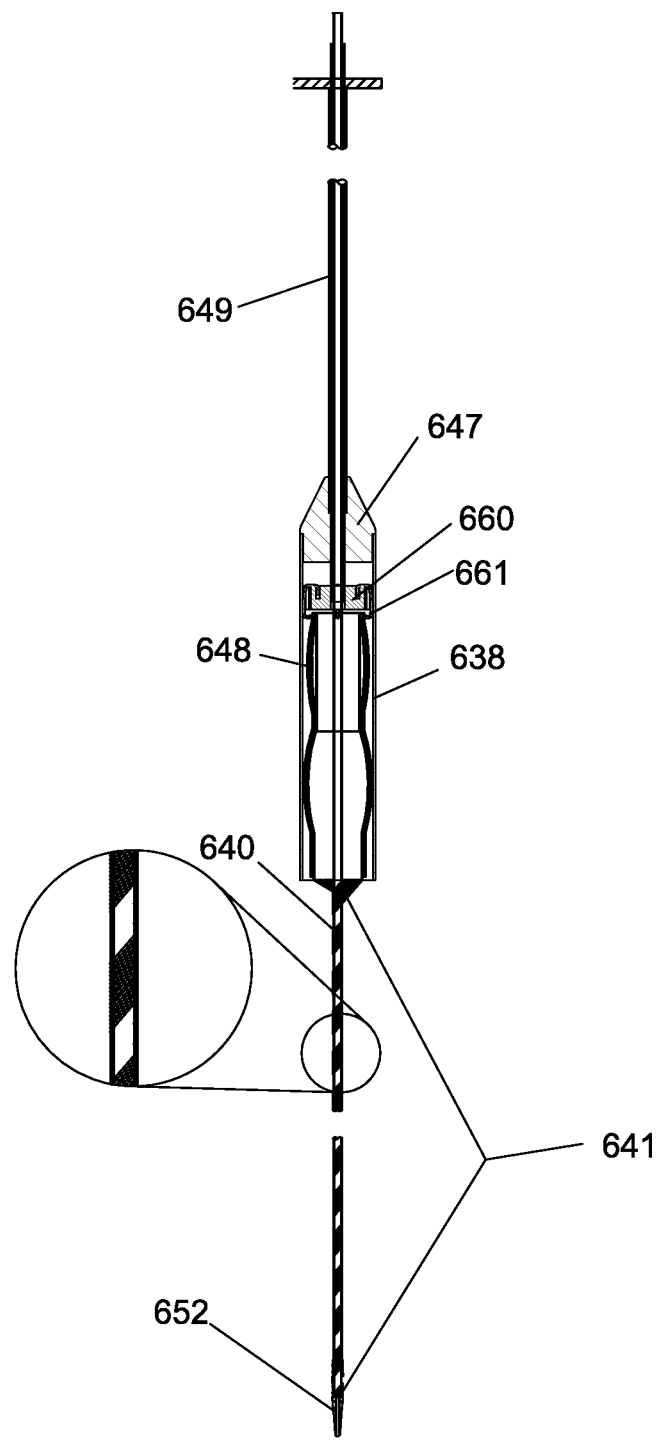
FIG. 37 is a drawing of a delivery catheter for placing the expandable anchor and intestinal bypass sleeve within the digestive tract.

FIG. 37 is a cross-sectional drawing of a portion of a delivery catheter for the invention as previously disclosed in FIG. 32. The catheter is identical to that disclosed in FIG. 32. The expandable anchor 648 and the intestinal bypass sleeve 641 are compressed and loaded onto the delivery catheter. The sleeve delivery catheter 640 is located coaxially inside the lumen of the intestinal bypass sleeve 641 and mechanically retains the intestinal bypass sleeve to the end of the sleeve delivery catheter. The intestinal bypass sleeve 641 is wrapped in a helical direction around the sleeve delivery catheter by rotating the sleeve delivery catheter within the distal outer capsule 638, while fixing the rotational position of distal outer capsule. This causes the intestinal bypass sleeve 641 to wrap down more compactly around the sleeve delivery catheter and reduces the delivery profile.

Figure 38:
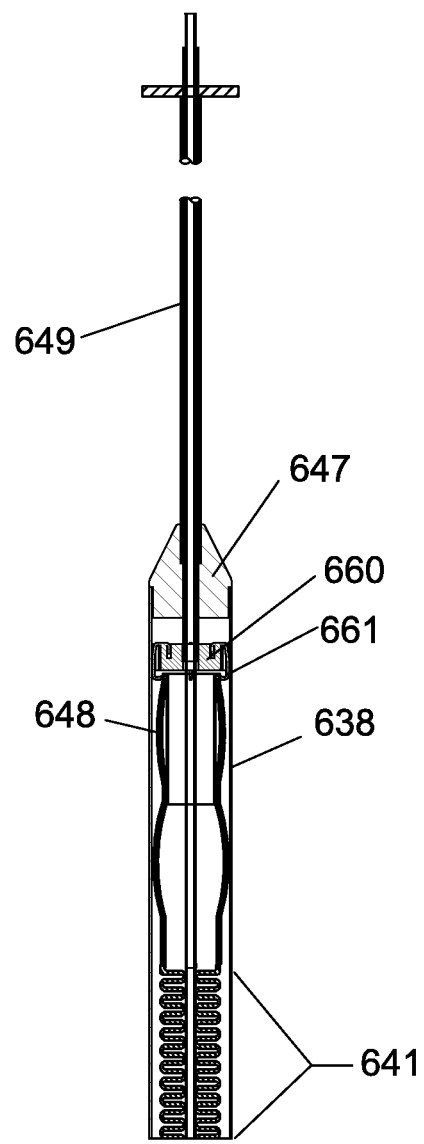
FIG. 38 is a drawing of a delivery catheter for placing the expandable anchor and intestinal bypass sleeve within the digestive tract.

FIG. 38 is a cross-sectional drawing of a portion of a delivery catheter for the invention as previously disclosed in FIG. 32. The catheter is identical to that disclosed in FIG. 32. The expandable anchor 648 and the intestinal bypass sleeve 641 are compressed and loaded onto the delivery catheter. The sleeve delivery catheter 640 is located coaxially inside the lumen of the intestinal bypass sleeve 641 and mechanically retains the intestinal bypass sleeve to the end of the sleeve delivery catheter. The intestinal bypass sleeve 641 is loaded into the inside of the outer distal capsule 638 in an accordion fashion.

Figure 39:
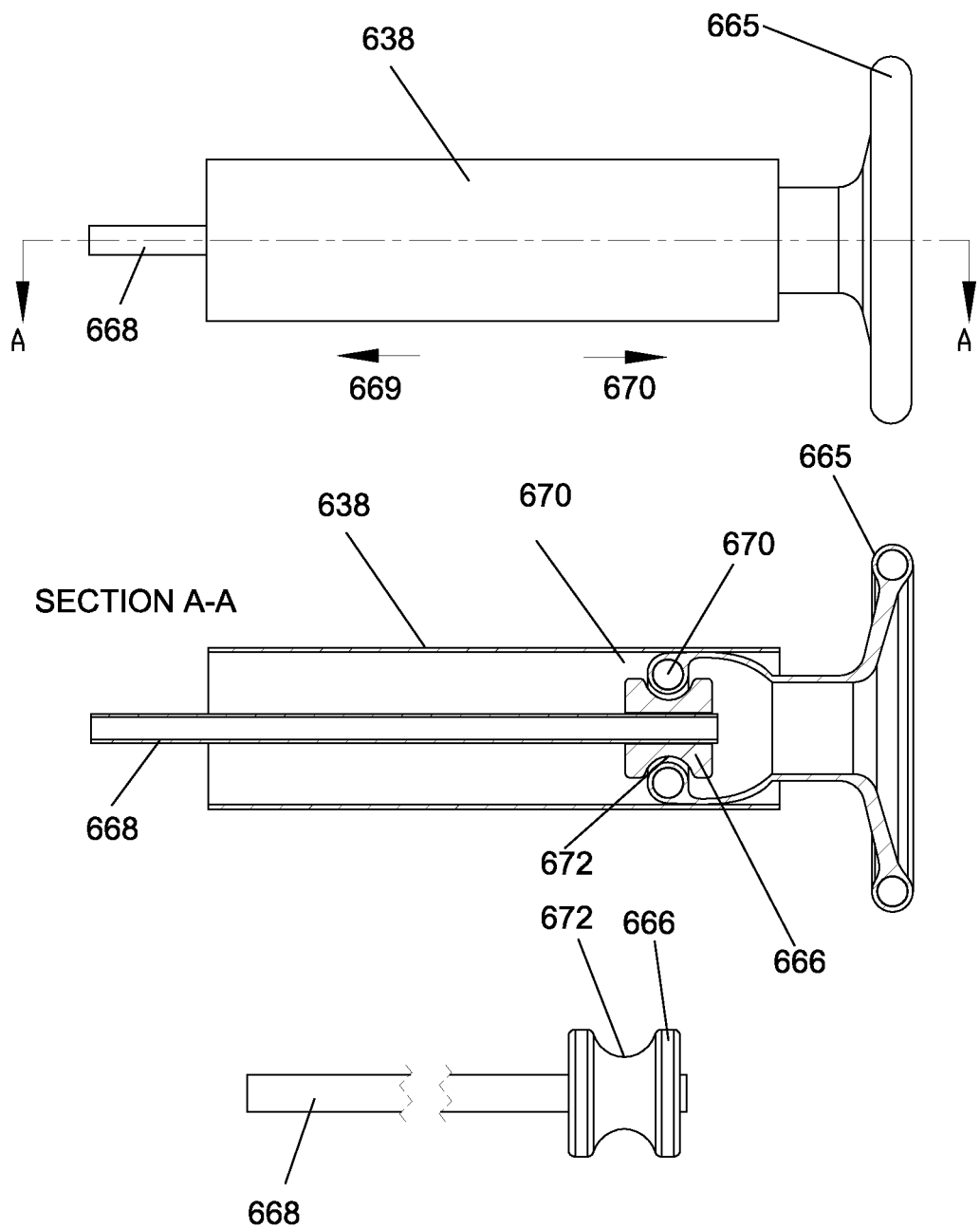
FIG. 39 is a drawing of a delivery catheter for placing the expandable anchor and intestinal bypass sleeve within the digestive tract.

FIG. 39 is a drawing of an alternative embodiment of an anchor retention device 666, distal outer capsule 638 and pusher tube 668. During the deployment of expandable anchors on catheters without retention devices 666 the distal outer capsule 638 is pulled back in direction 669 or retracted gradually to expose the expandable anchor 665. The pusher tube 668 is held in a fixed position. The expandable anchor 665 self expands and opens to the expanded diameter as the distal outer capsule 638 is retracted. During the retraction of the distal outer capsule 638 the expandable anchor 665 can in some instances slide forward in a distal direction 670 without further retraction of the distal outer capsule 638. Essentially the expandable anchor 665 can self deploy without further retraction of the distal outer capsule 638, once the distal outer capsule 638 has been partially retracted. This can lead to the expandable anchor 665 to be inadvertently deployed at the wrong implant location. In order to overcome this it is desirable to have the expandable anchor 665 remain attached to the pusher tube 668 until the distal outer capsule 638 is fully retracted. It is also desirable to have the expandable anchor 665 remain attached to the pusher tube 668 to allow the distal outer capsule 638 to be re-advanced distally 670 to cause the expandable anchor 665 to be re-collapsed and then re-sheathed so that the position of the expandable anchor in the human body can be adjusted after the start of the deployment or alternatively the expandable anchor can be removed from the body. Herein disclosed is a retention device 666 that provides for secure attachment of the expandable anchor 665 to the pusher tube 668 during distal outer capsule 638 retraction and allows for the distal outer capsule to be advanced distally 670 to sheath a partially expanded anchor 665. The retention device 666 is formed in a cylindrical form with an hour glass shape an annular groove 672 at the central portion. The diameter of retention device 666 and the annular groove 672 is sized such that the proximal end of the expandable anchor 667 can be collapsed and the diameter reduce to allow loading inside the distal outer capsule 638. The proximal end of the expandable anchor 667 has a larger cross section than the gap 671 between the outside diameter of 666 and the inside diameter of 638, therefore the expandable anchor proximal end 667 cannot move proximally or distally until the distal outer capsule 638 fully retracts past the annular groove 672.

Figure 40:
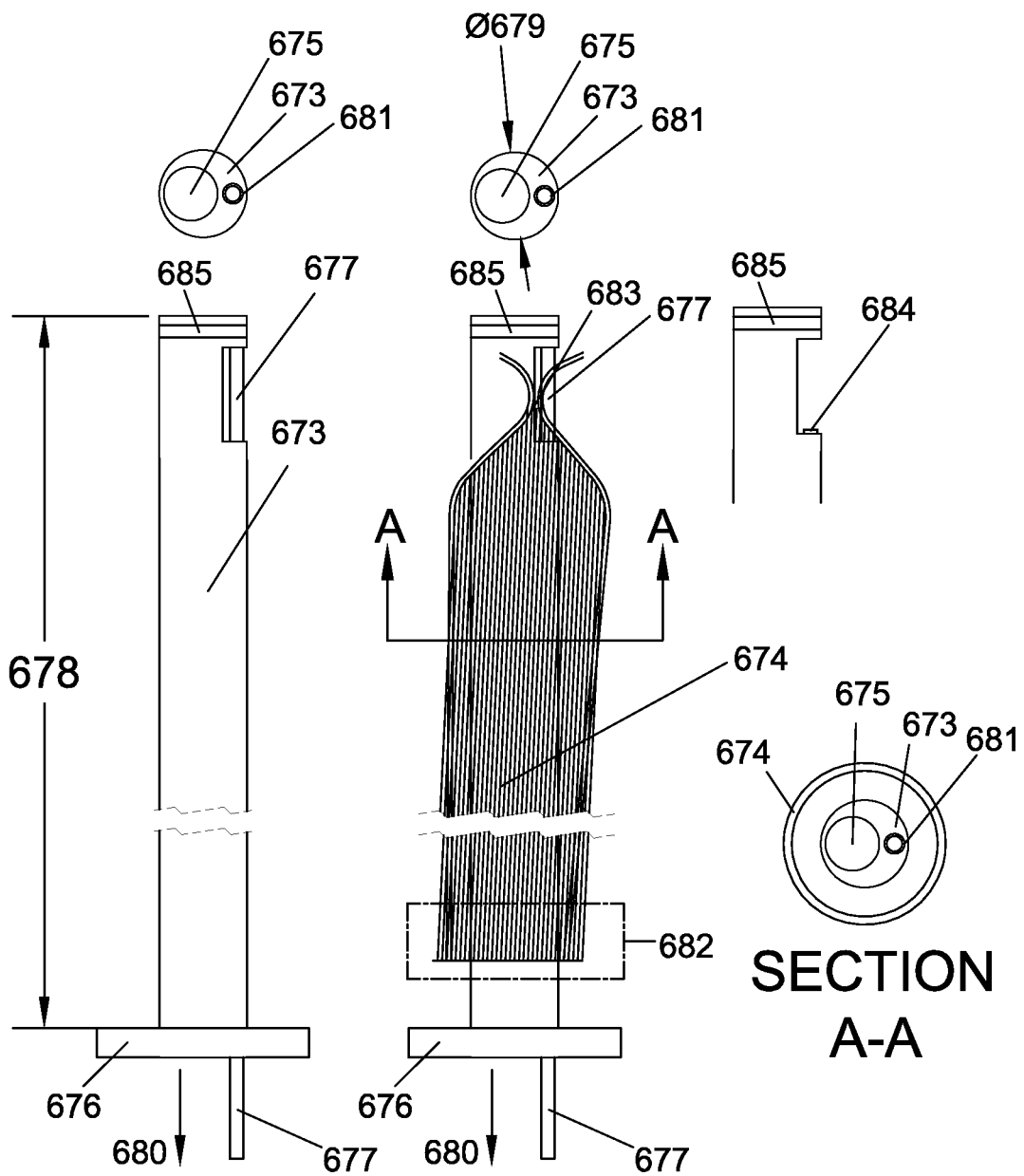
FIG. 40 is a drawing of an over the wire sleeve delivery catheter for placing an intestinal bypass sleeve within the intestine.

FIG. 40 is a drawing of an over the wire sleeve delivery catheter for placing an intestinal bypass sleeve within the intestine. The sleeve delivery catheter is made from a piece of two lumen tubing 673. The two lumen tubing 673 has a circular cross section. The outside diameter 679 can range from about 1 mm to 10 mm in diameter, but the diameter is about 2.3 mm in the preferred embodiment. The guide wire lumen 675 in the two lumen tubing 673 is sized to accommodate a guide wire (guide wire not shown) and can range in diameter from 0.5 mm to 2 mm. The release wire lumen 681 is sized to accommodate a release wire 677. The release wire 677 can slide freely within the release wire lumen 681. The length 678 of the sleeve delivery catheter can range from one to three meters in length depending upon the length of the intestinal bypass sleeve 674 length that is to be delivered with the sleeve delivery catheter. An intestinal bypass sleeve 674 is loaded over the outside diameter of the sleeve delivery catheter. The intestinal bypass sleeve 674 is secured to the sleeve delivery catheter at 683. The release wire 677 is inserted through a hole in the side of the intestinal bypass sleeve 674. To deploy the sleeve the release wire is pulled in direction 680 until the wire is retracted into the open position 684. An expandable anchor would be attached to the intestinal bypass sleeve at location 682 but it is not shown. The sleeve delivery catheter can have a handle attached to the proximal end 676. The two lumen tubing 673 is extruded from Pebax® (polyether block amide), PEEK, Hytrel (polyester elastomer), nylon 12, nylon 11, nylon 6, nylon 6,6, polyethylene, polyurethane or other suitable polymer. The lumens 675 and 681 can have a liner in the lumen made from PTFE. The release wire 677 can be made from plastic such as PEEK or a metal such as stainless steel, MP35N, Nitinol or other suitable metal. The release wire 677 may be PTFE coated or siliconed coat to reduce sliding friction within the lumen 681.

Figure 41:
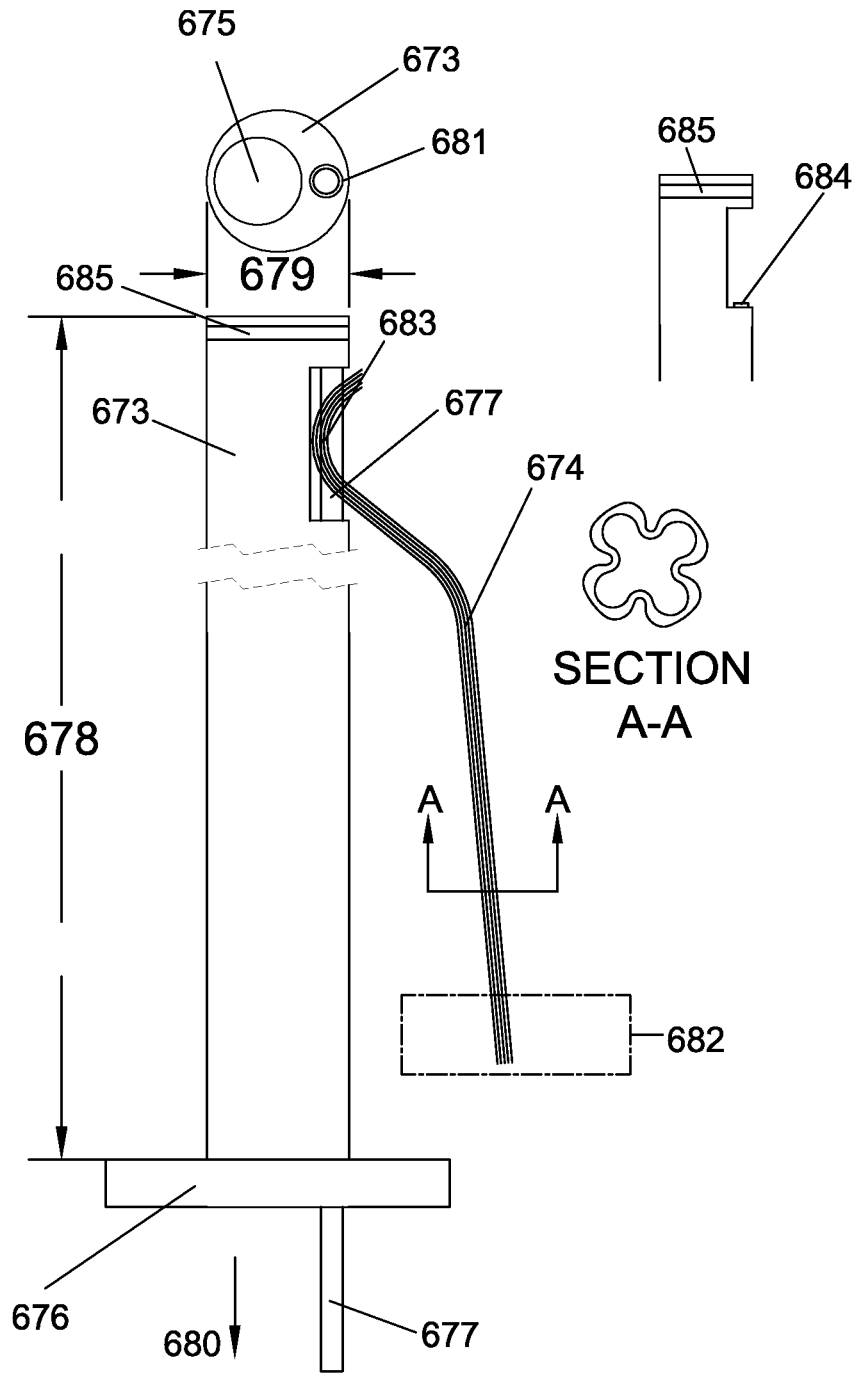
FIG. 41 is a drawing of a monorail sleeve delivery catheter for placing an intestinal bypass sleeve within the intestine.

FIG. 41 is a drawing of a monorail sleeve delivery catheter for placing an intestinal bypass sleeve within the intestine. The sleeve delivery catheter is made from a piece of two lumen tubing 673. The two lumen tubing 673 has a circular cross section. The outside diameter 679 can range from about 1 mm to 10 mm in diameter, but the diameter is about 2.3 mm in the preferred embodiment. The guide wire lumen 675 in the two lumen tubing 673 is sized to accommodate a guide wire (guide wire not shown) and can range in diameter from 0.5 mm to 2 mm. The release wire lumen 681 is sized to accommodate a release wire 677. The release wire 677 can slide freely within the release wire lumen 681. The length 678 of the sleeve delivery catheter can range from one to three meters, depending upon the length of the intestinal bypass sleeve 674, which is the length that is to be delivered with the sleeve delivery catheter. An intestinal bypass sleeve 674 is loaded parallel to outside diameter of the sleeve delivery catheter. The intestinal bypass sleeve 674 is secured to the sleeve delivery catheter at 683. The release wire 677 is inserted through a hole in the side of the Intestinal bypass sleeve 674. To deploy the sleeve the release wire is pulled in direction 680 until the wire is retracted into the open position 684. An expandable anchor would be attached to the intestinal bypass sleeve at location 682 but it is not shown. The sleeve delivery catheter can have a handle attached to the proximal end 676. The two lumen tubing 673 can be extruded from Pebax® (polyether block amide), PEEK, Hytrel (polyester elastomer), nylon 12, nylon 11, nylon 6, nylon 6,6, polyethylene, polyurethane or other suitable polymer. The lumens 675 and 681 can have a liner in the lumen made from PTFE. The release wire 677 can be made from plastic such as PEEK or a metal such as stainless steel, MP35N, Nitinol or other suitable metal. The release wire 677 may be PTFE coated or silicone coated to reduce sliding friction within the lumen 681.

Figure 42:
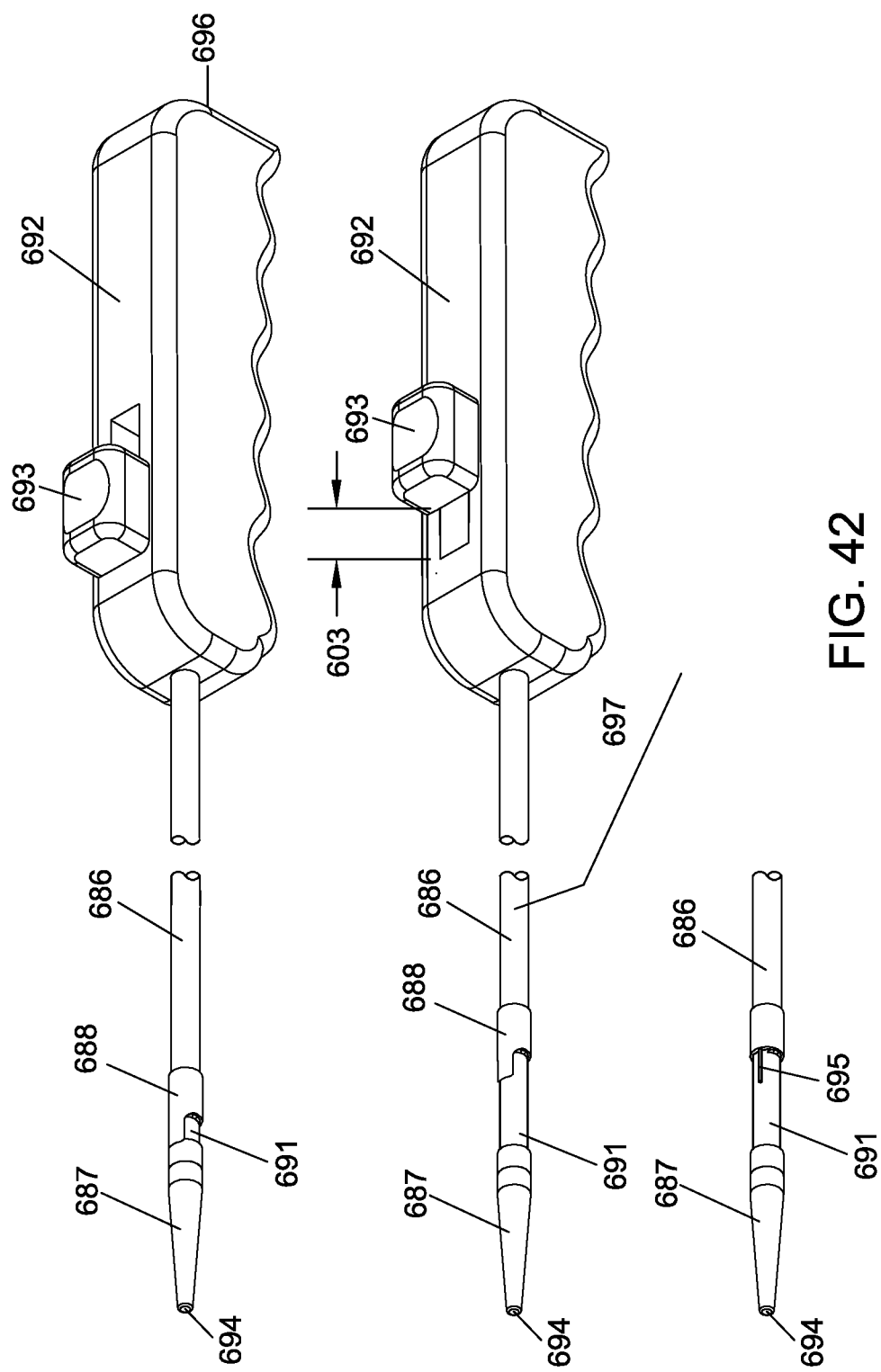
FIG. 42 is a drawing of an over the wire sleeve delivery catheter for placing an intestinal bypass sleeve within the intestine.

FIG. 42 is a drawing of an alternative embodiment of an over the wire sleeve delivery catheter for placing an intestinal bypass sleeve within the intestine. The sleeve delivery catheter is comprised of a proximal handle 692, an outer tube 686, an inner tube 691, a distal tip 687, an actuation knob 693 and a holder collar 688. The sleeve delivery catheter has two coaxial tubes. The outer tube 686 connects to the actuation knob 693. The inner tube 691 is connected to the proximal handle 692. The holder collar 688 is connected to the distal end of the outer tube. The distal tip 687 is connected to the distal end of the inner tube 691. The outer tube 686 and inner tube 691 can be made from Pebax® (polyether block amide), PEEK, Hytrel (polyester elastomer), nylon 12, nylon 11, nylon 6, nylon 6,6, polyethylene, polyurethane or other suitable polymer. The inside lumen of outer tube 686 or the outside diameter of inner tube 691 can have a liner or covering of PTFE. The distal tip 687 can be made from a plastic such as Pebax® (polyether block amide), Hytrel (polyester elastomer), nylon 12, nylon 11, nylon 6, nylon 6,6, polyethylene, polyurethane or other suitable polymer. The sleeve delivery catheter has a guide wire lumen 694 to allow the sleeve delivery catheter to be tracked over a guide wire. The guide wire can exit at 696 for a full over the wire catheter. Alternatively the guide wire can exit the catheter at 697 for a monorail type catheter. The distance 689 between the distal tip 687 and holder collar 688 can be increased or decreased by sliding the actuation knob 692 towards or away from the distal tip 687 to change the distance 690. The intestinal bypass sleeve is not shown in FIG. 42, but it is attached to the sleeve delivery catheter as previously disclosed in FIG. 40 in an over-the-wire means. Alternatively the intestinal bypass sleeve is attached to the sleeve delivery catheter as previously disclosed in FIG. 41 in a monorail or parallel to the catheter means with the sleeve delivery catheter not residing within the lumen of the intestinal bypass graft. An alternative embodiment of a holder collar is disclosed in 695.

Holder collars 688 and 695 are actuated and released by actuation knob 692 to mechanically secure the intestinal bypass sleeve during delivery and release the intestinal bypass sleeve from the sleeve delivery catheter at the intended implant location.

Figure 43:
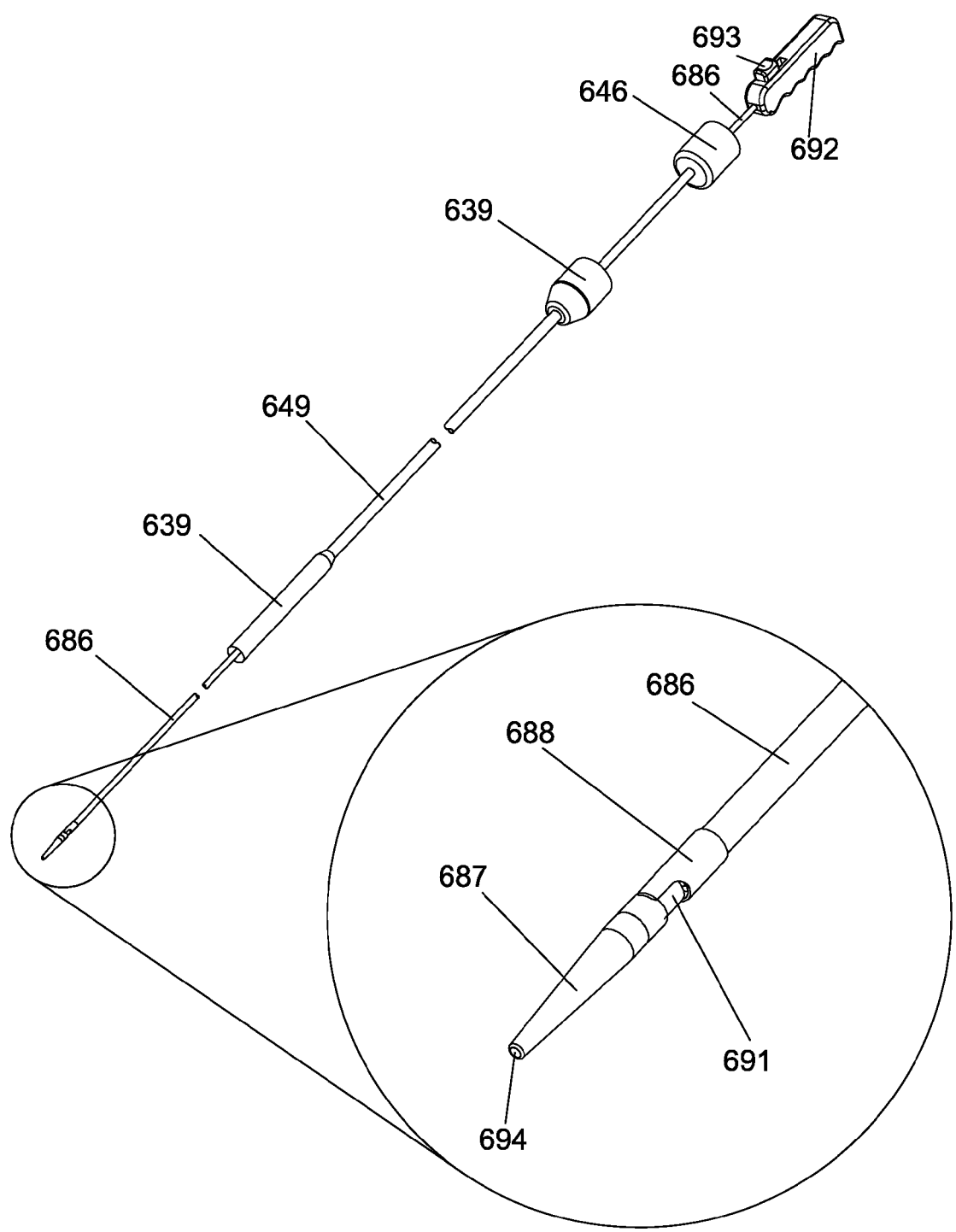
FIG. 43 is a drawing of a delivery catheter for placing the expandable anchor and intestinal bypass sleeve within the digestive tract.

FIG. 43 is a drawing of a delivery catheter for placing the expandable anchor and intestinal bypass sleeve within the digestive tract. A sleeve delivery catheter as previously disclosed in FIG. 42 is inserted through the central lumen of a delivery catheter as previously disclosed in FIG. 32.

Figure 44A:
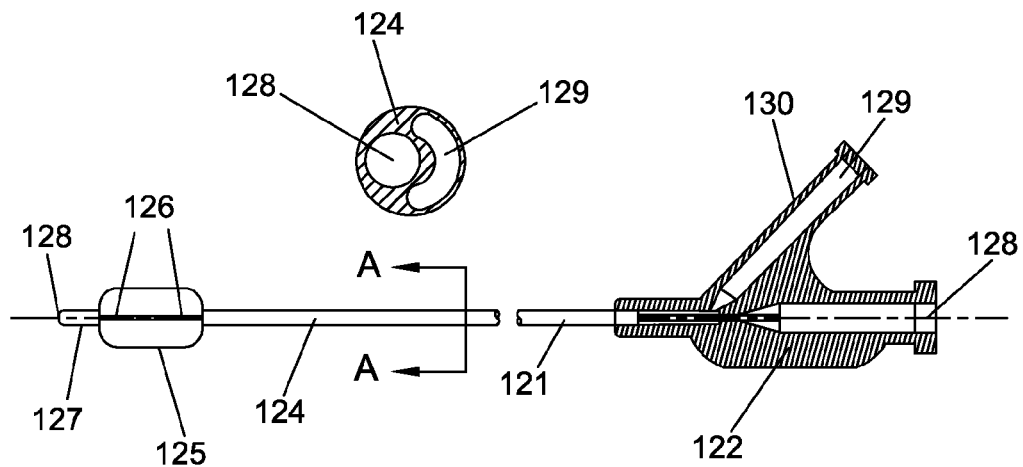
FIG. 44A is a drawing of an over the wire balloon catheter that is used as a sleeve delivery catheter for placing an intestinal bypass sleeve within the intestine.

FIG. 44A is a drawing of a balloon catheter 121 that is used as a sleeve delivery catheter. The balloon is composed of the following elements: proximal hub 122, catheter shaft 124, distal balloon component 125, radiopaque marker bands 126, distal tip 127, guide wire lumen 128, inflation lumen 129. Distal balloon component 125 can be made from silicone, silicone polyurethane copolymers, latex, nylon 12, PET (Polyethylene terephthalate) Pebax® (polyether block amide), polyurethane, polyethylene, polyester elastomer or other suitable polymer. The distal balloon component 125 can be molded into a cylindrical shape, into a dogbone or a conical shape. The distal balloon component 125 can be made compliant or non-compliant. The distal balloon component 125 can be bonded to the catheter shaft 124 with glue, heat bonding, solvent bonding, laser welding or suitable means. The catheter shaft can be made from silicone, silicone polyurethane copolymers, latex, nylon 12, PET (Polyethylene terephthalate) Pebax® (polyether block amide), polyurethane, polyethylene, polyester elastomer or other suitable polymer. Section A-A in FIG. 3A is a cross-section of the catheter shaft 124. The catheter shaft 124 if shown as a dual lumen extrusion with a guide wire lumen 128 and an inflation lumen 129. The catheter shaft 124 can also be formed from two coaxial single lumen round tubes in place of the dual lumen tubing. The balloon is inflated by attaching a syringe (not shown) to a luer fitting side port 130. The sizing balloon accommodates a guide wire through the guide wire lumen from the distal tip 127 through the proximal hub 122. The balloon 121 has two or more radiopaque marker bands 126 located on the catheter shaft to allow visualization of the catheter shaft and balloon position. The marker bands can be made from tantalum, gold, platinum, platinum iridium alloys or other suitable material.

Figure 44B:
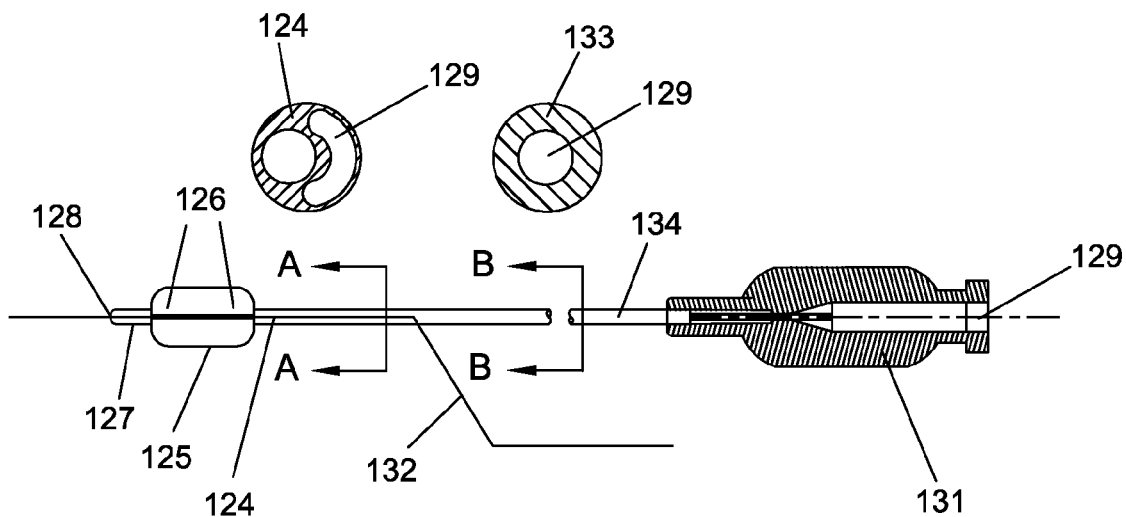
FIG. 44B is a drawing of a monorail balloon catheter that is used as a sleeve delivery catheter for placing an intestinal bypass sleeve within the intestine.

FIG. 44B shows a rapid exchange balloon catheter 134 that is used as a sleeve delivery catheter. The balloon is composed of the following elements: proximal luer 131, catheter shaft 124, distal balloon component 125, radiopaque marker bands 126, distal tip 127, guide wire lumen 128, inflation lumen 129. The materials of construction will be similar to that of FIG. 4A. The guide wire lumen 128 does not travel the full length of the catheter. It starts at the distal tip 127 and exits out the side of the catheter at distance shorter than the overall catheter length. The guide wire 132 is inserted into the balloon catheter to illustrate the guide wire path through the sizing balloon. The balloon catheter shaft changes section along its length from a single lumen at section B-B 133 to a dual lumen at section A-A at 124.

Figure 45A:
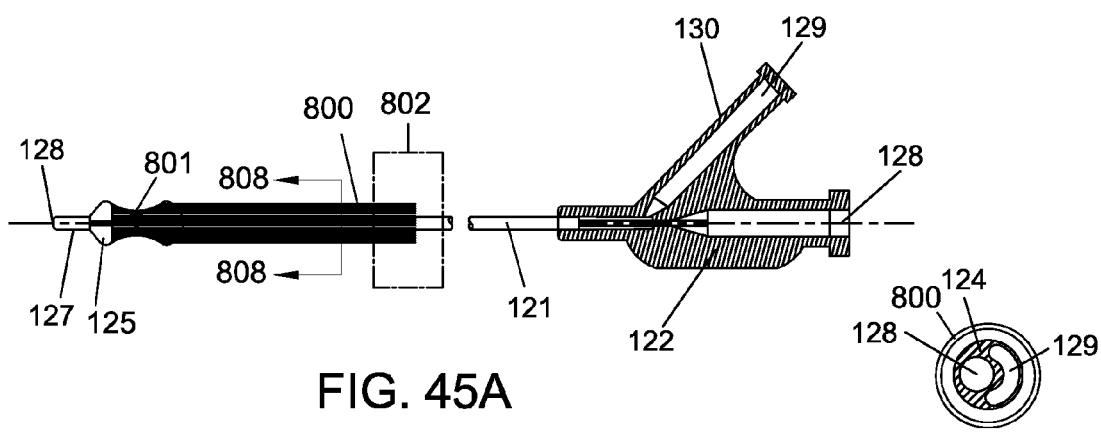
FIG. 45A is a drawing of the sleeve delivery catheter of FIG. 44A in which the intestinal bypass sleeve has been attached to the balloon catheter.

FIG. 45A is a drawing of the sleeve delivery catheter balloon previously disclosed in FIG. 44A with an intestinal bypass sleeve 800 attached to the balloon. The intestinal bypass sleeve 800 is attached to the balloon at location 801 by a release-able means. The release-able means in the preferred embodiment may be comprised of a loop of suture wrapped around the outside of the intestinal bypass sleeve at location 801. The suture is knotted and tied to secure the intestinal bypass sleeve at location 801. The intestinal bypass sleeve 800 may be perforated by the suture at located 801 to increase the securement force. The balloon component 125 is partially inflated to a low pressure of about one atmosphere of pressure to secure the suture and the intestinal bypass sleeve 800 at location 801. Alternatively the sleeve is fastened to the balloon by band of plastic or an elastomer, such as a piece of heat shrink tubing, a cable tie, adhesive or by hook and loop fastener. The suture may be made of polyester, nylon, polypropylene, or other suitable polymer and may be made from a mono filament or a multifilament yarn. The intestinal bypass sleeve 800 can be arranged around the balloon catheter in a coaxial configuration as shown in section 808 or alternatively it can be arranged as shown in FIG. 45C section 809. The intestinal bypass sleeve 800 is attached to the expandable anchor at location 802. The expandable anchor would be loaded into a distal outer capsule for delivery.

Figure 45B:
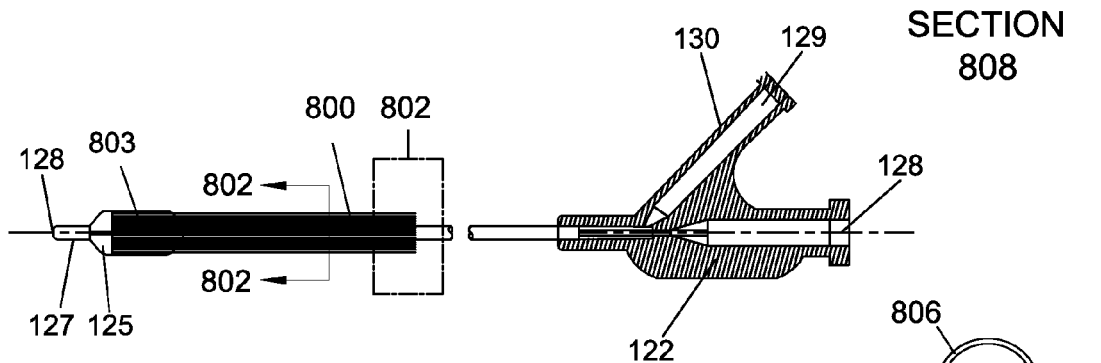
FIG. 45B is a drawing of the sleeve delivery catheter of FIG. 44A in which the intestinal bypass sleeve has been released from the balloon catheter.
Figure 45C:
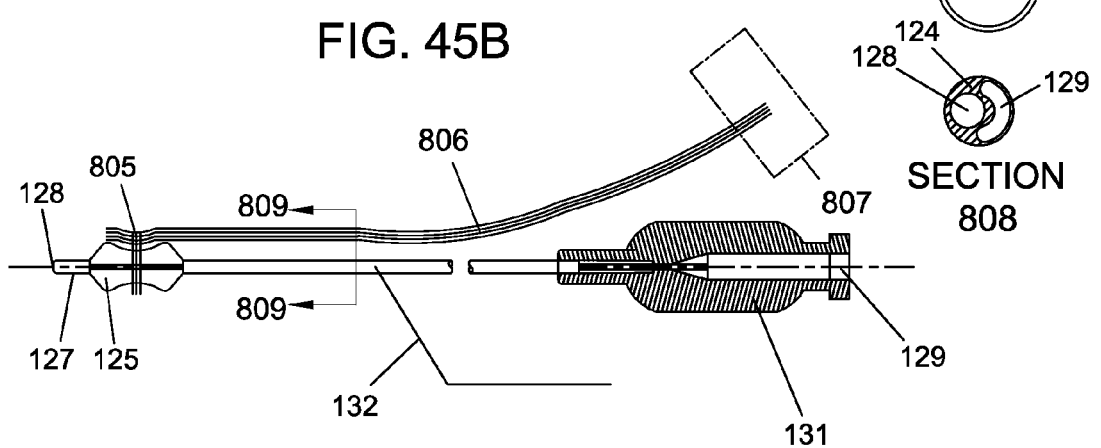
FIG. 45C is a drawing of the monorail sleeve delivery catheter of FIG. 44B in which the intestinal bypass sleeve has been attached to the balloon catheter.

FIG. 45B is a drawing of the sleeve delivery catheter and intestinal bypass sleeve 800 of FIG. 45A, the distal balloon component 125 has been inflated with air, water, saline or contrast media to a pressure high enough to expand the diameter of the balloon component 125 and to break the suture securement 803 of the intestinal bypass sleeve 800 from the distal end of the sleeve delivery balloon. The pressure required to break the suture is in the range from 2 to 15 atmospheres. After the suture or other means of securement is broken and the intestinal bypass sleeve 800 is released, the balloon is deflated and withdrawn from the intestinal bypass sleeve.

FIG. 45C is a drawing of the monorail sleeve delivery catheter of FIG. 44B in which the intestinal bypass sleeve 806 has been attached to the balloon catheter at location 805. The securement mechanism and release means are the same as previously disclosed in FIG. 45A and FIG. 45B. The intestinal bypass sleeve 806 is not coaxial over the balloon catheter, but is delivered along side or parallel to the balloon catheter as shown in section 809. The intestinal bypass sleeve 806 is attached to the expandable anchor at location 807. The expandable anchor would be loaded into a distal outer capsule for delivery.

Figure 46:
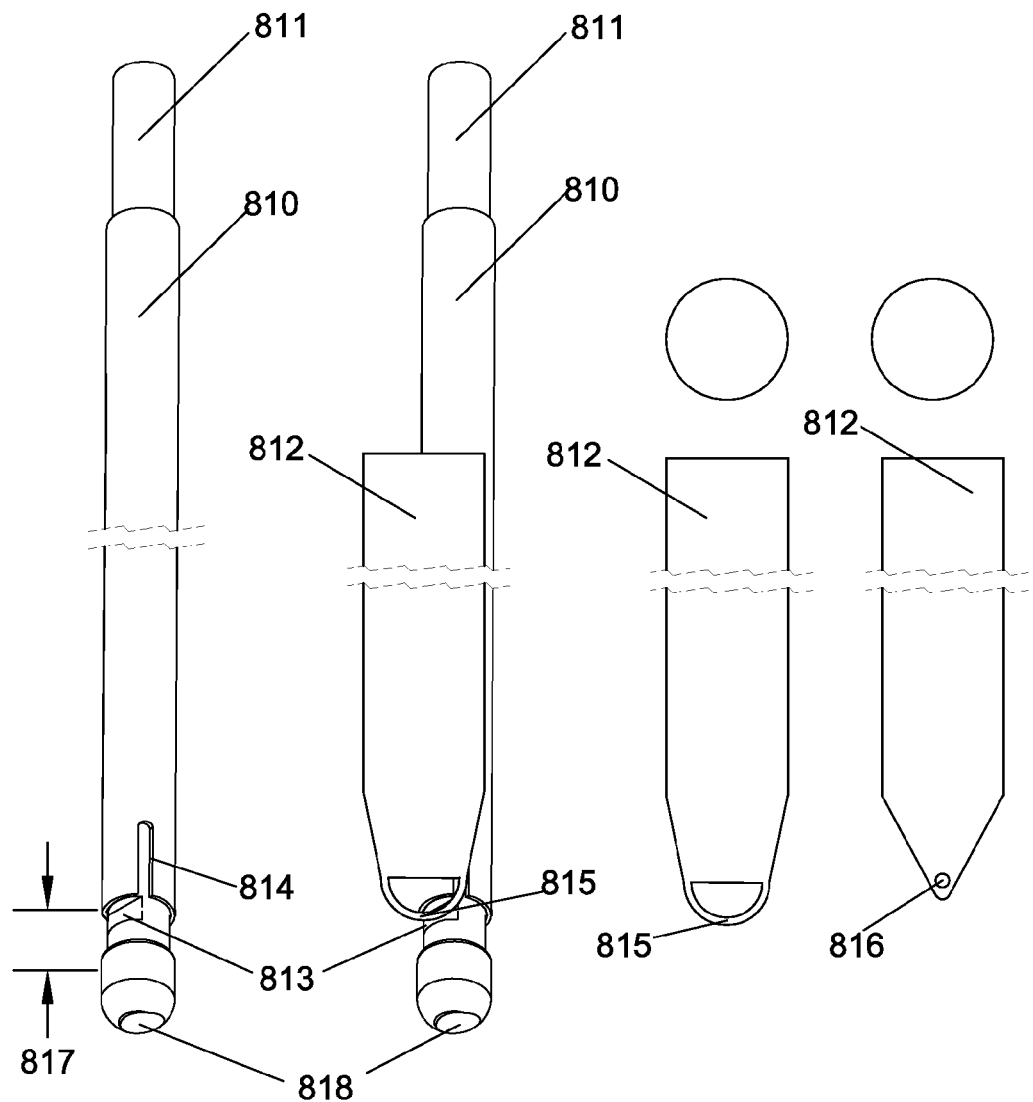
FIG. 46 is a drawing of a sleeve delivery catheter.

FIG. 46 is a drawing of a sleeve delivery catheter. Sleeve delivery catheter is comprised of an outer actuation tube 810 an inner non-actuating tube 811. The outer actuating tube 810 can have a slot 814 cut at the distal end to secure the tab 815 at the distal end of an intestinal bypass sleeve 812. The inner non-actuating tube 811 can have a recess 813 cut into the diameter to serve as a receptacle to hold the tab 815. The intestinal bypass sleeve 812 is secured to the distal end of the sleeve delivery catheter by inserting the tab 815 into slot 814 and sliding the outer actuating tube 810 distally to close gap 817. To release the intestinal bypass sleeve 812 the outer actuating tube 810 is retracted to increase the gap 817 and the tab 815 is released from slot 814. Alternatively the intestinal bypass sleeve can have a hole 816 at the distal end and be secured to the outer actuated tube 810 by a pin which inserts through hole 816. An actuation handle is attached to the proximal ends of outer actuation tube 810 and inner non-actuating tube 810, a suitable design was previously disclosed in FIG. 42. The outer actuating tube 810 and inner non-actuating tube 811 can be made from material previously disclosed in FIG. 42.

Figure 47:
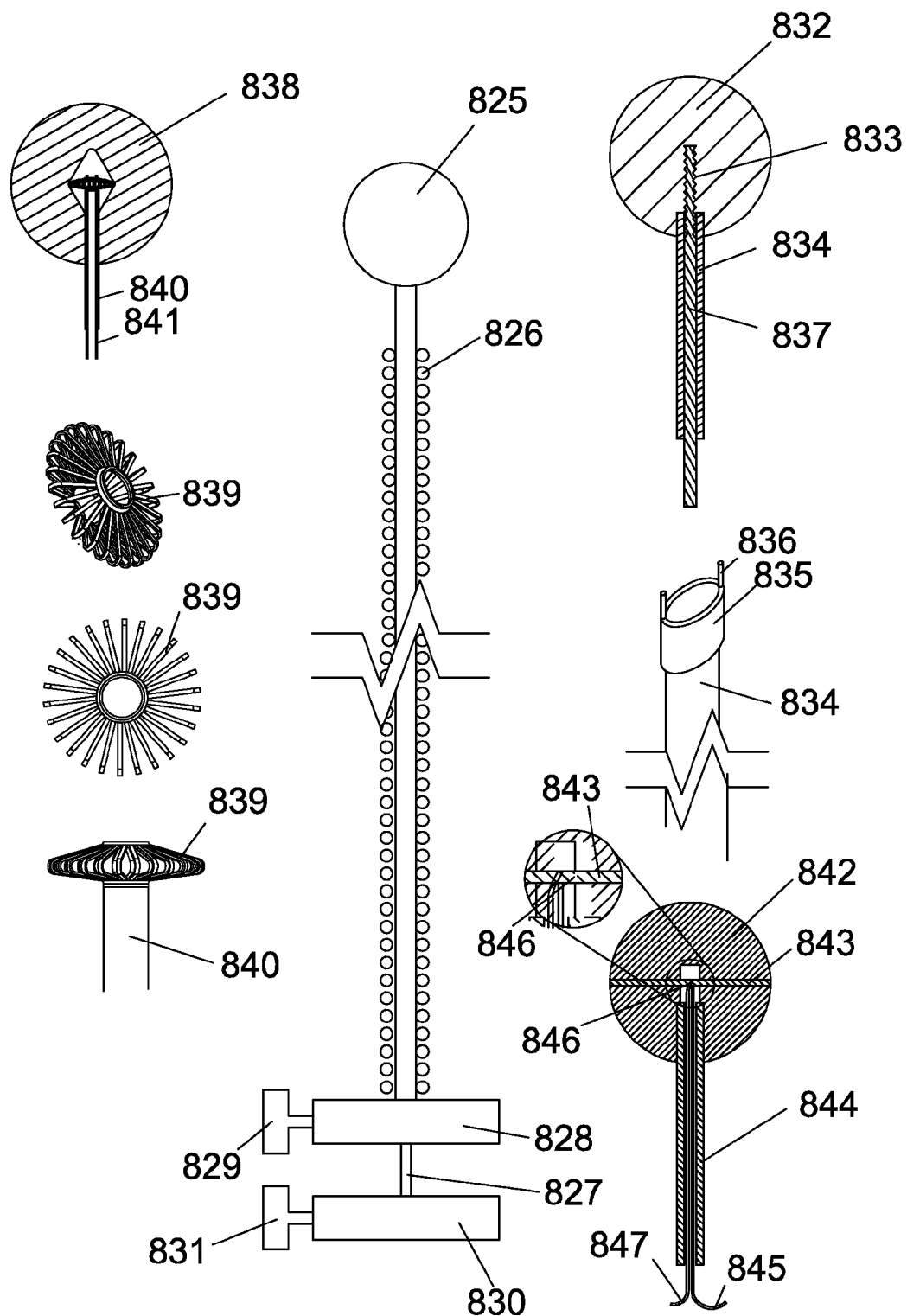
FIG. 47 is a drawing of a guide wire to be used for placing expandable anchors and intestinal bypass sleeves.

FIG. 47 shows a guide wire to be used for placing expandable anchors and intestinal bypass sleeves. During the delivery of intestinal bypass sleeves, it is necessary to insert a guide wire two feet or more into the small intestine past the pylorus into the jejunum. It can be difficult with a conventional guide wire to advance the guide wire into the jejunum in some patients. With conventional guide wires, there is a risk that the guide wire tip may perforate through the intestinal wall if the guide wire is advanced with a large force and the guide wire does not follow the natural intestinal lumen. It is desirable to have a guide wire that can easily track several feet beyond the pylorus and have low risk of perforating the small intestine wall. It is also desirable to have the guide wire have a low profile when it is removed from a patient after an expandable anchor and intestinal bypass sleeve are placed. The guide wire is comprised of a releasable ball tip 825, an outer coil or tube 826, an inner tube 827, an outer tube handle 828, an outer tube lock 829, an inner tube handle 827 and an inner tube lock 831. The ball tip can range in diameter from 3 mm to 12 mm. The ball can be made from plastics such as PTFE, Nylon, polypropylene, polyethylene, PEEK or other suitable material. Alternatively, the ball can be made of a metal such as stainless steel, tantalum, titanium or other suitable material. The outer coil or tube 826 can be made of a plastic tube, a wound wire coil, a metal tube or from helical hollow stranded tube (Fort Wayne Metals).

According to various embodiment, the outer diameter of the outer tube 826 can range from 0.5 mm in diameter up to 4 mm in diameter. The length of the outer tube 826 can range from 1 meter to 4 meters. The inner tube 827 inserts coaxially within the inner diameter of the outer tube 826. The outer tube handle 828 is secured and released from the outer tube 826 by lock knob 829. The inner tube handle 830 is secured and released from the inner tube 827 by the lock knob 831. The lock knobs 829 and 831 are threaded into the lock handles 828 and 830 and lock onto the outer tube 826 or inner tube 827 by turning the lock into the handle. The ball tip 825 is threaded onto the distal end of the inner tube 827. A sectional view of the ball 832 shows the male threads 833 on the outside diameter of the inner tube threaded into the female threads on ball 832. The outer tube 834 has a collar 835 on the distal end. The collar 835 has two pins 836 that engage in holes in the outside diameter of the ball 833. The outer tube 834 and collar 835 are pushed against the ball tip 832 and rotated in a counter clockwise direction, while the inner tube 837 is rotated in a clockwise direction to unthread and detach the ball tip from the end of the guide wire.

An alternative ball securement or release mechanism incorporates a spring disk 839. The spring disk 839 can be made from Nitinol or stainless steel. The proximal hub of the spring disk 839 is attached to the outer tube 840. The distal hub of spring disk 839 is attached to the inner tube 841. The expanded spring disk 839 fits into a cavity inside the ball tip 838. The diameter of the spring disk 839 can be reduced to allow the spring disk to be withdrawn from the cavity inside the ball 838. To reduce the diameter of the spring disk the outer tube 840 is retracted while the inner tube 841 is advanced. This causes the spring disk 839 to elongate and the diameter of the spring disk to reduce to the diameter of the outer tube 840.

An alternative ball securement release mechanism incorporates a tension wire to secure and remotely release the ball from the guide wire tip. The ball tip 842 has a longitudinal socket bored into the diameter to allow outer tube 844 to extend into the ball diameter with a loose slip fit. The ball tip has a second hole drilled transversely through the diameter and a pin 843 is press fit into the transverse hole. Retention suture 847 is looped through the inside lumen of tube 844 around pin 843 at location 846 and back through the inside lumen of tube 844 a second time and exits tube 844 at 845. A handle maintains the tension on the sutures 847 and 845 until the ball is detached from the guide wire. To release the ball the end of suture 847 is withdrawn from tube 844 and the other end suture 845 is drawn into outer tube 844. The tension suture is withdrawn over pin 843 at point 846 and the ball is released. The tension suture may be comprised of a plastic suture and made from PTFE, polyester, Dyneema, nylon, polypropylene or other suitable polymer. Alternatively the retention suture 847 is comprised of metal wire, cable or braided wire and is made from stainless steel, Nitinol, MP35n, L605, Elgiloy, titanium or other suitable metal.

Figure 48A:
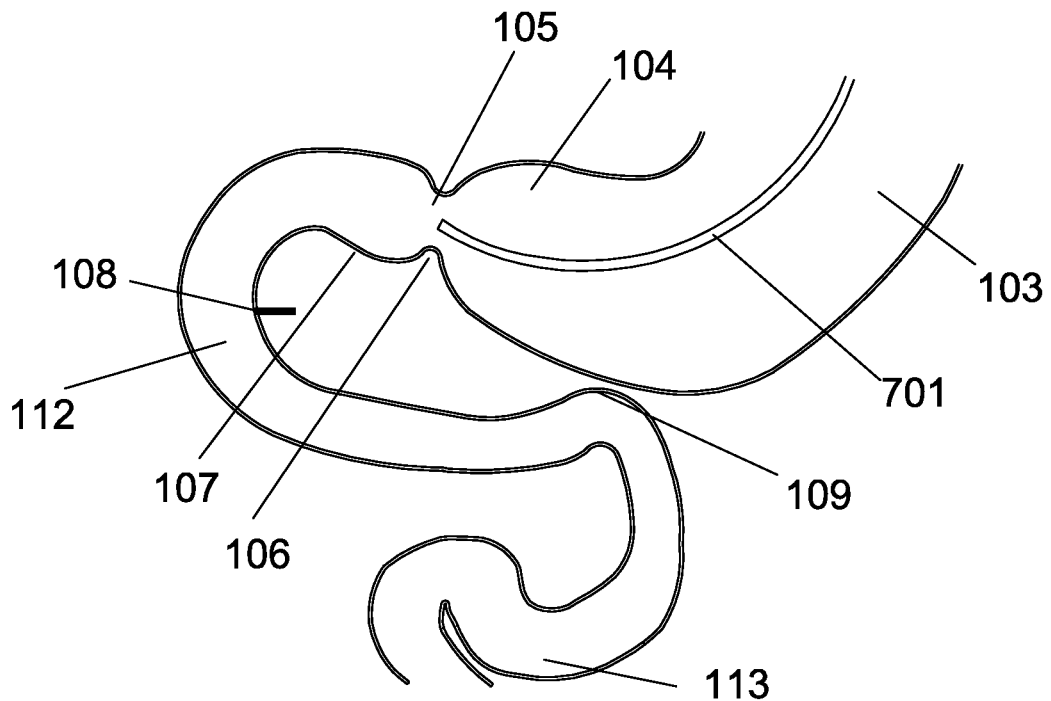
FIG. 48A is a cross-sectional view of a portion of the digestive tract in a human body with an endoscope inserted through the mouth, esophagus and stomach to the pylorus.

FIG. 48A is a cross-sectional view of a portion of the digestive tract in a human body with an endoscope 701 inserted through the mouth, esophagus and stomach to the pylorus 106.

Figure 48B:
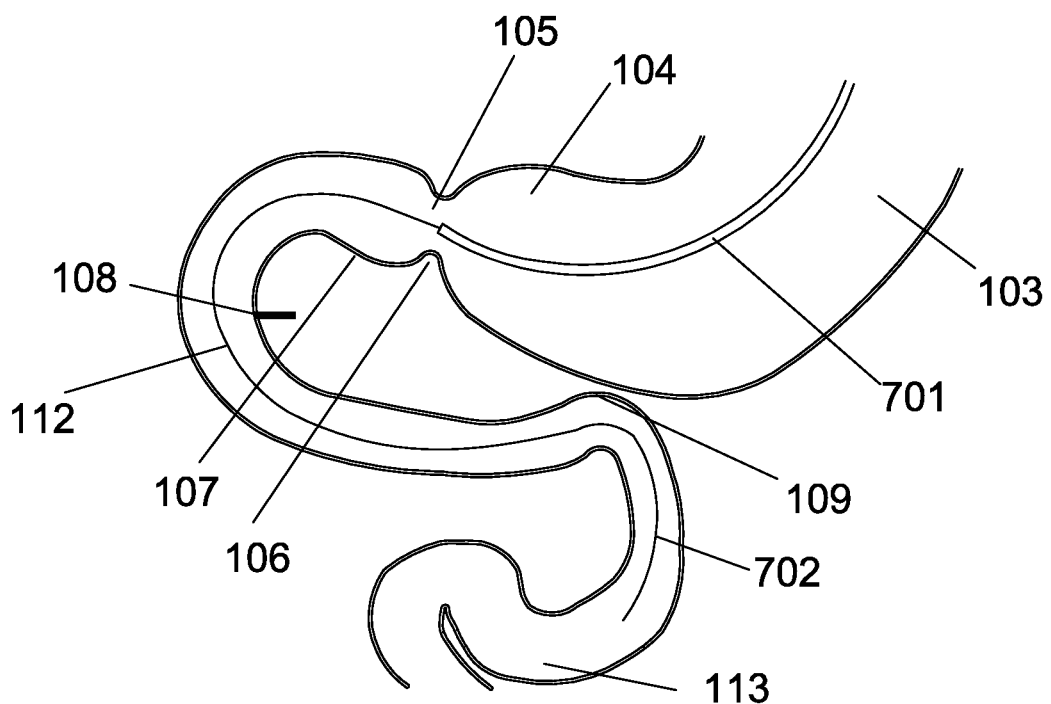
FIG. 48B is a cross-sectional view of a portion of the digestive tract in a human body with an endoscope inserted through the mouth, esophagus and stomach to the pylorus. A guide wire is inserted through the working channel of the endoscope. The guide wire is advanced distally in the small intestine lumen into the jejunum.

FIG. 48B is a cross-sectional view of a portion of the digestive tract in a human body with an endoscope 701 inserted through the mouth, esophagus and stomach 103 to the pylorus. A guide wire 702 is inserted through the working channel of the endoscope 701. The guide wire is advanced distally in the small intestine lumen into the jejunum 113.

Figure 49A:
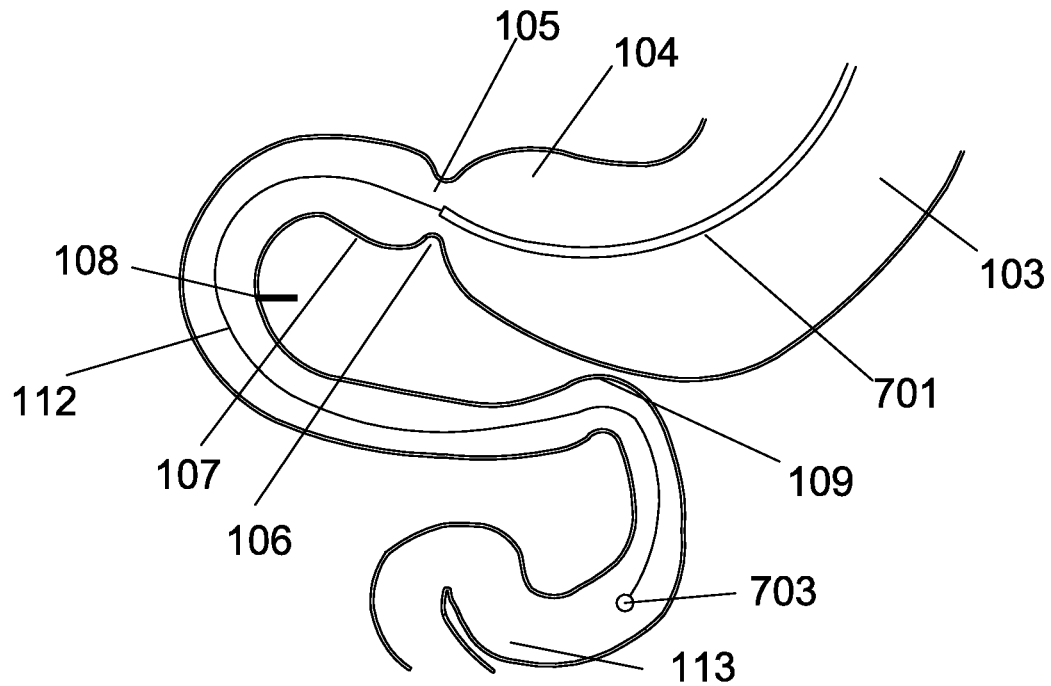
FIG. 49A is a cross-sectional view of a portion of the digestive tract in a human body with an endoscope inserted through the mouth, esophagus and stomach to the pylorus. The guide wire of FIG. 47 is back loaded into the working channel of the endoscope. The guide wire of FIG. 47 is advanced distally in the small intestine lumen into the jejunum.

FIG. 49A is a cross-sectional view of a portion of the digestive tract in a human body with an endoscope inserted through the mouth, esophagus and stomach to the pylorus. The guide wire 702 as previously disclosed in FIG. 47 with a ball 703 attached to the distal end is back-loaded into the working channel of the endoscope 701 prior to insertion of the endoscope. The guide wire 702 is advanced distally in the small intestine lumen into the jejunum.

Figure 49B:
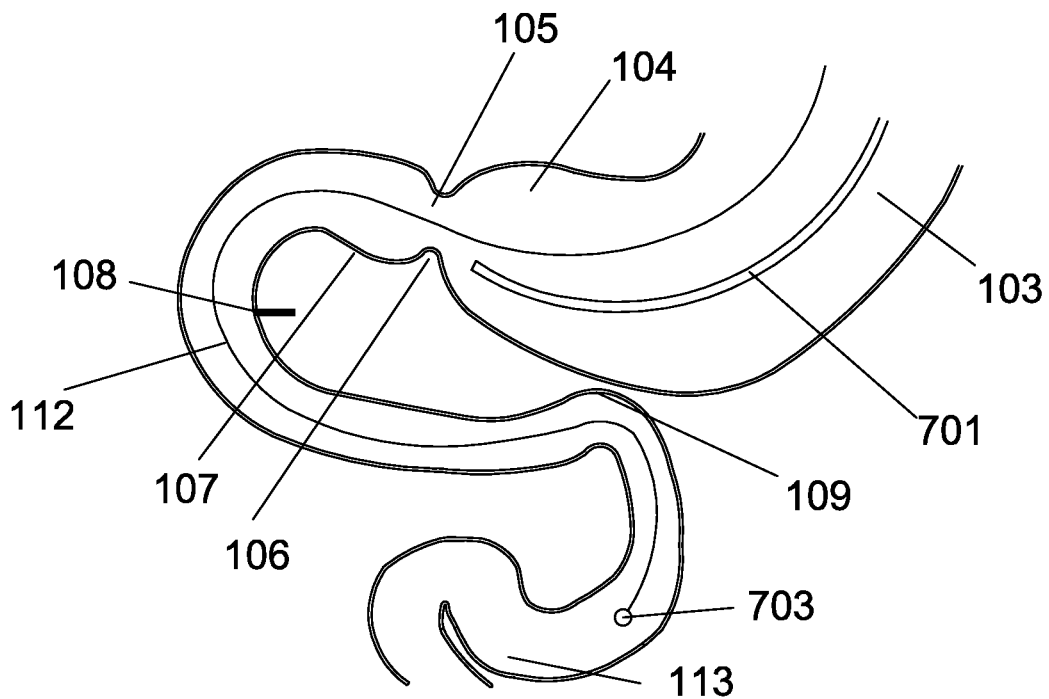
FIG. 49B is a cross-sectional view of a portion of the digestive tract in a human body with an endoscope inserted through the mouth, esophagus and stomach to the pylorus. The guide wire of FIG. 47 is left in place in the jejunum while the endoscope is withdrawn from the body. The endoscope is then reinserted into the stomach through the mouth and esophagus parallel to the guide wire, but the guide wire is not in the working channel of the endoscope.

FIG. 49B is a cross-sectional view of a portion of the digestive tract in a human body with an endoscope inserted through the mouth, esophagus and stomach to the pylorus. The guide wire of FIG. 47 is left in place in the jejunum while the endoscope is withdrawn from the body. The endoscope 701 is then reinserted into the stomach through the mouth and esophagus parallel to the guide wire 703, but the guide wire 703 is not in the working channel of the endoscope.

Figure 50A:
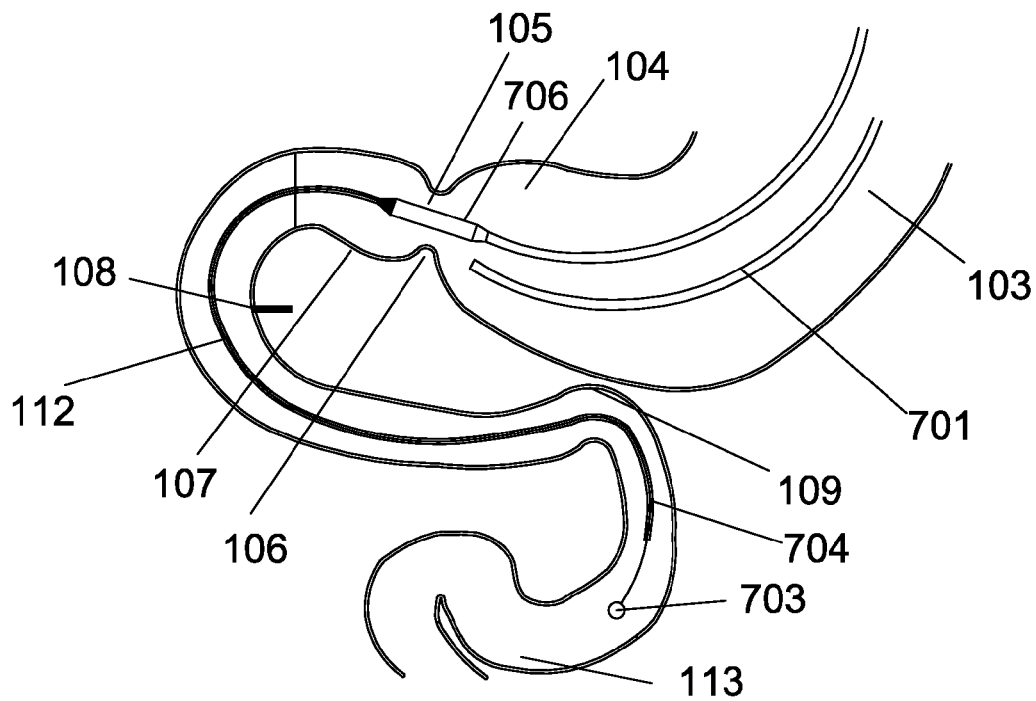
FIG. 50A is a continuation in the deployment sequence from FIG. 49B. An expandable anchor and intestinal bypass sleeve has been loaded on to delivery catheter. The delivery catheter is advanced over the guide wire through the mouth, esophagus, Stomach and small intestine until the distal end of the sleeve reaches the desired implant location.

FIG. 50A is a continuation in the deployment sequence from FIG. 49B. An expandable anchor and intestinal bypass sleeve 704 have been loaded on to the delivery catheter. The delivery catheter and intestinal bypass sleeve 704 are advanced over the guide wire 702 through the mouth, esophagus, stomach and small intestine until the distal end of the intestinal bypass sleeve 704 reaches the desired implant location. The release wire FIG. 40 item 677 on the sleeve delivery catheter is then retracted FIG. 40 680 to release the intestinal bypass sleeve 704 from the distal end of the sleeve delivery catheter.

Figure 50B:
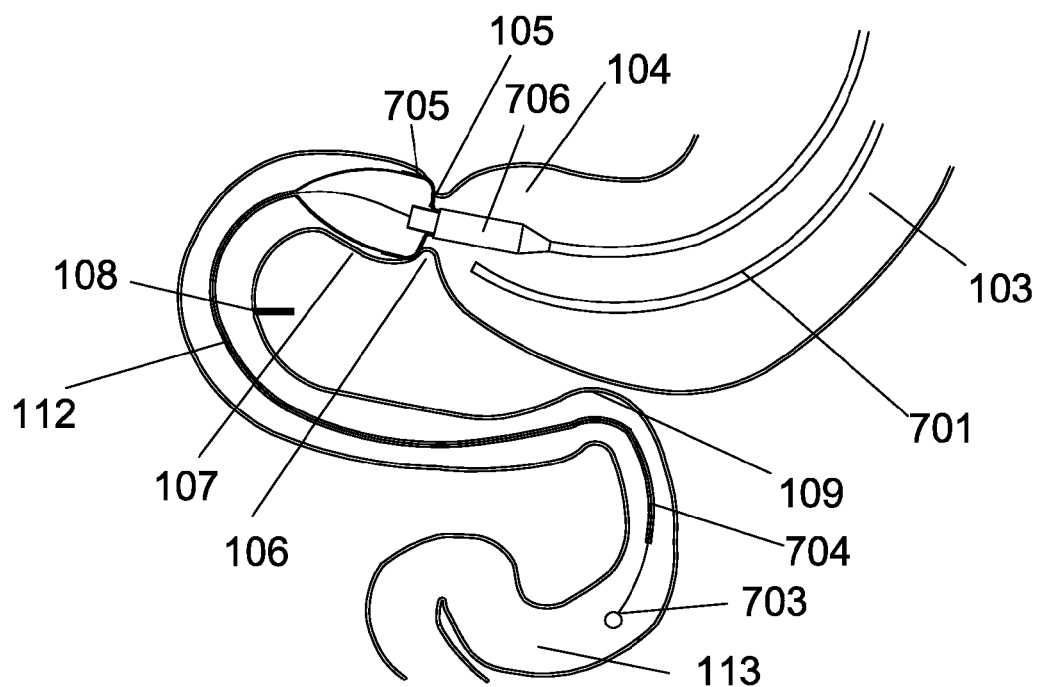
FIG. 50B is a continuation in the deployment sequence from FIG. 50A. The sleeve delivery catheter is actuated to release the distal end of the bypass sleeve from the catheter. The sleeve delivery catheter is then retracted to remove it partially or fully from the digestive system. The distal capsule of the delivery system then is partially retracted to deploy or release the distal end of the expandable anchor from the distal capsule.

FIG. 50B is a continuation in the deployment sequence from FIG. 50A. The sleeve delivery catheter distal outer capsule 706 is partially retracted proximally to deploy or release the distal end of the expandable anchor 705 from the distal outer capsule 706. The sleeve delivery catheter is then retracted to remove it partially or fully from the digestive system.

Figure 51:
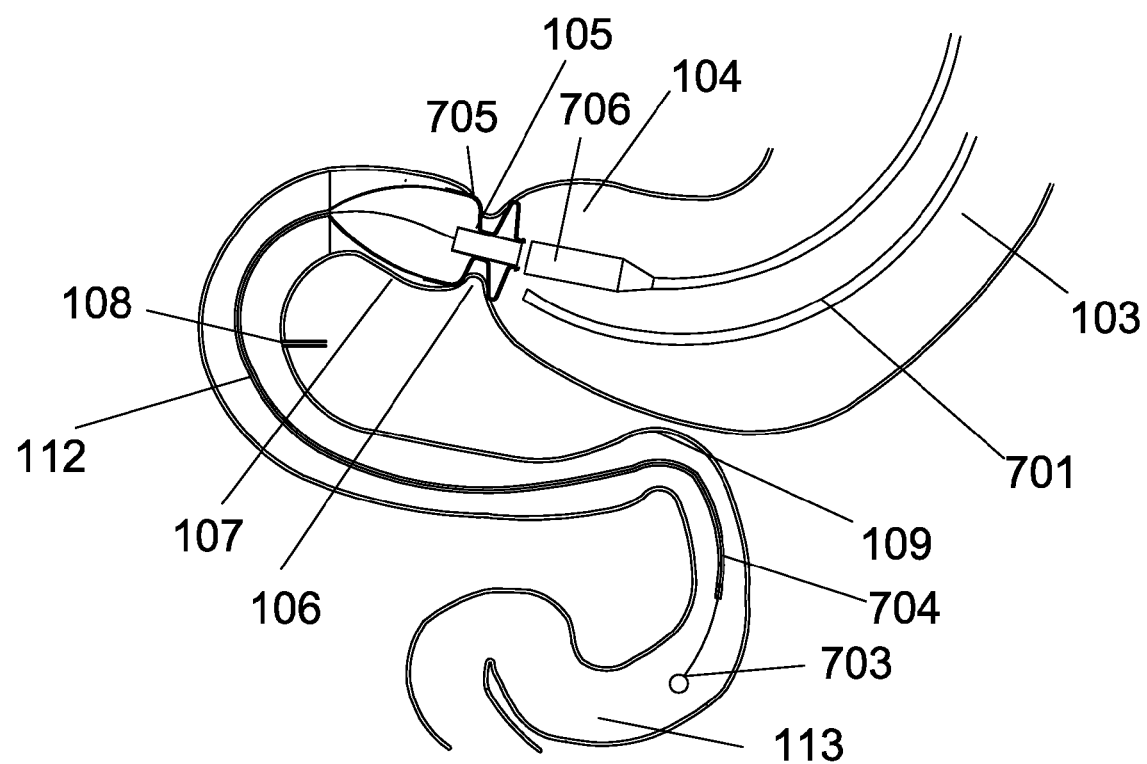
FIG. 51 is a continuation in the deployment sequence from FIG. 50B. The distal capsule of the delivery system is fully retracted to deploy or release the proximal end of the expandable anchor from the distal capsule. The expandable anchor and intestinal bypass sleeve are now in place at the intended implant location. The ball on the end of the guide wire is released. The guide wire, delivery catheter and endoscope are withdrawn from the human body.

FIG. 51 is a continuation in the deployment sequence from FIG. 50B. The distal outer capsule 706 of the delivery system is fully retracted to deploy or release the proximal end of the expandable anchor 705 from the distal capsule. The expandable anchor 705 and the intestinal bypass sleeve 704 are now in place at the intended implant location. The ball 703 on the end of the guide wire 702 is now released and left to pass naturally through the digestive tract. The ball on the end of the guide wire can alternatively be made from a bio-absorbable polymer and dissolves upon release from the guide wire. The guide wire, delivery catheter, and endoscope are withdrawn from the human body.

Figure 52:
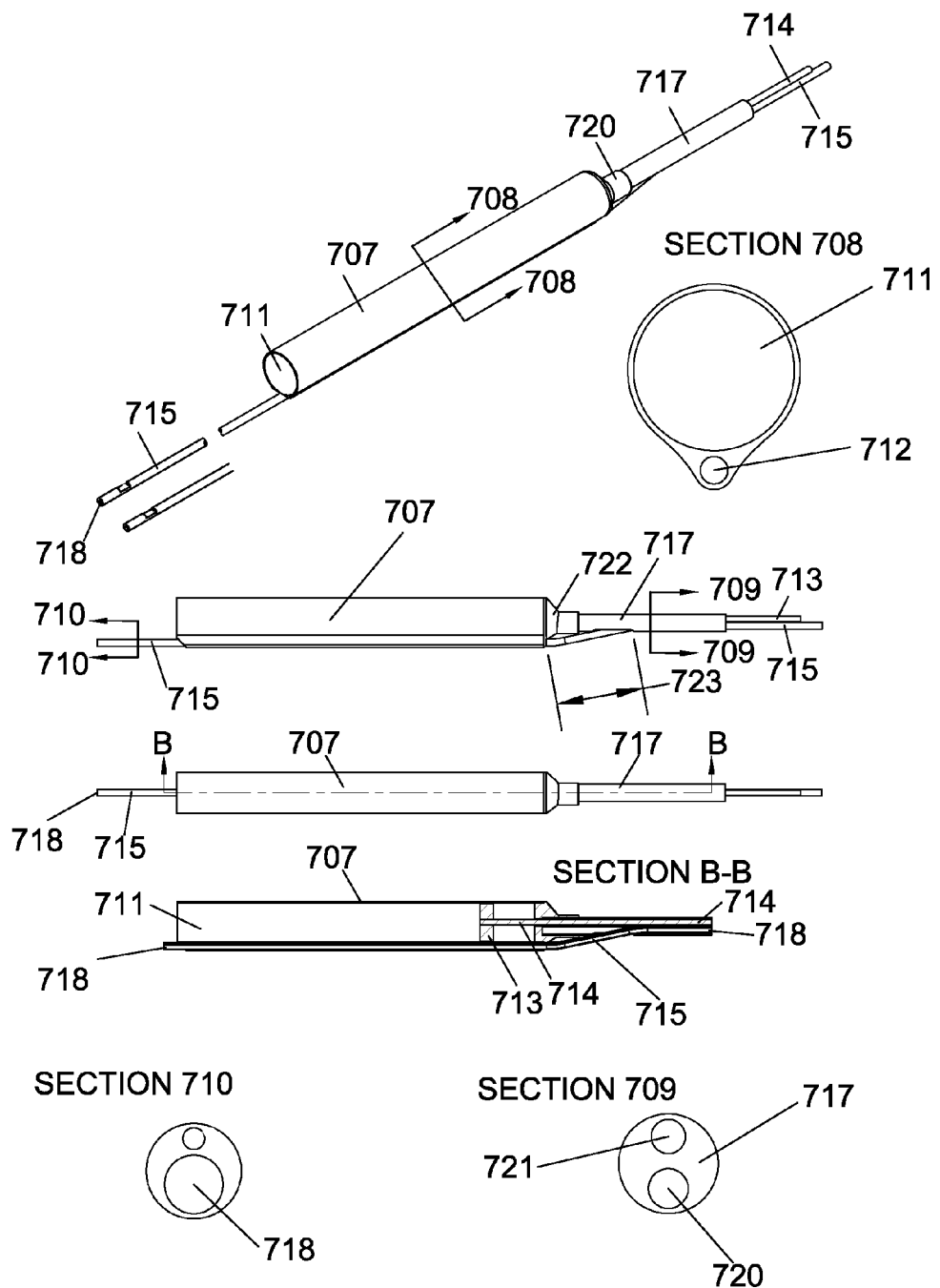
FIG. 52 is a drawing of a monorail delivery catheter for placing an expandable anchor and intestinal bypass sleeve within the digestive tract.

FIG. 52 is a cross-sectional drawing of an alternative embodiment of a delivery catheter for the invention herein disclosed. The delivery catheter is comprised of: distal outer capsule 707, which transitions down to a smaller diameter at the proximal outer sheath 717, sleeve delivery catheter 715, anchor pusher 714, and anchor pusher disk 713. Capsule connector 722 joins the distal outer capsule 707 to the proximal outer sheath 717. The distal outer capsule 707 is made from dual lumen tubing. The first lumen 711 is sized to accommodate the expandable anchor and can range in diameter from 3 mm to 12 mm. The second lumen 712 is sized to accommodate the sleeve delivery catheter 715 and can range in diameter from 1 mm to 4 mm. The distal outer capsule 707 may be made from a plastic polymer such as Pebax® (polyether block amide), Hytrel (polyester elastomer), ePTFE, PTFE, FEP, nylon 12, nylon 11, nylon 6, nylon 6,6, polyethylene, polyurethane or other suitable polymer. The distal outer capsule 707 may have an inner lining made from a polymer with a low coefficient of friction such as PTFE. The distal outer capsule 707 may also have a metal re-enforcement in the wall thickness to improve the kink resistance or burst properties of the outer sheath. The metal re-enforcement may be comprised of a braided wire mesh or a metal coil in the wall thickness. The wire used for the re-enforcement may have a round or rectangular cross section. The metal used for the braid may be stainless steel, Nitinol, MP35N, L605, Elgiloy or other suitable material. The distal outer capsule 707 length may range typically from 1-3 inches in length or alternatively up to the full length of the catheter.

The proximal outer sheath 717 is a dual lumen tube. The first lumen 720 is sized to accommodate the sleeve delivery catheter and may range in diameter from 1 mm to 4 mm. The second lumen 721 is sized to accommodate the anchor pusher 714 and may range in diameter from 1 to 4 mm size. The proximal outer sheath 717 may be made from a plastic polymer such as Pebax® (polyether block amide), PTFE, Hytrel (polyester elastomer), nylon 12, nylon 11, nylon 6, nylon 6,6, polyethylene, polyurethane or other suitable polymer. The proximal outer sheath 717 may have an inner lining made from a polymer with a low coefficient of friction such as PTFE. The proximal outer sheath 717 may also have a metal re-enforcement in the wall thickness to improve the kink resistance or burst properties of the outer sheath. The metal re-enforcement may be comprised of a braided wire mesh or a coil in the wall thickness. The metal used for the braid may be stainless steel, Nitinol, MP35N, L605, Elgiloy or other suitable material.

The anchor pusher disk 713 serves as a mechanical stop or means to hold stationery or push out the expandable anchor from the inside of the distal outer capsule 711. The anchor pusher disk 713 can be made from metal or plastic and it can incorporate the anchor retention features as previous disclosed in FIG. 35 and FIG. 39.

The anchor pusher 714 may be made from a plastic polymer such as Pebax® (polyether block amide), PEEK, Hytrel (polyester elastomer), nylon 12, nylon 11, nylon 6, nylon 6,6, polyethylene, polyurethane, polyimide, PTFE, FEP or other suitable polymer. The anchor pusher 714 may have an inner lining made from a polymer with a low coefficient of friction such as PTFE. The anchor 714 may also have a metal re-enforcement in the wall thickness to improve the kink resistance or burst properties of the outer sheath. The metal re-enforcement may be comprised of a braided wire mesh or a coil in the wall thickness. The metal used for the braid may be stainless steel, Nitinol, MP35N, L605, Elgiloy or other suitable material. Alternatively, the anchor pusher 714 may have a solid cross section and be made from metal such as stainless steel, Nitinol, MP35N, L605, Elgiloy or other suitable material or it may have a hollow core.

The sleeve delivery catheter 715 may be designed as previously disclosed in FIG. 41, FIG. 42, FIG. 44A, FIG. 44B or FIG. 46. The sleeve delivery catheter 715 may be made from a plastic polymer such as Pebax® (polyether block amide), PEEK, Hytrel (polyester elastomer), nylon 12, nylon 11, nylon 6, nylon 6,6, polyethylene, polyurethane or other suitable polymer. The sleeve delivery catheter 715 may have an inner lining in lumens 720 or 721 made from a polymer with a low coefficient of friction such as PTFE. The sleeve delivery catheter 715 may also have a metal re-enforcement in the wall thickness to improve the kink resistance.

The guide wire may be inserted through the sleeve delivery catheter lumen 718. Expandable anchor is compressed and loaded into the inside diameter 711 of the distal outer capsule 707. The intestinal bypass sleeve extends out beyond the end of the distal outer capsule 707. The sleeve delivery catheter 715 is inserted form the proximal end of lumen 720 to the distal end of lumen 720, sleeve delivery catheter 715 then transitions from lumen 720 to lumen 712 by spanning outside the catheter across segment 723.

The sleeve delivery catheter 715 is outside the lumen of the intestinal bypass sleeve and includes a feature adapted to mechanically retain the intestinal bypass sleeve to the end of the sleeve delivery catheter.

FIG. 53A through FIG. 56B are a deployment sequence for an expandable anchor and intestinal bypass sleeve when deployed with the catheter.

Figure 53A:
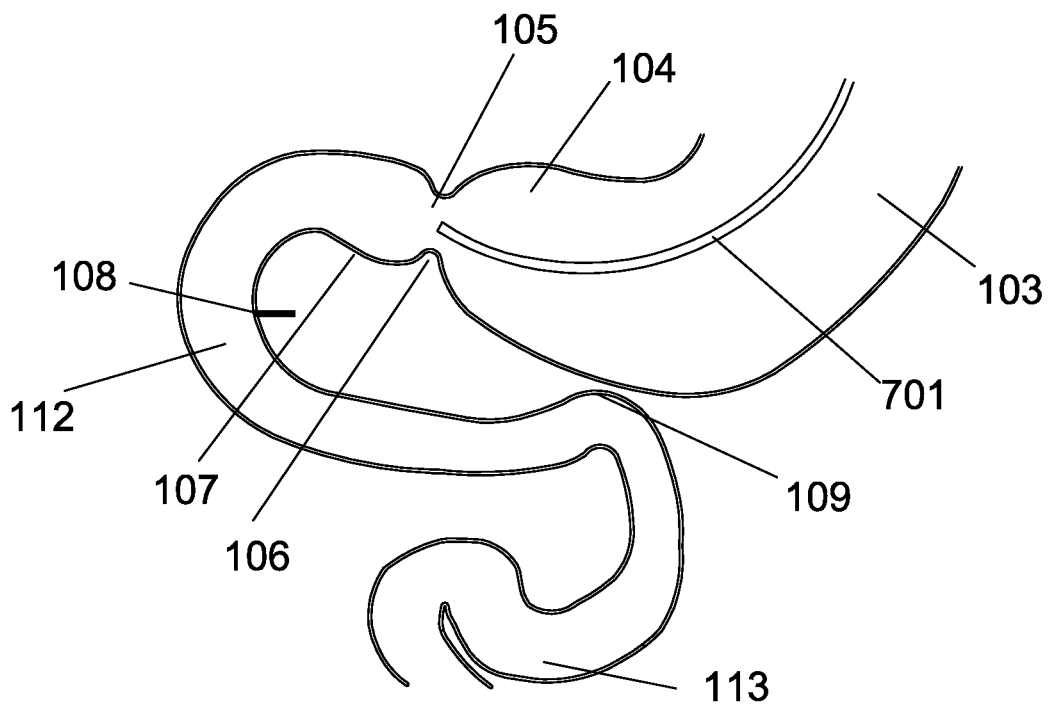
FIG. 53A is a cross-sectional view of a portion of the digestive tract in a human body with an endoscope inserted through the mouth, esophagus and stomach to the pylorus.

FIG. 53A is a cross-sectional view of a portion of the digestive tract in a human body with an endoscope 701 inserted through the mouth, esophagus and stomach to the pylorus.

Figure 53B:
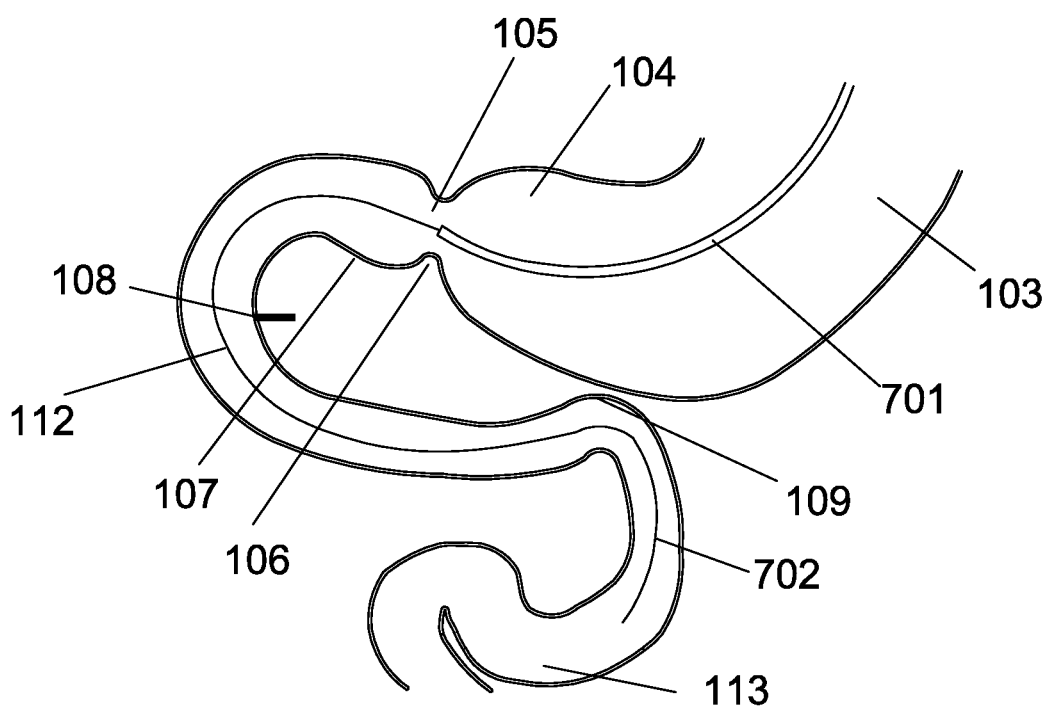
FIG. 53B is a cross-sectional view of a portion of the digestive tract in a human body with an endoscope inserted through the mouth, esophagus and stomach to the pylorus. A guide wire is inserted through the working channel of the endoscope. The guide wire is advanced distally in the small intestine lumen into the jejunum.

FIG. 53B is a cross-sectional view of a portion of the digestive tract in a human body with an endoscope inserted through the mouth, esophagus and stomach to the pylorus. A guide wire 702 is inserted through the working channel of the endoscope 701. The guide wire is advanced distally in the small intestine lumen into the jejunum.

Figure 54A:
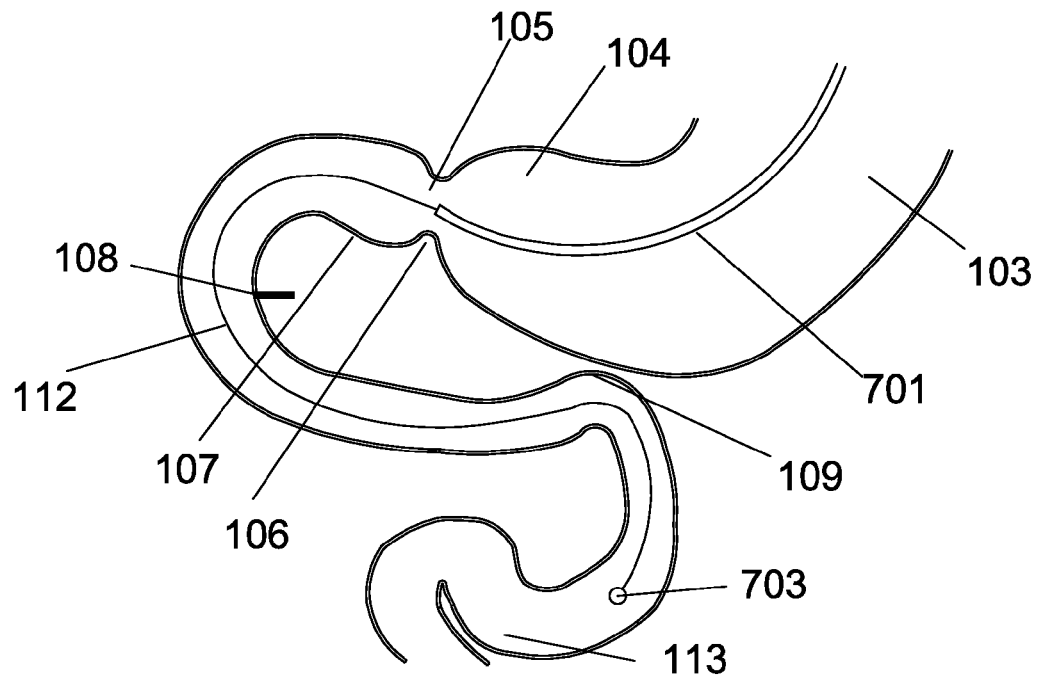
FIG. 54A is a cross-sectional view of a portion of the digestive tract in a human body with an endoscope inserted through the mouth, esophagus and stomach to the pylorus. The guide wire of FIG. 47 is back loaded into the working channel of the endoscope. The guide wire of FIG. 47 is advanced distally in the small intestine lumen into the jejunum.

FIG. 54A is a cross-sectional view of a portion of the digestive tract in a human body with an endoscope inserted through the mouth, esophagus and stomach to the pylorus. The guide wire 702 as previously disclosed in FIG. 47 with a ball attached to the distal end is back loaded into the working channel of the endoscope 701 prior to insertion of the endoscope. The guide wire 702 is advanced distally in the small intestine lumen into the jejunum.

Figure 54B:
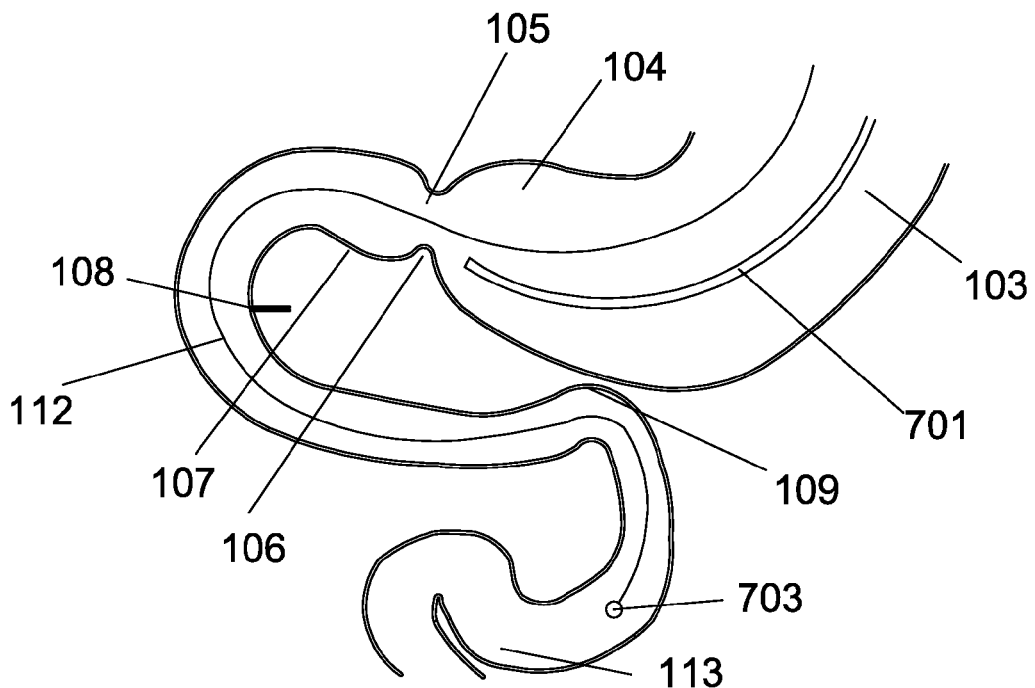
FIG. 54B is a cross-sectional view of a portion of the digestive tract in a human body with an endoscope inserted through the mouth, esophagus and stomach to the pylorus. The guide wire of FIG. 47 is left in place in the jejunum while the endoscope is withdrawn from the body. The endoscope is then reinserted into the stomach through the mouth and esophagus parallel to the guide wire, but the guide wire is not in the working channel of the endoscope.

FIG. 54B is a cross-sectional view of a portion of the digestive tract in a human body with an endoscope inserted through the mouth, esophagus and stomach to the pylorus. The guide wire of FIG. 47 is left in place in the jejunum while the endoscope is withdrawn from the body. The endoscope 701 is then reinserted into the stomach through the mouth and esophagus parallel to the guide wire 702, but the guide wire 702 is not in the working channel of the endoscope.

Figure 55:
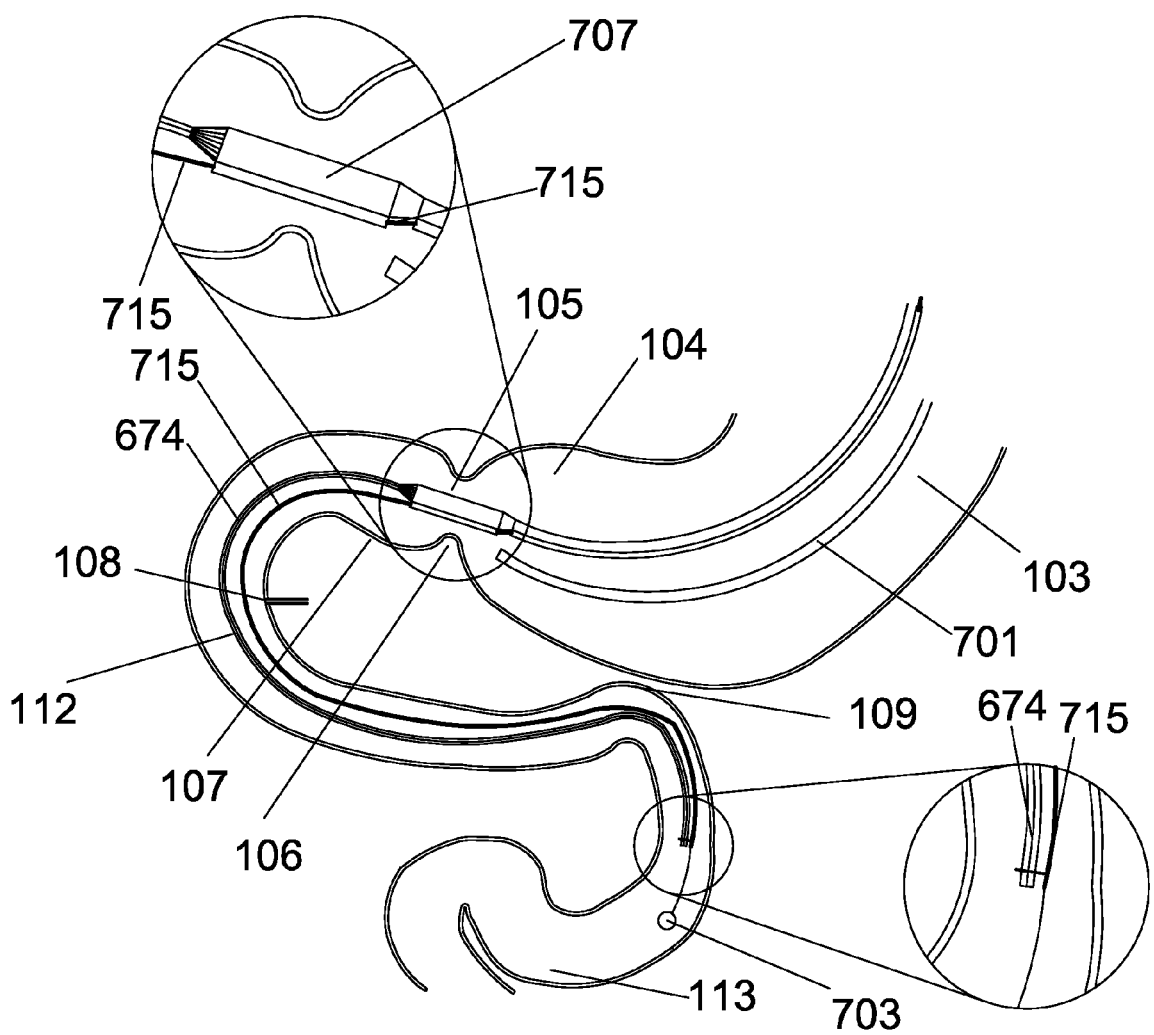
FIG. 55 is a continuation in the deployment sequence from FIG. 54B. An expandable anchor and intestinal bypass sleeve has been loaded onto a monorail delivery catheter. The delivery catheter is advanced over the guide wire through the mouth, esophagus, stomach and small intestine until the distal end of the sleeve reaches the desired implant location.

FIG. 55 is a continuation in the deployment sequence from FIG. 54B. An expandable anchor and intestinal bypass sleeve 704 have been loaded on to a delivery catheter. The delivery catheter and intestinal bypass sleeve 704 are advanced over the guide wire 703 through the mouth, esophagus, stomach and small intestine until the distal end of the intestinal bypass sleeve 704 reaches the desired implant location. The sleeve delivery catheter 715 is parallel to (along the outside surface) of the intestinal bypass sleeve 674. The release wire FIG. 40 item 677 on the sleeve delivery catheter is then retracted FIG. 40 in the direction 680 to release the intestinal bypass sleeve 704 from the distal end of the sleeve delivery catheter. The ball on the end of the guide wire is now released and left to pass naturally through the digestive tract. The ball on the end of the guide wire can alternatively be made from a bioabsorbable polymer and dissolves upon release from the guide wire.

The guide wire and sleeve delivery catheter are now removed from the body.

Figure 56A:
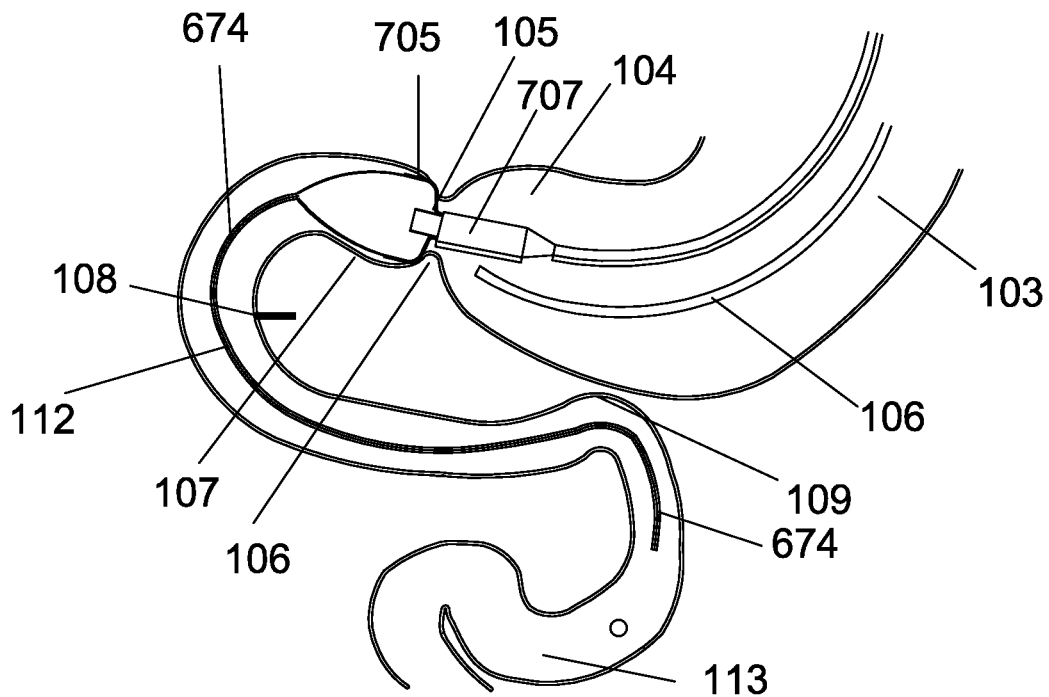
FIG. 56A is a continuation in the deployment sequence from FIG. 55. The sleeve delivery catheter is actuated to release the distal end of the bypass sleeve from the catheter. The sleeve delivery catheter is then retracted to remove it partially or fully from the digestive system. The distal capsule of the delivery system then is partially retracted to deploy or release the distal end of the expandable anchor from the distal capsule.

FIG. 56A is a continuation in the deployment sequence from FIG. 55A. The sleeve delivery catheter distal outer capsule 707 is partially retracted proximally to deploy or release the distal end of the expandable anchor 705 from the distal outer capsule 707.

Figure 56B:
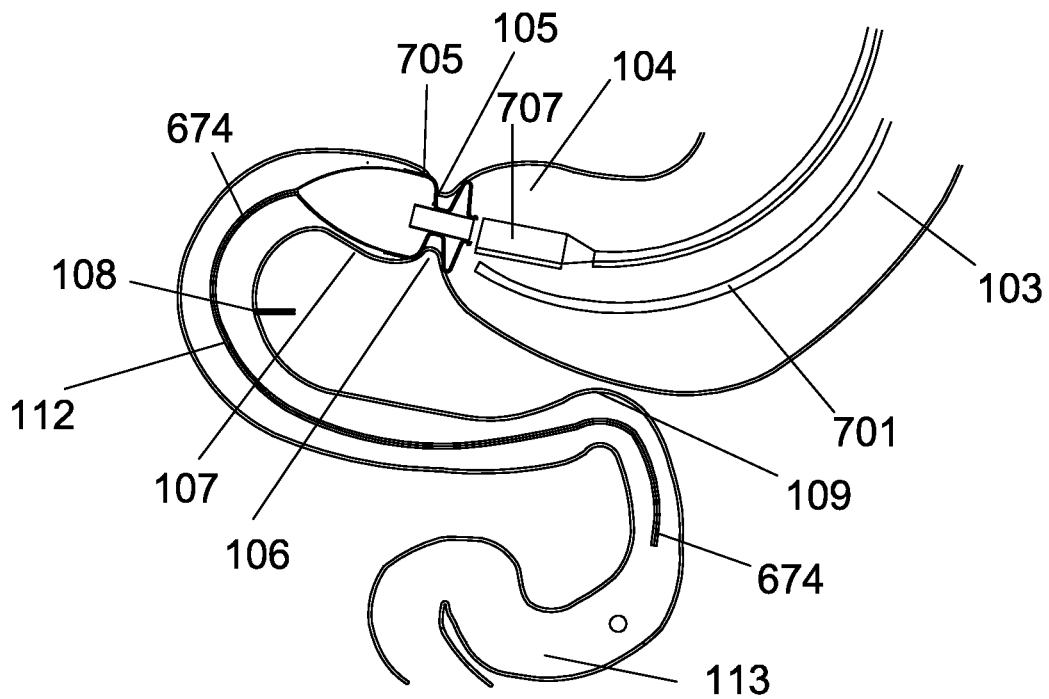
FIG. 56B is a continuation in the deployment sequence from FIG. 56A. The distal capsule of the delivery system is fully retracted to deploy or release the proximal end of the expandable anchor from the distal capsule. The expandable anchor and intestinal bypass sleeve are now in place at the intended implant location. The ball on the end of the guide wire is released. The guide wire, delivery catheter and endoscope are withdrawn from the human body.

FIG. 56B is a continuation in the deployment sequence from FIG. 56A. The distal outer capsule 706 of the delivery system is fully retracted to deploy or release the proximal end of the expandable anchor 705 from the distal capsule. The expandable anchor 705 and the intestinal bypass sleeve 704 are now in place at the intended implant location. The delivery catheter and endoscope 701 are withdrawn from the human body.

Figure 57:
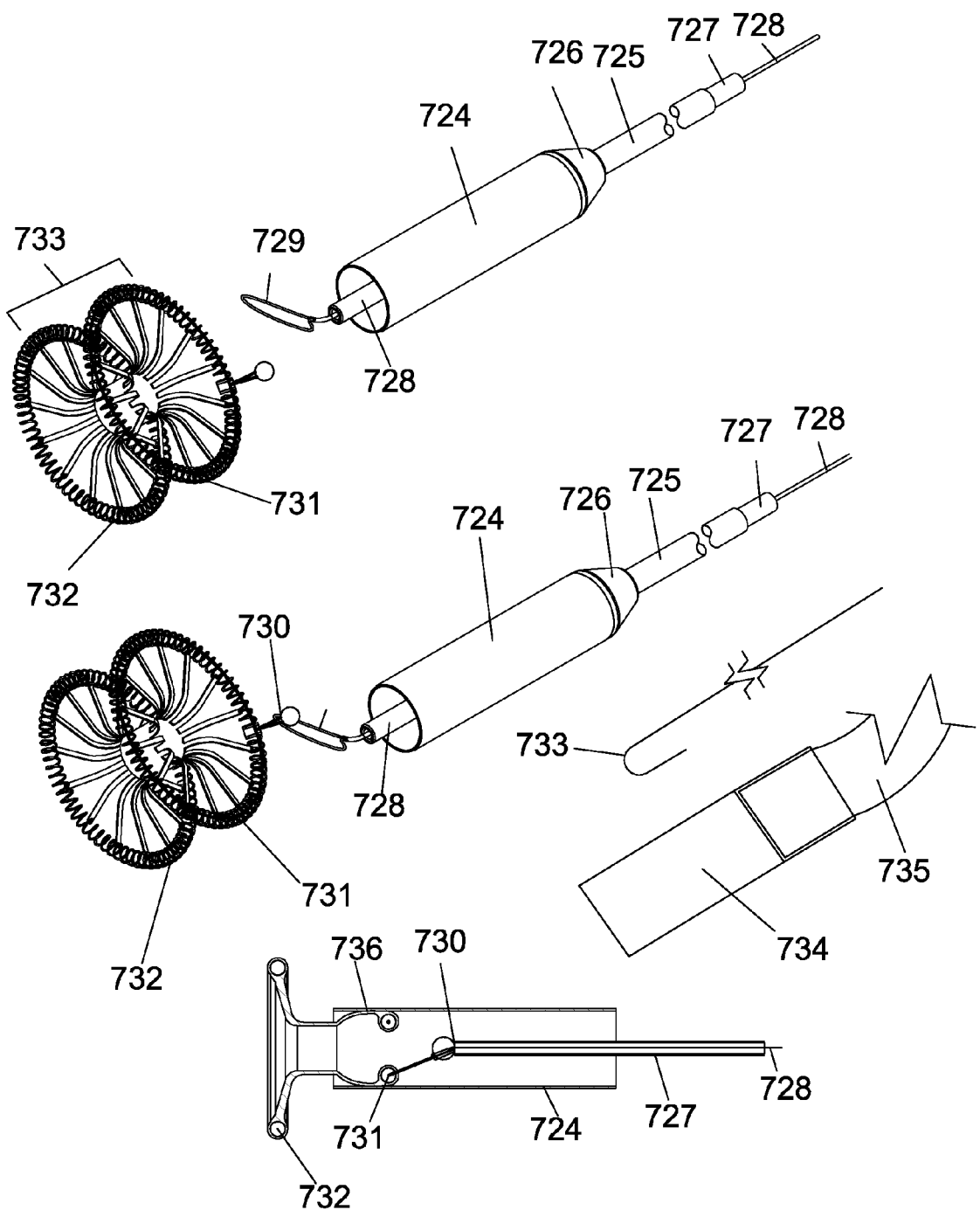
FIG. 57 is a drawing of a catheter for removal of an expandable anchor and bypass sleeve as in FIG. 16 from the human body.

FIG. 57 is a drawing of a removal catheter for removing an expandable anchor and intestinal bypass sleeve from the human body. The removal catheter is comprised of a recovery outer tube 724, an outer tube connector 726, proximal outer tube 725, snare catheter 727, and a snare loop 729. An expandable anchor 733 as was previously disclosed in FIG. 7 has a proximal disk 731 and a distal disk 732. The expandable anchor 733 is shown without a polymer covering or without an intestinal bypass sleeve attached. The expandable anchor 733 is implanted in the gastrointestinal tract. To remove the expandable anchor the removal catheter is advanced through the anatomy to the implant location. The snare loop 729 is placed around the ball 730. The snare loop 729 is drawn into the snare recovery catheter 728 to close the snare loop 729 diameter and to apply tension onto the ball 730. The closed snare loop 729 and ball 730 is drawn inside of the recovery outer tube 724, this causes the proximal disk 731 to contact the distal end of the recovery outer tube. The drawstring in the proximal disk 731 is tensioned with further withdrawal of the snare loop and snare recovery catheter within the proximal outer tube. The tension on the drawstring causes the proximal disk 731 to compress in diameter and the proximal end of the expandable anchor is captured 736 within the recovery outer tube 724. Continued retraction on the snare catheter 728 and snare loop 729 would cause the distal disk 732 of the expandable anchor 723 to compress in diameter and to be pulled inside of the recovery outer tube until the entire expandable anchor 733 is re-sheathed. An alternative embodiment of the snare loop 729 is a simple hook 733 to grab a loop of suture or ball as previously disclosed. An alternative embodiment of the recovery outer tube 724 is to use an endoscope hood 734 press-fit onto the end of an endoscope 735. The snare catheter 729 and snare recovery catheter 728 would be used through the working channel of the endoscope to grab the ball 730 and tension the draw sting to collapse the proximal disk and pull the expandable anchor into the endoscope hood.

Figure 58:
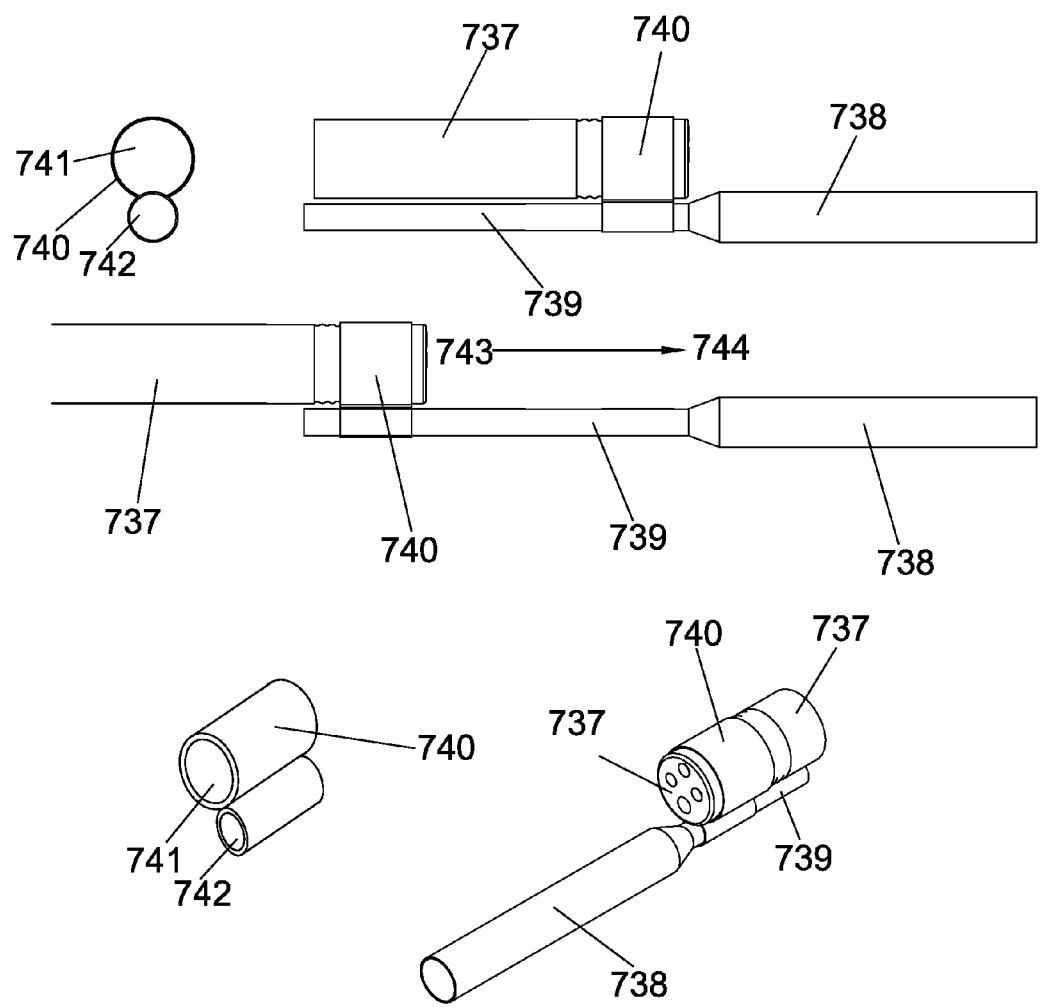
FIG. 58 is a drawing of a monorail guide eyelet that may be attached to the end of the endoscope.

FIG. 58 is a drawing of a monorail type eyelet 740 that can be used on the end of an endoscope 737. The eyelet 740 has two lumens. Lumen 742 is sized to be a loose fit (sliding fit) on the outer diameter of the proximal outer tube 649 as shown in FIG. 43 of a delivery catheter for an expandable anchor. Lumen 741 is sized to be a tight or friction fit on the end of an endoscope 737. When implanting expandable anchors within the human body it is sometimes difficult to navigate the delivery catheter to the required path in the pyloric canal. It is desirable to be able to removably couple the end of the endoscope to the delivery catheter and advance the distal end of the endoscope by sliding the eyelet 740 down the proximal outer tube 739 from location 743 to 744. With the distal end of the endoscope near the distal outer capsule the endoscope 737 steering mechanism can be used to advance the catheter through tortuous anatomy and across the pylorus.

Figure 59:
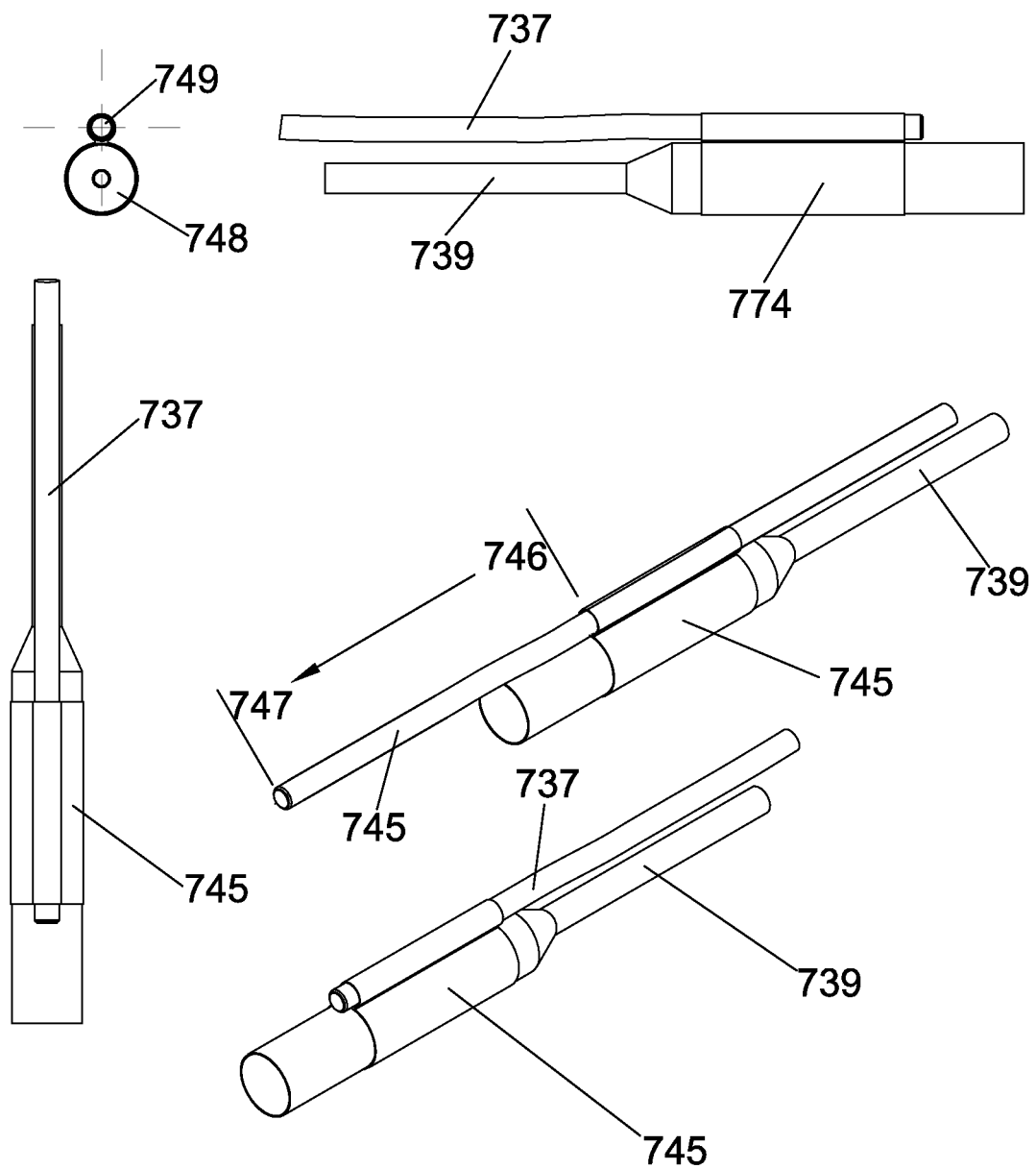
FIG. 59 is a drawing of a monorail guide eyelet that may be incorporated into the distal capsule of the expandable anchor delivery device.

FIG. 59 is a drawing of a monorail type eyelet 745 that can be attached to a distal outer capsule. The eyelet 745 has two lumens. Lumen 749 is sized to be a loose fit (sliding fit) on the outer diameter of an endoscope 737. Eyelet 745 can be made from metal or plastic. Eyelet 745 can have a liner made from PTFE in lumen 749. Lumen 741 is sized to be a tight or friction fit on or bonded onto a distal outer capsule. When implanting expandable anchors within the human body it is sometimes difficult to navigate the delivery catheter to the required path in the pyloric canal. It is desirable to be able to removably couple the end of the endoscope to the delivery catheter and advance the distal end of the endoscope by sliding the eyelet 745 down an endoscope 737 from location 746 to 747. With the distal end of the endoscope near the distal outer capsule the endoscope 737 steering mechanism can be used to advance the catheter through tortuous anatomy and across the pylorus.

Figure 60:
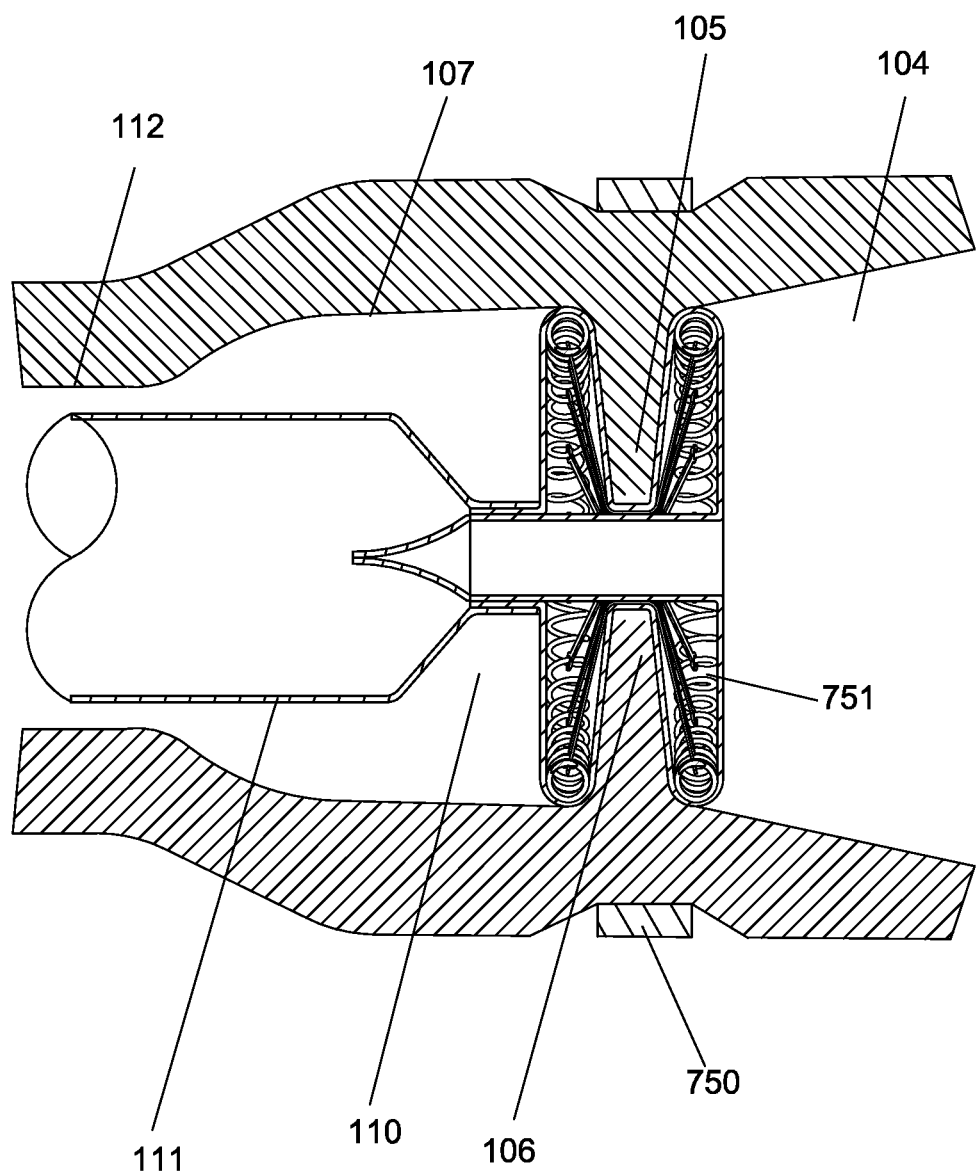
FIG. 60 is a drawing of the expandable anchor herein disclosed implanted across a pylorus. An external band has been surgically placed with a laparoscope around the pylorus. The band around the pylorus will increase the radial compliance/stiffness of the pylorus and will provide for an increased force to cause dislodgment of the expandable anchor from within the pylorus.

FIG. 60 is an expandable anchor 751 and an intestinal bypass sleeve 111 which is implanted across a pylorus 105 and into the duodenum 112. An external band 750 has been laparoscopically implanted around the outside of the pylorus 105 prior to placement of the expandable anchor as was previously disclosed in co-pending U.S. patent application Ser. No. 13/298,867, filed Nov. 17, 2011. The external band 750 provides additional radial stiffness to the pyloric tissue and increases the securement force or required force to displace the expandable anchor 751 from within the pylorus 106.

Figure 61:
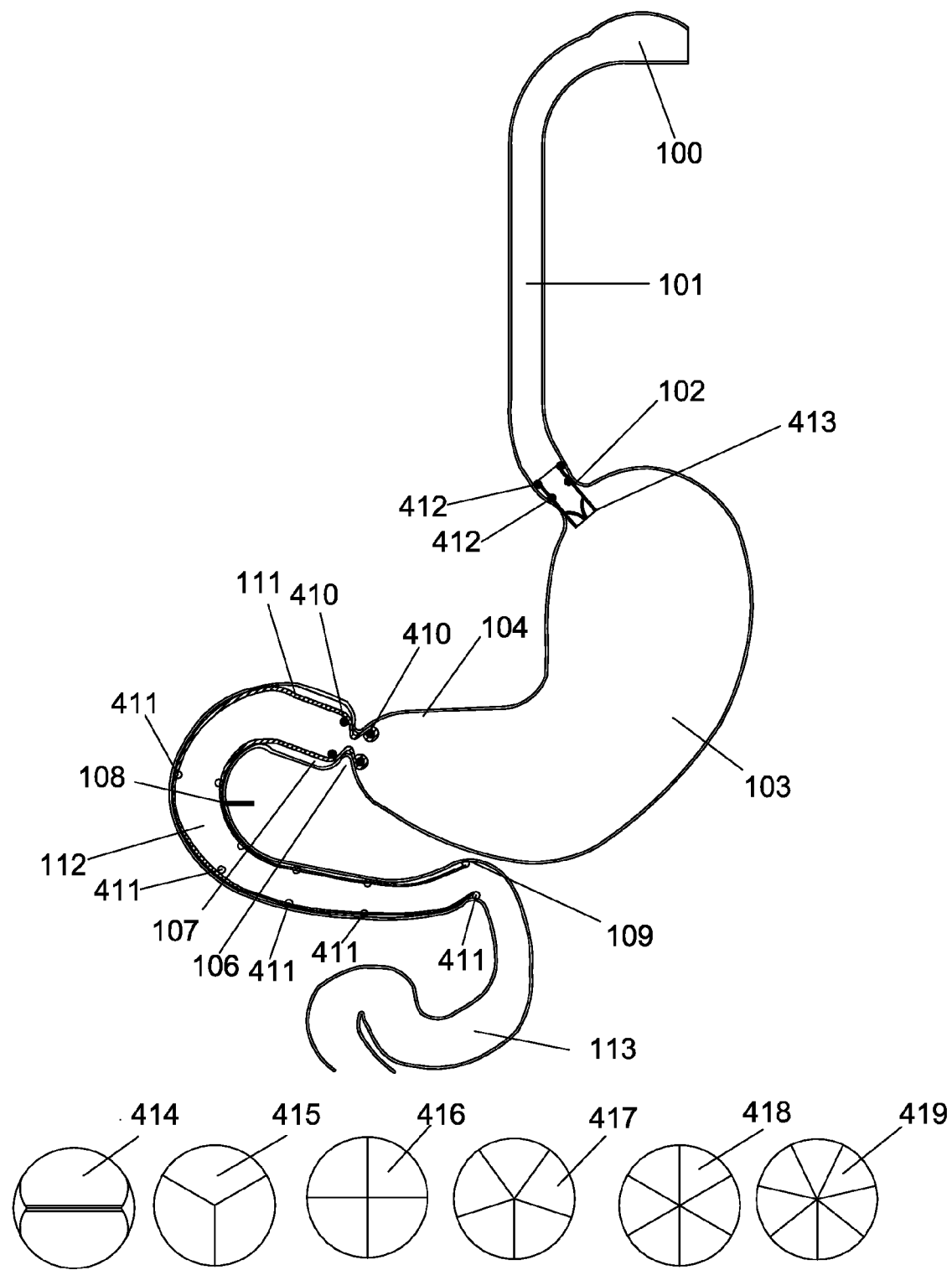
FIG. 61 is a cross-sectional view of a portion of the digestive tract in a human body. An intestinal bypass sleeve is implanted in the duodenum from the pylorus to the ligament of Treitz. The sleeve is held in place at the pylorus by an expandable anchor that anchors on the pylorus, optional secondary expandable anchors anchor the sleeve at additional locations in the duodenum and jejunum. An expandable anchor with an anti-reflux valve is implanted at the gastroesophageal (GE) junction to help resolve gastroesophageal reflux disease (GERD).

FIG. 61 is a cross-sectional view of a portion of the digestive tract in a human body. An intestinal bypass sleeve 111 is implanted in the duodenum 112 from the pylorus 106 to the ligament of Treitz 109. The sleeve is held in place at the pylorus 106 by expandable anchors 410 that anchor on the pylorus 106. Optional secondary expandable anchors 411 anchor the intestinal bypass sleeve 111 at additional locations in the duodenum 112 and jejunum 113. An expandable anchor 412 with an anti-reflux valve is implanted at the gastroesophageal (GE) junction 102 to help resolve gastroesophageal reflux disease (GERD). Reference numbers 414, 415, 416, 417, 418 and 419 denote valve designs that have from two to seven flaps in the valve and may be used for the anti-reflux device 413.

Figure 62:
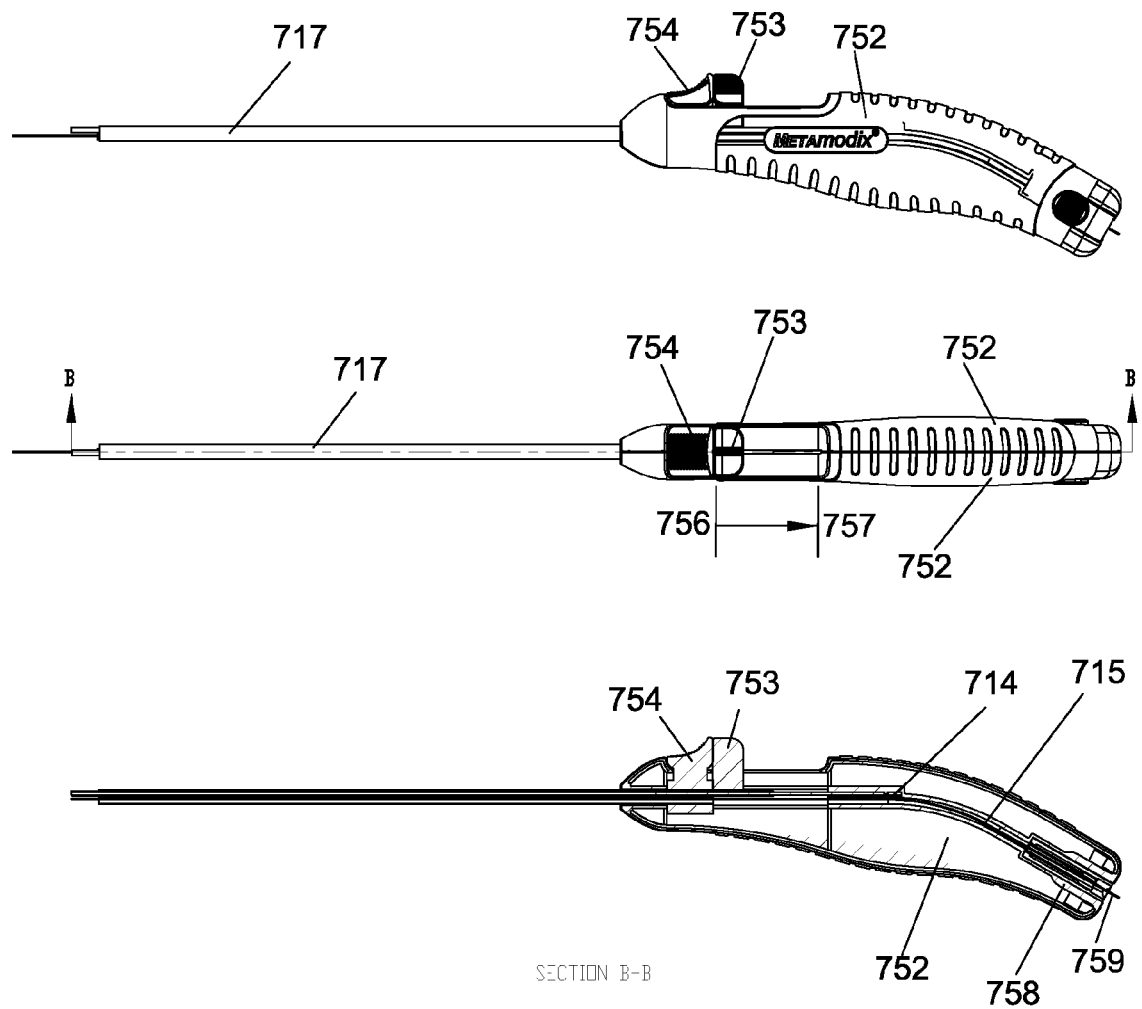
FIG. 62 is a drawing of a deployment handle for a delivery catheter for expandable anchors and intestinal bypass sleeves.

FIG. 62 is a drawing of a handle set for a delivery catheter as previously disclosed in FIG. 52. The handle set is comprised of a molded handle housing 752, deployment slide 754, slide lock 753, proximal outer tube 717, sleeve delivery catheter proximal end 715 and sleeve delivery lock clip 758. The handle components can be made from plastic such as polycarbonate, ABS, PEEK, Nylon, PET, PBT or other suitable polymer or metal. The handle housing is made in a two piece clam shell configuration. The proximal outer sheath 717 is attached the deployment slide 754. The anchor pusher 714 is fixed to the handle housing 752. To retract the distal outer capsule 707 the slide lock 753 is removed from the handle housing 752, the deployment slide 754 which is bonded to the proximal outer tube 717 is retracted. The anchor pusher is fixed to the handle housing, so the proximal end of the expandable anchor is stationery as the distal outer capsule retracts with the proximal outer tube to unsheath the distal end of the expandable anchor. Deployment of the expandable anchor occurs as the deployment slide is moved from position 756 to 757. The sleeve delivery catheter can be secured to the handle housing with a snap fit feature at 758.

A guide wire can be inserted through the catheter and handle set at 759.

Figure 63:
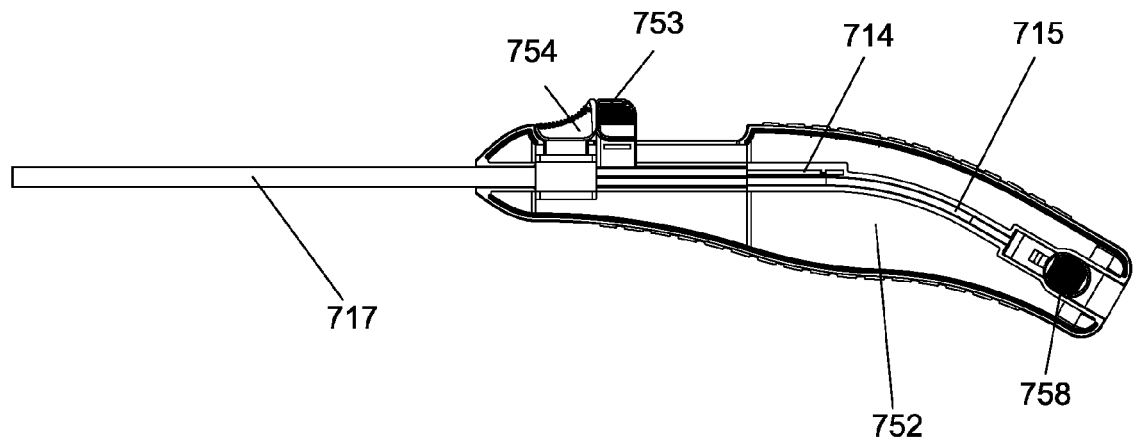
FIG. 63 is a drawing of a deployment handle for a delivery catheter for expandable anchors and intestinal bypass sleeves.
Figure 63:
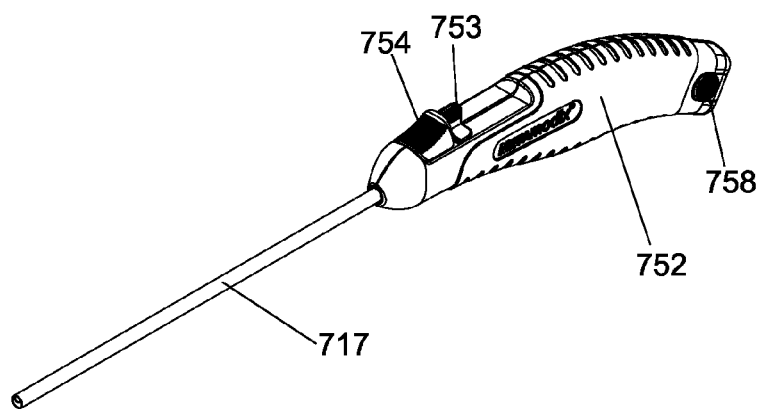

FIG. 63 is an additional view of the handle disclosed in FIG. 62.

Figure 64:
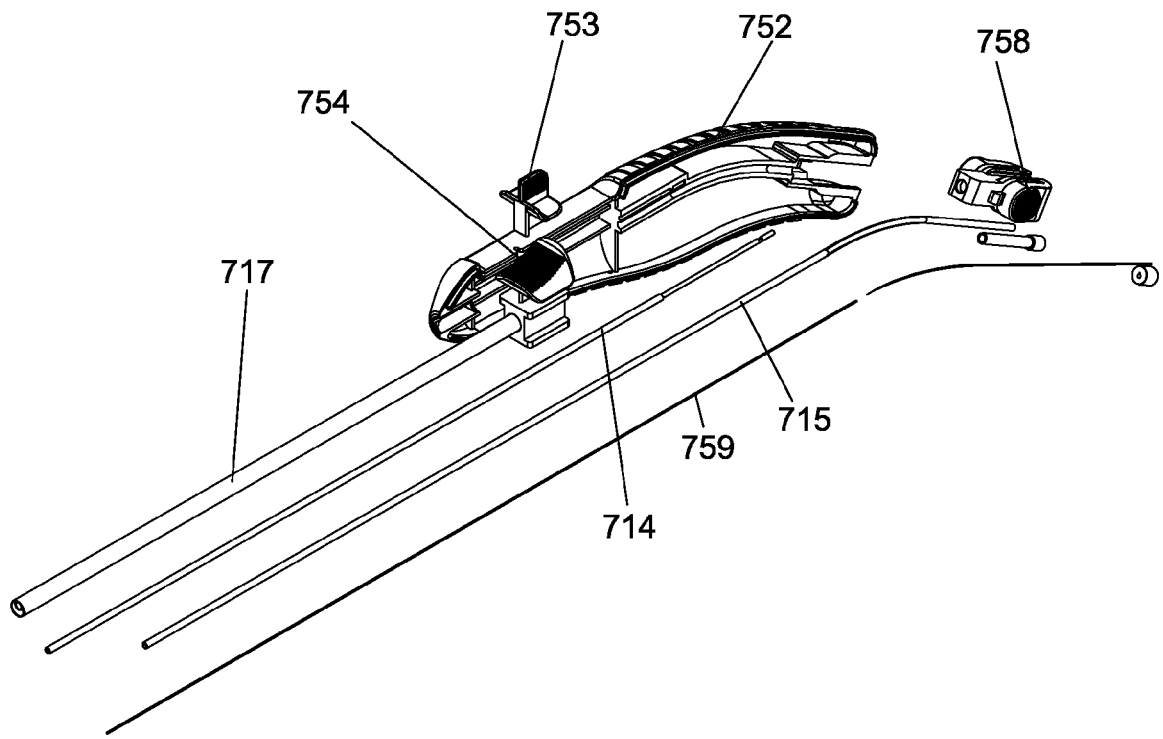
FIG. 64 is a drawing of a deployment handle for a delivery catheter for expandable anchors and intestinal bypass sleeves.

FIG. 64 is an additional view of handle disclosed in FIG. 62.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A system for delivery and implantation of a gastrointestinal device within one or more of a pyloric antrum, a pylorus, a duodenal bulb, a duodenum, and a jejunum of a patient's gastrointestinal tract, the system comprising:
    an anchor having a collapsed configuration for delivery and an expanded configuration for anchoring within one or more of the pyloric antrum, the pylorus, and the duodenum;
    an intestinal bypass sleeve coupled to and extending from an end of the anchor;
    an anchor and sleeve delivery device comprising:
        a distal outer capsule having a first lumen that is sized and configured to retain the anchor in the collapsed configuration and a second lumen disposed adjacent to the first lumen;
        a proximal outer sheath coupled to the distal outer capsule;
        a sleeve delivery catheter slidably disposed within the second lumen of the distal outer capsule and the proximal outer sheath, the sleeve delivery catheter having a longitudinal guide wire lumen sized and shaped to accept a guide wire, the sleeve delivery catheter having a sleeve coupling feature for releasably coupling to the intestinal bypass sleeve; and
        an anchor pusher slidably disposed in the proximal outer sheath and configured to extend into the first lumen of the distal outer capsule to push the anchor out of the distal outer capsule and deploy the anchor to the expanded configuration.

2. The system of claim 1 wherein the anchor is self-expanding such that upon deployment from the outer capsule the anchor assumes the expanded configuration.

3. The system of claim 1 wherein the distal outer capsule of the anchor delivery device has a first diameter and the proximal sheath has a second diameter, smaller than the first diameter, further wherein the first lumen has a diameter of from about 3 mm to about 12 mm and the second lumen has a diameter of from about 1 mm to about 4 mm.

4. The system of claim 1 wherein the proximal sheath has a first lumen in communication with the first lumen of the distal outer capsule and a second lumen in communication with the second lumen of the distal outer capsule.

5. The system of claim 4 wherein the anchor pusher has an anchor contact feature and an elongated pusher, wherein the anchor contact feature is sized and shaped to fit within the first lumen of the distal outer sheath and to contact the anchor and the elongated pusher is configured to fit within the first lumen of the proximal sheath.

6. The system of claim 4 wherein the distal outer capsule is made from a polymer selecting from the group including: a polyether block amide, a polyester elastomer, a PTFE, an FEP, a nylon, a polyethylene or a polyurethane.

7. The system of claim 1 wherein the distal outer capsule has an inner lining made from PTFE and a length of from about 1 to about 3 inches.

8. The system of claim 5 wherein the anchor contact feature includes a retention feature for releasably coupling with the anchor.

9. The system of claim 1 wherein the sleeve coupling feature of the sleeve delivery catheter is a loop, sized to extend around an outside diameter of the intestinal bypass sleeve.

* * * * *